United States Patent
Ohta et al.

(10) Patent No.: US 10,610,440 B2
(45) Date of Patent: Apr. 7, 2020

(54) SWINGING JOINT DEVICE, WALKING ASSISTING DEVICE, CONVEYING DEVICE, MANIPULATOR, AND WALKING-ABILITY ASSISTING DEVICE

(71) Applicant: JTEKT CORPORATION, Osaka-shi (JP)

(72) Inventors: Hiromichi Ohta, Kariya (JP); Kazuyoshi Ohtsubo, Chiryu (JP)

(73) Assignee: JTEKT CORPORATION, Osaka-shi (JP)

(*) Notice: Subject to any disclaimer, the term of this patent is extended or adjusted under 35 U.S.C. 154(b) by 839 days.

(21) Appl. No.: 15/065,481

(22) Filed: Mar. 9, 2016

(65) Prior Publication Data
US 2016/0262969 A1    Sep. 15, 2016

(30) Foreign Application Priority Data
Mar. 10, 2015  (JP) .................................. 2015-047540
Mar. 10, 2015  (JP) .................................. 2015-047541
(Continued)

(51) Int. Cl.
*A61H 3/00*    (2006.01)
*A61H 1/02*    (2006.01)
(Continued)

(52) U.S. Cl.
CPC ............. *A61H 3/00* (2013.01); *A61H 1/0255* (2013.01); *A61H 1/0262* (2013.01); *A61F 5/00* (2013.01);
(Continued)

(58) Field of Classification Search
CPC ...... A61H 1/00; A61H 1/0214; A61H 1/0237; A61H 1/0244; A61H 1/0255;
(Continued)

(56) References Cited

U.S. PATENT DOCUMENTS 5,571,078 A * 11/1996 Malewicz ............. A61F 5/0125
                                                128/882
5,954,677 A *  9/1999 Albrecht ............... A61F 5/0125
                                                 602/16
(Continued)

FOREIGN PATENT DOCUMENTS

JP    2004-344304      12/2004
JP    2012-125388       7/2012
(Continued)

OTHER PUBLICATIONS

Combined Chinese Office Action and Search Report dated Jun. 17, 2019, in Patent Application No. 201610136319.6, 17 pages (with partial English translation).

*Primary Examiner* — Justine R Yu
*Assistant Examiner* — Matthew R Moon
(74) *Attorney, Agent, or Firm* — Oblon, McClelland, Maier & Neustadt, L.L.P.

(57) ABSTRACT

A swinging joint device includes a driving shaft member; a first output portion that swings about a driving axis serving as an axis of the driving shaft member; an elastic body that generates an urging torque corresponding to a first swinging angle that is a swinging angle of the first output portion; an apparent rigidity variable portion that varies apparent rigidity of the elastic body seen from the first output portion; a first angle detection portion that detects the first swinging angle; and a control portion that controls the apparent rigidity variable portion according to the first swinging angle detected by the first angle detection portion to adjust the apparent rigidity of the elastic body seen from the first output portion.

15 Claims, 24 Drawing Sheets

(30) Foreign Application Priority Data

| | | |
|---|---|---|
| Mar. 10, 2015 | (JP) | 2015-047542 |
| Apr. 10, 2015 | (JP) | 2015-080605 |
| Apr. 10, 2015 | (JP) | 2015-080606 |
| Apr. 10, 2015 | (JP) | 2015-080607 |
| Dec. 18, 2015 | (JP) | 2015-247378 |

(51) Int. Cl.
*A61F 5/02* (2006.01)
*A61F 5/00* (2006.01)
*B25J 9/00* (2006.01)

(52) U.S. Cl.
CPC .......... *A61F 5/02* (2013.01); *A61H 2003/007* (2013.01); *A61H 2201/1223* (2013.01); *A61H 2201/149* (2013.01); *A61H 2201/1463* (2013.01); *A61H 2201/164* (2013.01); *A61H 2201/165* (2013.01); *A61H 2201/1614* (2013.01); *A61H 2201/1619* (2013.01); *A61H 2201/1676* (2013.01); *A61H 2201/5007* (2013.01); *A61H 2201/5061* (2013.01); *A61H 2201/5069* (2013.01); *A61H 2205/10* (2013.01); *B25J 9/0006* (2013.01)

(58) Field of Classification Search
CPC ............... A61H 1/0262; A61H 1/2001; A61H 2001/165; A61H 2001/1652; A61H 2001/0203; A61H 2001/024; A61H 2001/0266; A61H 2001/0274; A61H 2001/0277; A61H 2001/0281; A61H 2001/0285; A61H 2205/088; A61H 2205/10; A61H 2205/108; A61H 3/00; A61H 3/008; A61H 2003/007; A61F 5/02; A61F 5/022; A61F 5/024; A61F 5/026; A61F 5/028; A61F 5/0102; A61F 5/0585; A61F 5/0123; A61F 5/01; A41F 9/00; A41F 9/025; A63B 21/022–026; A63B 21/153; B25J 9/0006; B25J 9/162; Y10S 901/01; Y10S 901/08; G05B 2219/45083

See application file for complete search history.

(56) References Cited

U.S. PATENT DOCUMENTS

| | | | | |
|---|---|---|---|---|
| 7,393,335 | B2* | 7/2008 | Carvey | A61F 5/0102 602/26 |
| 8,057,410 | B2* | 11/2011 | Angold | A61H 3/00 601/35 |
| 8,311,671 | B2* | 11/2012 | Tokita | A61H 1/0237 700/245 |
| 8,968,227 | B2* | 3/2015 | Rokosz | A61F 5/0125 601/35 |
| 9,216,130 | B2* | 12/2015 | Killian | A61H 1/0244 |
| 2003/0062241 | A1* | 4/2003 | Irby | A61F 5/0125 192/81 C |
| 2007/0010378 | A1 | 1/2007 | Katoh et al. | |
| 2007/0270976 | A1* | 11/2007 | DeHarde | A61F 5/0125 623/27 |
| 2014/0276304 | A1* | 9/2014 | Dollar | A61F 5/0102 602/16 |
| 2015/0173929 | A1* | 6/2015 | Kazerooni | A61F 5/0125 602/16 |
| 2016/0023350 | A1* | 1/2016 | Holgate | A45F 3/00 248/550 |

FOREIGN PATENT DOCUMENTS

| | | |
|---|---|---|
| JP | 2013-236741 | 11/2013 |
| WO | WO 2014/039134 A1 | 3/2014 |

\* cited by examiner

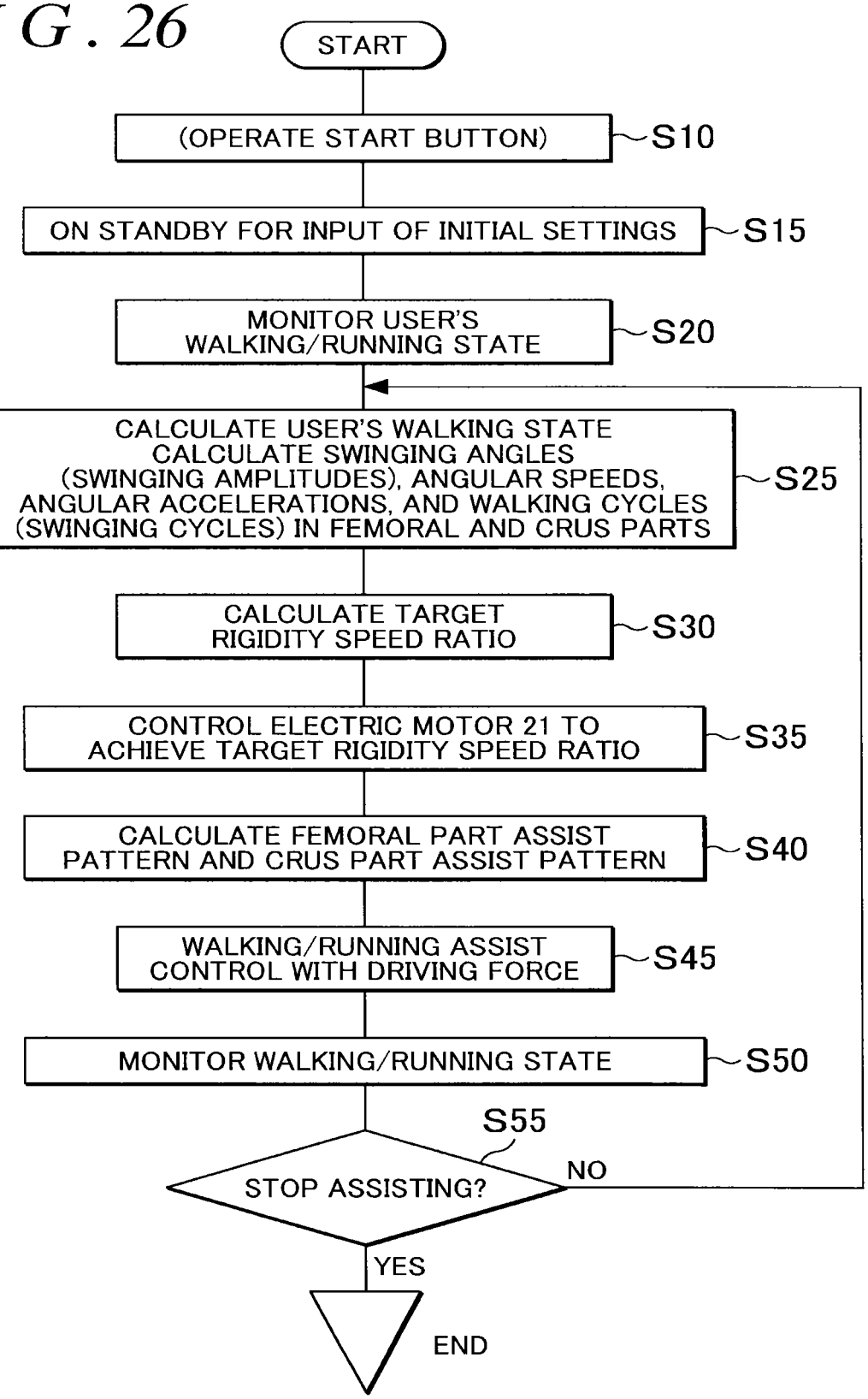

ND WALKING-ABILITY
SWINGING JOINT DEVICE, WALKING ASSISTING DEVICE, CONVEYING DEVICE, MANIPULATOR, AND WALKING-ABILITY ASSISTING DEVICE

INCORPORATION BY REFERENCE

The disclosure of Japanese Patent Applications No. 2015-080606 and No. 2015-080607 filed on Apr. 10, 2015 and No. 2015-247378 filed on Dec. 18, 2015 each including the specification, drawings and abstract is incorporated herein by reference in its entirety.

BACKGROUND OF THE INVENTION

1. Field of the Invention

The invention relates to a swinging joint device, a walking assisting device, a conveying device, and a manipulator each of which performs cyclic swinging motion and includes a joint with variable rigidity. In addition, the invention relates to a walking-ability assisting device that assists user's walking or running.

2. Description of Related Art

As an example of a device that controls a joint that performs cyclic swinging motion, Japanese Patent Application Publication No. 2004-344304 (JP 2004-344304 A) discloses a walking assisting device that applies an assisting force to the lower limb (ranging from the hip joint to the foot) of a user. The walking assisting device includes a waist-part outfit attached so as to wind the waist part of a user, a joining bar extending from the lateral side of the hip joint to the lateral side of the knee joint of the user, a crus-part outfit extending from the lateral side of the knee joint to the calf of the user, a hip joint actuator attached to the joint bar at a position on the lateral side of the hip joint, and a knee joint actuator attached to the joint bar at a position on the lateral side of the knee joint. The hip joint actuator is attached to the joining portion of the waist-part outfit. The hip joint actuator on the lateral side of the hip joint swings the joining bar in a front-rear direction about the hip joint relative to the waist-part outfit. In addition, the knee joint actuator on the lateral side of the knee joint swings the crus-part outfit in the front-rear direction about the knee joint relative to the joining bar. The hip joint actuator and the knee joint actuator are electric motors, and power is supplied to the electric motors from a battery attached to the waist-part outfit.

In addition, Japanese Patent Application Publication No. 2012-125388 (JP 2012-125388 A) discloses a walking rehabilitation device that assists the swinging motion of the crus (ranging from the knee to the ankle) of a user. The walking rehabilitation device includes a controller disposed around the waist of a user, a femoral link extending from the lateral side of the hip joint to the lateral side of the knee joint of the user, crus links extending from both lateral sides of the knee joint to the ankle joint of the user, a motor disposed on the lateral side of the knee joint, and foot links extending from the ankle joint to the sole of the user. The motor is attached at the joining portion between the femoral link and the crus links and on the lateral side of the knee joint. The motor on the lateral side of the knee joint swings the crus links in the front-rear direction about the knee joint relative to the femoral link. Power is supplied to the motor from a battery included in the controller.

Moreover, Japanese Patent Application Publication No. 2013-236741 (JP 2013-236741 A) discloses a one-leg walking assisting machine that is attached to a leg in trouble of a user having one leg in good condition and the other leg in trouble, to assist the swinging motion of the leg in trouble. The one-leg walking assisting machine includes a waist attachment portion disposed on the lateral side of the waist of a user, a femoral link portion extending from the lateral side of the hip joint to the lateral side of the knee joint of the user, a crus link portion extending downward from the lateral side of the knee joint, a torque generation unit disposed on the lateral side of the hip joint, and a damper disposed on the lateral side of the knee joint. The torque generation unit is constituted by a cam and a compression spring, generates a torque when a leg in trouble swings backward with the swinging of a leg in good condition, assists the swinging of the leg in trouble using the generated torque, and requires no actuator such as an electric motor. In addition, the torque generation unit is configured such that an initial compression amount of the compression spring is adjustable and a magnitude of a generated torque is variable.

Both the walking assisting device described in JP 2004-344304 A and the walking rehabilitation device described in JP 2012-125388 A assist the walking motion of a lower limb or a part of the lower limb with the electric motors, but cannot assist the walking motion when power is not continuously supplied from the batteries. In addition, since a user who requires walking assistance does not afford to carry a large and heavy battery, it is assumed that the batteries used in the above devices are relatively small and lightweight. In addition, JP 2004-344304 A and JP 2012-125388 A do not describe any specific configuration that reduces the consumption power of the electric motors. Accordingly, it is assumed that the continuous operation times of the assisting devices described in JP 2004-344304 A and JP 2012-125388 A are relatively short.

The one-leg walking assisting machine described in JP 2013-236741 A generates a torque for swinging a leg through the cam and the compression spring without using an electric motor, and the continuous operation time of the assisting machine is longer than those of the assisting devices described in JP 2004-344304 A and JP 2012-125388 A. However, in accordance with a difference in body type (difference in inertia moment of a lower limb) of each user, a difference in swinging angle of a lower limb of each user, a user's physical condition, a difference in inclination of a walking place, and the like, it is required for a user to adjust the position of a determination portion provided on the compression spring of the torque generation unit with a tool such as a slotted screw driver and adjust an initial compression amount of the compression spring by hand. Therefore, such an operation becomes troublesome for the user.

SUMMARY OF THE INVENTION

The invention provides a swinging joint device, a walking assisting device, a conveying device, a manipulator, and a walking-ability assisting device in which the rigidity of a joint performing swinging motion is automatically adjusted such that a torque generated by the swinging motion is automatically adjusted to further reduce consumption power or a user's load.

An aspect of the invention relates to a swinging joint device including a driving shaft member; a first output portion that swings about a driving axis serving as an axis of the driving shaft member; an elastic body that generates an urging torque corresponding to a first swinging angle that is a swinging angle of the first output portion; an apparent rigidity variable portion that varies apparent rigidity of the elastic body seen from the first output portion; a first angle detection portion that detects the first swinging angle; and a control portion that controls the apparent rigidity variable portion according to the first swinging angle detected by the first angle detection portion to adjust the apparent rigidity of the elastic body seen from the first output portion.

According to the above configuration, the apparent rigidity variable portion is controlled according to the first swinging angle using the control portion. Therefore, since a magnitude of a torque required for assisting swinging motion is automatically adjusted for the swinging motion of a swinging object including the first output portion, the torque can be adjusted without any trouble or effort. In addition, since a torque required for assisting swinging motion is generated using the elastic body, consumption power or a user's load can be further reduced.

In the swinging joint device according to the above aspect, the elastic body may include a flat spiral spring; the apparent rigidity of the elastic body seen from the first output portion may include an apparent spring constant of the flat spiral spring seen from the first output portion; and the apparent rigidity variable portion that varies the apparent rigidity of the elastic body seen from the first output portion may include an apparent spring constant variable portion that varies the apparent spring constant of the flat spiral spring seen from the first output portion.

According to the above configuration, the flat spiral spring is used as the elastic body. For example, when a user's leg is a swinging object, the apparent spring constant (rigidity) seen from the first output portion is appropriately adjusted according to user's action such as walking and running. By adjusting the apparent spring constant (rigidity) seen from the first output portion according to the motion of a swinging object, energy can be smoothly and appropriately reserved in and released from the flat spiral spring.

In the swinging joint device according to the above aspect, a spring fixing member that supports a fixed end of the flat spiral spring may be disposed at a position adjacent to the flat spiral spring; a free end serving as one end of the flat spiral spring may be connected to a spring input shaft member that swings at an angle corresponding to the first swinging angle of the first output portion; the fixed end serving as the other end of the flat spiral spring may be connected to a spring supporting body provided on the spring fixing member at a position distant from the driving axis; and the apparent spring constant variable portion may be constituted by the spring fixing member that is supported so as to be pivotable about the driving axis and is caused to pivot about the driving axis at a prescribed pivoting angle to move a position of the spring supporting body relative to the driving axis about the driving axis by the prescribed pivoting angle, and a rigidity adjustment member that causes the spring fixing member to pivot about the driving axis to vary a position of the fixed end of the flat spiral spring.

According to the above configuration, the apparent spring constant variable portion that adjusts the apparent spring constant of the flat spiral spring can be specifically realized.

In the swinging joint device according to the above aspect, a transmission may be provided between the first output portion and the flat spiral spring; and the transmission may include the spring input shaft member, and when the first output portion swings at the first swinging angle, the spring input shaft member may swing at a swinging angle obtained by changing the first swinging angle based on a prescribed speed ratio.

According to the above configuration, since the swinging angle obtained by amplifying the first swinging angle of the first output portion can be input to the flat spiral spring using the transmission, it becomes possible to use the flat spiral spring having a smaller spring constant. Accordingly, the downsizing of the swinging joint device can be promoted.

In the swinging joint device according to the above aspect, when the position of the spring supporting body, at which the flat spiral spring does not generate the urging torque in a case where the first swinging angle is zero, is set as a reference position, the control portion may control the rigidity adjustment member to adjust a pivoting angle of the spring fixing member to adjust the position of the spring supporting body relative to the reference position according to the first swinging angle of the first output portion, thereby adjusting the apparent spring constant of the flat spiral spring seen from the first output portion.

According to the above configuration, since the apparent spring constant can be adjusted only by controlling the rigidity adjustment member with the control portion so as to cause the spring fixing member to pivot, the apparent spring constant can be easily adjusted.

The swinging joint device according to the above aspect may further include a first driving portion that swings the first output portion about the driving axis based on a control signal from the control portion.

According to the above configuration, the first driving portion swings the first output portion. Therefore, when the swinging joint device is used as, for example, a walking-ability assisting device that supports user's walking or running, a load can be further reduced when a user runs or walks.

The swinging joint device according to the above aspect may further include a second output portion supported so as to be swingable about the driving axis; a second angle detection portion that detects a second swinging angle that is a swinging angle of the second output portion; a second driving portion that swings the second output portion about the driving axis based on a control signal from the control portion; and a swinging link member that is connected to the first output portion and the second output portion and operates based on the first swinging angle of the first output portion and the second swinging angle of the second output portion.

According to the above configuration, when the swinging joint device is used as, for example, a walking-ability assisting device that supports user's walking or running, the first output portion can support the motion of the femoral part of a user and the second output portion can assist the crus part of the user. Therefore, a load can be further reduced when the user walks or runs.

Another aspect of the invention relates to a walking assisting device including the swinging joint device according to the above aspect.

According to the above configuration, it is possible to realize the walking assisting device capable of further reducing a load when a user walks.

Another aspect of the invention relates to a conveying device including the swinging joint device according to the above aspect. The conveying device includes the driving shaft member, a pinion that serves as the first output portion that pivots in a reciprocating manner so as to swing about the driving axis of the driving shaft member, an arm that has a rack portion engaging with the pinion and linearly reciprocates according to a swinging angle that is a reciprocally-pivoting angle of the pinion, the arm being configured to hold and release a workpiece, a pinion driving portion that rotates and drives the pinion, the first angle detection portion that detects the first swinging angle that is the swinging angle of the pinion, the flat spiral spring that accumulates energy when the pinion driving portion rotates and drives the pinion, and rotates and drives the pinion when releasing the accumulated energy, the apparent spring constant variable portion including the spring fixing member and the rigidity adjustment member, and the control portion that controls the pinion driving portion and the rigidity adjustment member; and the conveying device moves the workpiece by linearly reciprocating the arm to hold and release the workpiece.

According to the above configuration, it is possible to realize the conveying device capable of further reducing the consumption power of the pinion driving portion.

Another aspect of the invention relates to a manipulator including the swinging joint device according to the above aspect. The manipulator includes the driving shaft member, a swinging portion serving as the first output portion that swings about the driving axis of the driving shaft member, a swinging portion driving portion that swings the swinging portion, the first angle detection portion that detects the first swinging angle that is a swinging angle of the swinging portion, the flat spiral spring that accumulates energy when the swinging portion driving portion swings the swinging portion, and swings the swinging portion when releasing the accumulated energy, the apparent spring constant variable portion including the spring fixing member and the rigidity adjustment member, and the control portion that controls the swinging portion driving portion and the rigidity adjustment member.

According to the above configuration, it is possible to realize the manipulator capable of further reducing the consumption power of the swinging portion driving portion.

Another aspect of the invention relates to a walking-ability assisting device that applies an assisting force to motion of a lower limb of a user. The walking-ability assisting device includes a waist-side attachment portion attached to a waist-side portion of the user; a first swinging arm that has an elongate shape and is disposed on a lateral side of a femoral part of the user, the first swinging arm having one of a protruding portion and a recessed portion located at an upper portion of the first swinging arm, and the one of the protruding portion and the recessed portion serving as a swinging axis of the first swinging arm; a femoral attachment portion attached to the first swinging arm to be put on the femoral part of the user; a driving shaft member that supports the one of the protruding portion and the recessed portion that serves as the swinging axis of the first swinging arm, the driving shaft member supporting the first swinging arm such that the first swinging arm is swingable in a front-rear direction of the user relative to the waist-side attachment portion; a rigidity variable portion that varies rigidity representing a force required for swinging the first swinging arm swinging about a driving axis serving as an axis of the driving shaft member; and a control portion that controls the rigidity variable portion to control the rigidity of the first swinging arm swinging about the driving axis. The rigidity variable portion is constituted by a flat spiral spring, a spring fixing member, and a rigidity adjustment pivoting member; the flat spiral spring, the spring fixing member, and the rigidity adjustment pivoting member are disposed so as to be coaxial with the driving axis; a spring fixing member that supports a fixed end of the flat spiral spring is disposed at a position adjacent to the flat spiral spring; a free end serving as one end of the flat spiral spring is connected to a spring input shaft member that swings at an angle corresponding to a first swinging angle that is a swinging angle of the first swinging arm; the fixed end serving as the other end of the flat spiral spring is connected to a spring supporting body provided on the spring fixing member at a position distant from the driving axis; and the rigidity adjustment pivoting member adjusts the rigidity by pivoting the spring fixing member about the driving axis to move a position of the fixed end of the flat spiral spring based on a control signal from the control portion.

According to the above configuration, the rigidity variable portion is controlled using the control portion to control rigidity (force required for swinging the first swinging arm) about the driving shaft member. Therefore, since a magnitude of a torque required for assisting swinging motion is automatically adjusted for the swinging motion of a swinging object including the first swinging arm, the torque can be adjusted without any trouble or effort. In addition, since a torque required for assisting swinging motion is generated, consumption power or a user's load can be further reduced. Moreover, the rigidity variable portion can be specifically realized.

In the walking-ability assisting device according the above aspect, a transmission may be provided between the first swinging arm and the flat spiral spring; and the transmission may include the spring input shaft member, and when the first swinging arm swings at the first swinging angle, the spring input shaft member may swing at a swinging angle obtained by changing the first swinging angle based on a prescribed speed ratio.

According to the above configuration, since the swinging angle obtained by amplifying the first swinging angle of the first swinging arm can be input to the flat spiral spring using the transmission, it becomes possible to use the flat spiral spring having a smaller spring constant. Accordingly, the downsizing of the walking-ability assisting device can be promoted.

The walking-ability assisting device according to the above aspect may further include a first angle detection portion that detects the first swinging angle of the first swinging arm. The control portion may control the rigidity adjustment pivoting member to adjust a pivoting angle of the spring fixing member according to the first swinging angle detected by the first angle detection portion, and may adjust an apparent spring constant of the flat spiral spring seen from the first swinging arm, to adjust the rigidity.

According to the above configuration, since the apparent spring constant of the flat spiral spring seen from the first swinging arm can be adjusted only by controlling the rigidity adjustment pivoting member with the control portion so as to pivot the spring fixing member, the apparent spring constant can be easily adjusted.

In the walking-ability assisting device according to the above aspect, the control portion may adjust the pivoting angle of the spring fixing member such that a resonance frequency of the flat spiral spring coincides with a swinging frequency of a swinging object, based on the swinging frequency and the first swinging angle of the first swinging arm about the driving axis, an inertia moment about the driving axis in the swinging object including the first swinging arm, and a spring constant of the flat spiral spring.

According to the above configuration, a pivoting angle of the spring fixing member can be automatically adjusted using the control portion, to an appropriate angle corresponding to a swinging object including the first swinging arm. Accordingly, a generated torque can be automatically adjusted by automatically adjusting the rigidity of a joint that performs swinging motion. In addition, even when the first swinging arm is caused to perform swinging motion by an electric motor, the swinging motion can be assisted at an appropriate torque. Therefore, the consumption power of the electric motor for swinging can be further reduced. Moreover, even when the swinging arm is not caused to swing by the electric motor but is caused to swing by a user himself/herself, the swinging motion can be assisted at an appropriate torque. Therefore, a user's load can be further reduced.

The walking-ability assisting device according to the above aspect may further include a first driving portion that swings the first swinging arm about the driving axis, based on the control signal from the control portion.

According to the above configuration, since the first driving portion swings the first swinging arm, a load can be further reduced when a user walks or runs.

The walking-ability assisting device according to the above aspect may further include a second swinging arm supported so as to be swingable about the driving axis; a second angle detection portion that detects a second swinging angle that is a swinging angle of the second swinging arm; a second driving portion that swings the second swinging arm about the driving axis, based on the control signal from the control portion; a swinging link member that is connected to the first swinging arm and the second swinging arm and operates based on the first swinging angle of the first swinging arm and the second swinging angle of the second swinging arm; and a crus attachment portion attached to the second swinging arm to be put on a crus part of the user.

According to the above configuration, since the first swinging arm can assist the motion of the femoral part of a user and the second swinging arm can assist the motion of the crus part of the user, a load can be further reduced when the user walks or runs.

Another aspect of the invention relates to a swinging joint device including a driving shaft member; a first swinging arm supported so as to be swingable about a driving axis serving as an axis of the driving shaft member; a flat spiral spring that generates an urging torque corresponding to a first swinging angle that is a swinging angle of the first swinging arm; an apparent spring constant variable portion that varies an apparent spring constant of the flat spiral spring seen from the first swinging arm; a first angle detection portion that detects the first swinging angle; and a control portion that controls the apparent spring constant variable portion according to the first swinging angle detected by the first angle detection portion. The apparent spring constant variable portion is a transmission portion in which a speed ratio is adjustable, the apparent spring constant variable portion is disposed in a swinging angle transmission path through which the first swinging angle of the first swinging arm is transmitted to the flat spiral spring, and the apparent spring constant variable portion converts the first swinging angle of the first swinging arm into a spring swinging angle corresponding to the speed ratio adjusted by the control portion, and transmits the spring swinging angle to the flat spiral spring; and the control portion adjusts the speed ratio of the transmission portion according to the first swinging angle to adjust the apparent spring constant of the flat spiral spring seen from the first swinging arm.

According to the above configuration, the apparent spring constant variable portion is controlled according to the first swinging angle using the control portion. Therefore, since a magnitude of a torque required for assisting swinging motion is automatically adjusted for the swinging motion of a swinging object including the first swinging arm, the torque can be adjusted without any trouble or effort. In addition, since a torque required for assisting swinging motion is generated using the flat spiral spring, consumption power or a user's load can be further reduced. In addition, the apparent spring constant of the flat spiral spring seen from the first swinging arm can be easily changed only by adjusting the speed ratio of the transmission portion with the control portion. Moreover, since the swinging angle obtained by amplifying the first swinging angle of the first swinging arm can be input to the flat spiral spring using the transmission portion, it becomes possible to use the flat spiral spring having a smaller spring constant. Accordingly, the downsizing of the swinging joint device may be promoted.

In the swinging joint device according to the above aspect, a spring supporting body that supports a fixed end of the flat spiral spring may be disposed at a position adjacent to the flat spiral spring; the transmission portion may have two input/output shafts; when the input/output shaft on one side is caused to swing at a prescribed swinging angle, the input/output shaft on another side may swing at a swinging angle obtained by multiplying the prescribed swinging angle by n representing the adjusted speed ratio; when the input/output shaft on the other side is caused to swing at the prescribed swinging angle, the input/output shaft on the one side may swing at a swinging angle obtained by multiplying the prescribed swinging angle by 1/n; the input/output shaft on the one side may be connected to the first swinging arm; and the input/output shaft on the other side may be connected to a free end of the flat spiral spring.

According to the above configuration, an appropriate swinging angle can be input to the flat spiral spring using the appropriate transmission portion. In addition, an urging torque of the flat spiral spring can be appropriately transmitted to the first swinging arm. Accordingly, a torque generated by swinging motion can be automatically adjusted using the transmission portion.

In the swinging joint device according to the above aspect, the transmission portion may be constituted by a speed ratio adjustment motor that adjusts the speed ratio based on a control signal from the control portion, and a transmission that has the two input/output shafts; and the speed ratio of the transmission may be adjusted by the speed ratio adjustment motor.

According to the above configuration, the transmission portion can be appropriately realized using the speed ratio adjustment motor and the transmission. Accordingly, the automatic adjustment of a torque generated by swinging motion can be appropriately realized.

The swinging joint device according to the above aspect may further include a first driving portion that swings the first swinging arm about the driving axis, based on a control signal from the control portion.

According to the above configuration, the first driving portion swings the first swinging arm. Therefore, when the swinging joint device is used as, for example, a walking-ability assisting device that assists user's walking or running, a load can be further reduced when a user walks or runs.

The swinging joint device according to the above aspect may further include a second swinging arm supported so as to be swingable about the driving axis; a second angle detection portion that detects a second swinging angle that is a swinging angle of the second swinging arm; a second driving portion that swings the second swinging arm about the driving axis, based on the control signal from the control portion; and a swinging link member that is connected to the first swinging arm and the second swinging arm and operates based on the first swinging angle of the first swinging arm and the second swinging angle of the second swinging arm.

According to the above configuration, when the swinging joint device is used as, for example, a walking-ability assisting device that assists user's walking or running, the first swinging arm can assist the motion of the femoral part of a user and the second swinging arm can assist the motion of the ems part of the user. Therefore, a load can be further reduced when the user walks or runs.

BRIEF DESCRIPTION OF THE DRAWINGS

Features, advantages, and technical and industrial significance of exemplary embodiments of the invention will be described below with reference to the accompanying drawings, in which like numerals denote like elements, and wherein:

FIG. 26 is a flowchart illustrating an example of the processing procedure performed by the control portion.

DETAILED DESCRIPTION OF EMBODIMENTS

Figure 1:
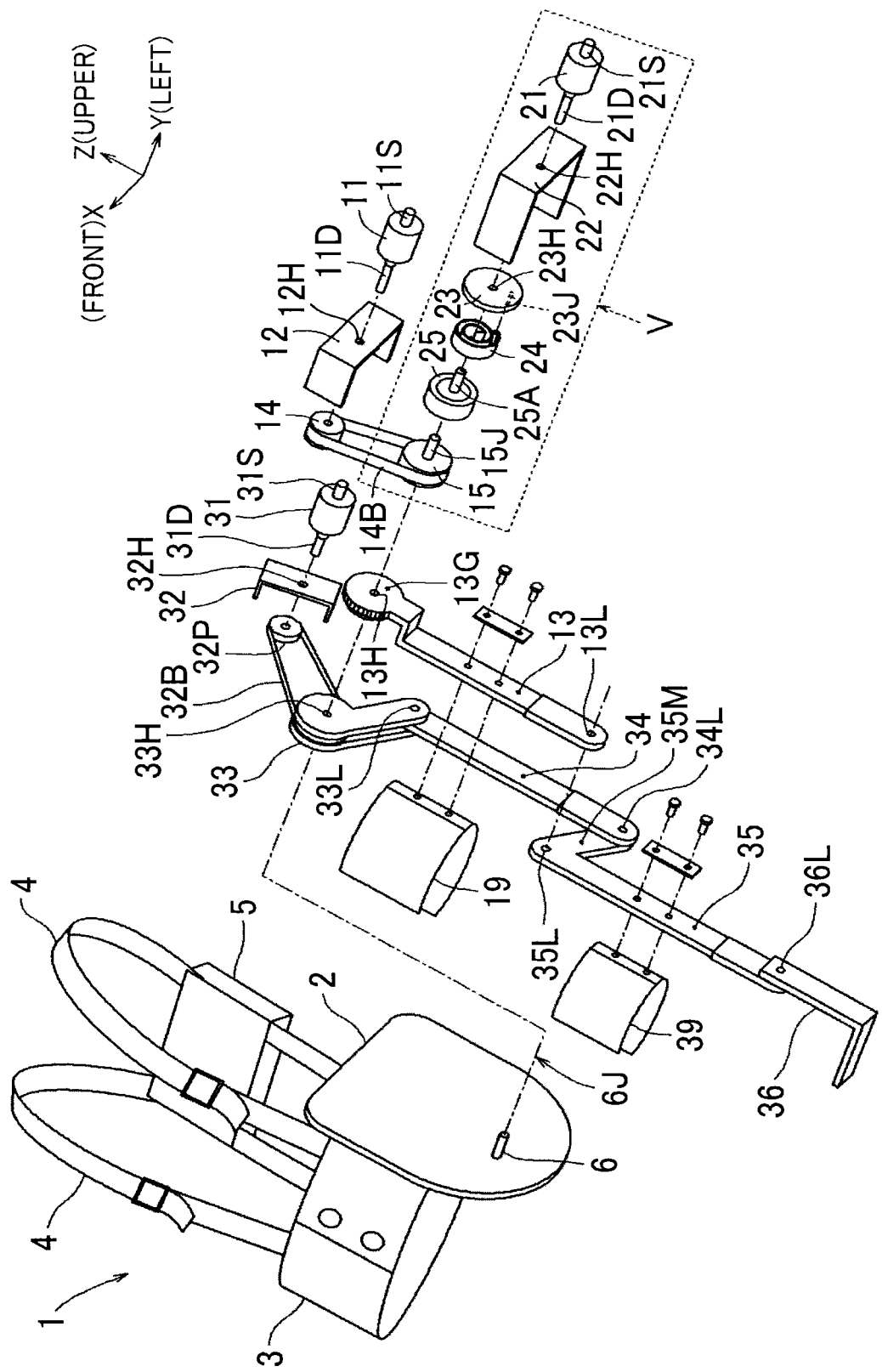
FIG. 1 is an exploded perspective view illustrating the schematic shapes and the assembling positions of respective constituents constituting a swinging joint device of a first embodiment.

Hereinafter, a description will be given, with reference to the drawings, of a first embodiment as an embodiment for carrying out the invention. Note that when respective figures describe X, Y, and Z axes, the X, Y, and Z axes are orthogonal to each other. Unless otherwise stated, a Z-axis direction indicates a vertically-upward direction, an X-axis direction indicates a front direction relative to a user (user wearing a swinging joint device), and a Y-axis direction indicates a left direction relative to the user. Note that in the specification, a "femoral swinging arm 13" shown in FIG. 1 corresponds to a "first output portion" and a "first swinging arm", and a "crus swinging arm 33" shown in FIG. 1 corresponds to a "second output portion" and a "second swinging arm." In addition, a "rotation angle detection portion 11S" shown in FIG. 1 corresponds to a "first angle detection portion," and a "rotation angle detection portion 31S" shown in FIG. 1 corresponds to a "second angle detection portion." Moreover, an "electric motor 11" shown in FIG. 1 corresponds to a "first driving portion," an "electric motor 31" shown in FIG. 1 corresponds to a "second driving portion," and an "electric motor 21" shown in FIG. 1 corresponds to a "rigidity adjustment member" and a "rigidity adjustment pivoting member." Further, in an example of the following description, a driving shaft member 6 is a protruding member. However, the driving shaft member 6 may be a protruding shaft or a recessed (hole-shaped) portion that supports a shaft. Alternatively, the driving shaft member 6 may support a protruding shaft, or a recessed (hole-shaped) portion. Accordingly, when the description says "about the driving shaft member 6," it indicates "about a driving axis line 6J representing the central axis of the driving shaft member 6." Note that a "driving axis line 6J" corresponds to a "driving axis." Furthermore, a "shaft 25A" of a transmission 25 corresponds to a "spring input shaft member." Furthermore, a "spring fixing member 23" and the "electric motor 21" correspond to an "apparent spring constant variable portion." Furthermore, a "flat spiral spring 24," the "spring fixing member 23," and the "electric motor 21" correspond to a "rigidity variable portion." "Rigidity" indicates a torque per unit angle displacement required for swinging the femoral swinging arm 13. Furthermore, a "crus relaying arm 34" and a "crus arm 35" correspond to a "swinging link member." Furthermore, "a base portion 2" corresponds to a "waist-side attachment portion." Furthermore, a "swinging joint device" described in each of first to fourth embodiments corresponds to a "walking assisting device" or a "walking-ability assisting device."

Figure 2:
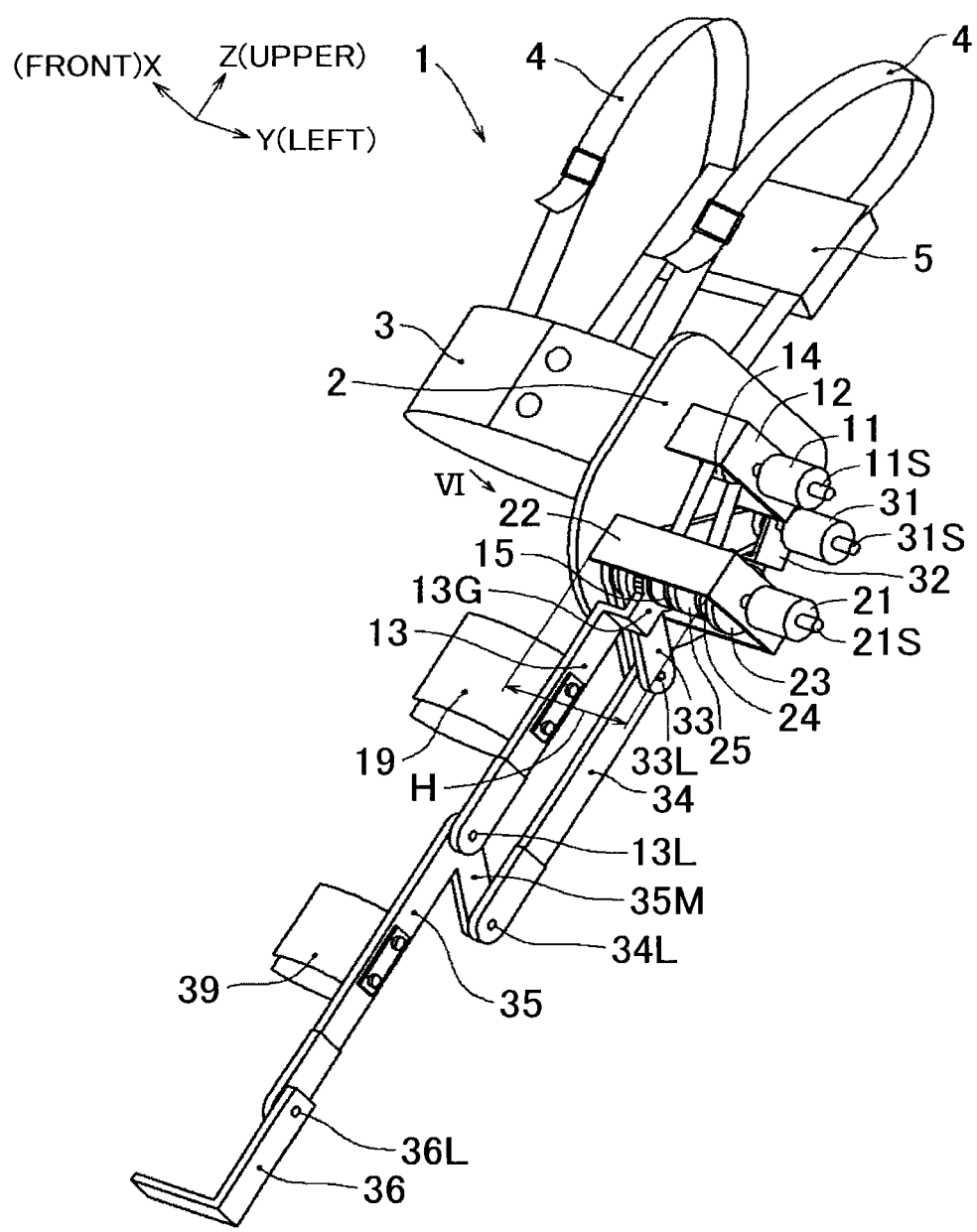
FIG. 2 is a perspective view of the swinging joint device in which the constituents shown in FIG. 1 are assembled together.
Figure 3:
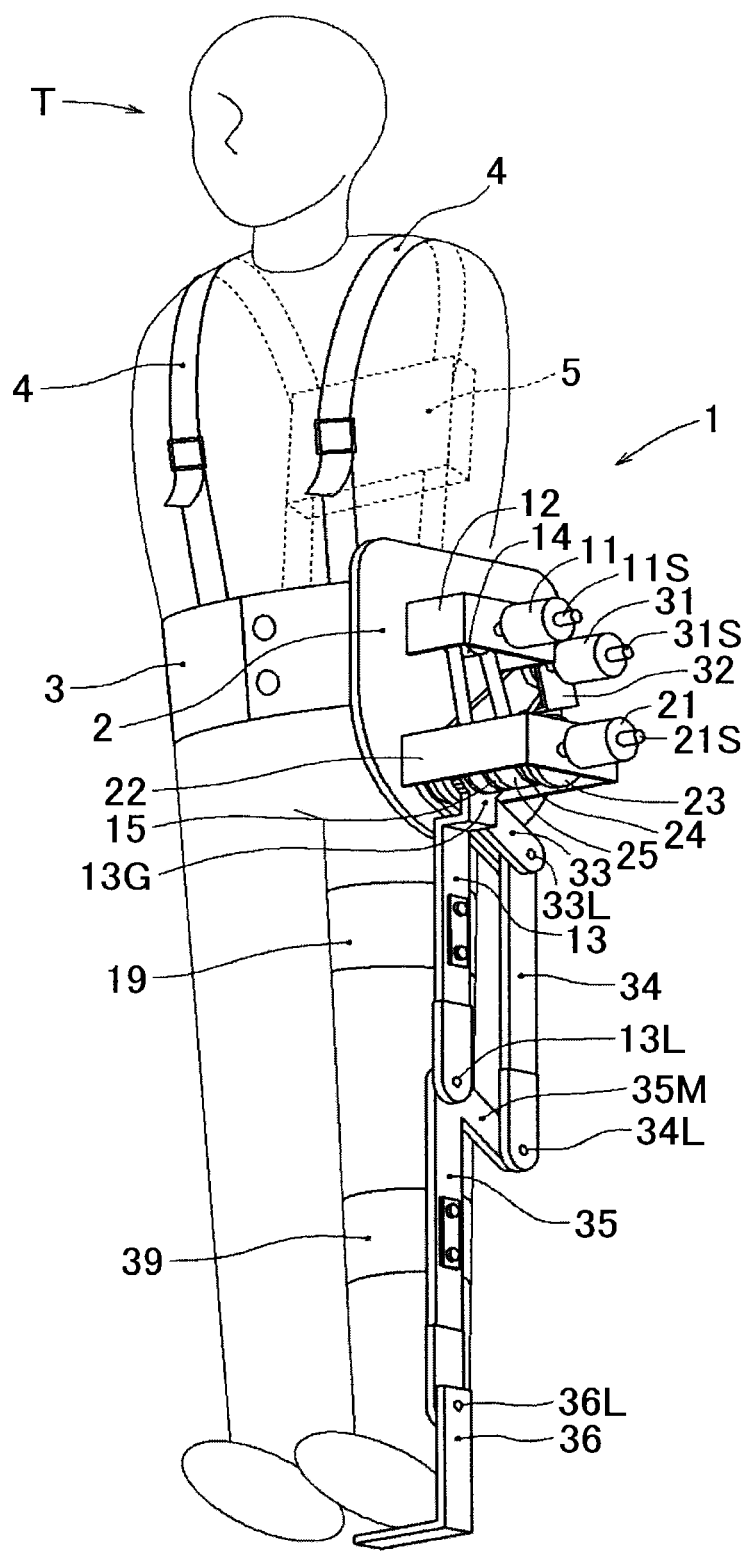
FIG. 3 is a view illustrating a state in which the swinging joint device shown in FIG. 2 is attached to a user (whose arms are omitted)
Figure 4:
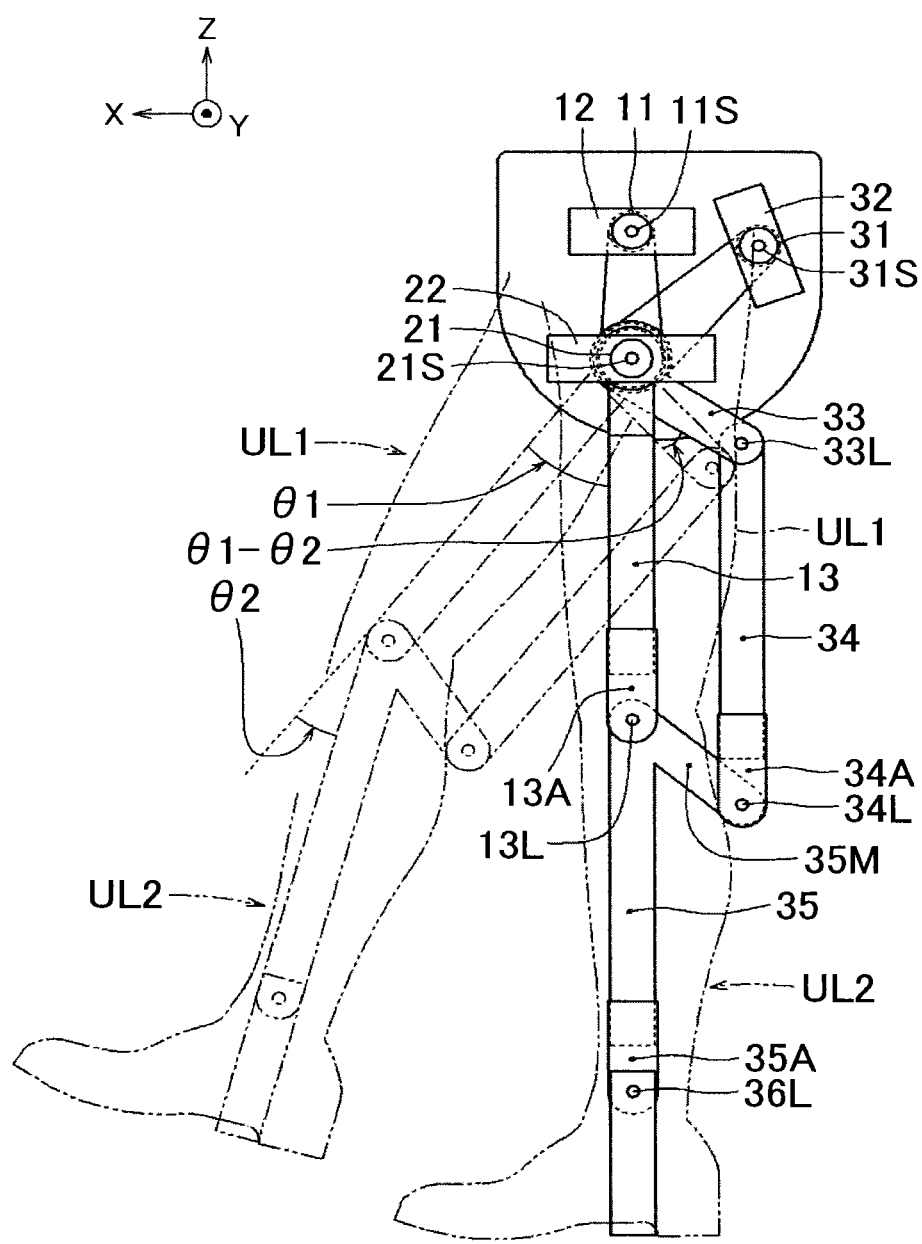
FIG. 4 is a view illustrating a swinging state of a femoral swinging arm (first swinging arm) and a swinging example of a crus arm (second swinging arm)

Hereinafter, a description will be given of the entire configuration (FIGS. 1 to 4) of a swinging joint device 1 of the first embodiment. The swinging joint device 1 of the first embodiment is attached to one leg (the left leg in the first embodiment) of a user to assist a user's action such as walking and running. As shown in FIG. 1, the swinging joint device 1 is constituted by a user attachment portion indicated by symbols 2, 3, 4, 5, 6, and the like, a femoral swinging portion indicated by symbols 11, 12, 14, 14B, 15, 13, 19, and the like, a rigidity adjustment portion indicated by symbols 21, 22, 23, 24, 25, and the like, and a crus swinging portion indicated by symbols 31, 32, 32P, 32B, 33, 34, 35, 36, 39, and the like. Note that FIG. 1 is an exploded perspective view showing the shapes, the assembling positions, and the like of the respective constituents of the swinging joint device 1, and FIG. 2 shows the swinging joint device 1 in a state in which the constituents are assembled together. In addition, FIG. 3 shows a state in which a user wears the swinging joint device 1, and FIG. 4 shows a swinging example of the femoral swinging arm 13 and the crus swinging arm 33.

Hereinafter, a description will be given of the user attachment portion (FIGS. 1 to 4) constituted by a base portion 2, a waist attachment portion 3, shoulder belts 4, a control unit 5, a driving shaft member 6, and the like. The base portion 2 is a member that is fixed to the waist attachment portion 3 and serves as a base (board) for holding the femoral swinging portion, the rigidity adjustment portion, and the crus swinging portion. In addition, a driving shaft member 6 is attached to the base portion 2. The driving shaft member 6 extends in substantially parallel with the Y axis and is located at a position corresponding to the lateral side of the hip joint of a user wearing the swinging joint device 1. Note that the driving shaft member 6 is inserted into a through-hole 33H of the crus swinging arm 33 that will be described later, and then inserted into a through-hole 13H of the femoral swinging arm 13. Note that the driving axis line 6J indicates the central axis of the driving shaft member 6.

The waist attachment portion 3 is a member wound on and fixed to the waist of a user and configured to be adjustable according to a size of the waist of the user. In addition, the waist attachment portion 3 is fixed to the base portion 2 and connected to one and the other ends of shoulder belts 4.

The shoulder belts 4 are connected to the front-surface side and the back-surface side of the waist attachment portion 3 at their ends (one and the other ends), configured to be capable of adjusting their lengths, and attached to the control unit 5. A user can carry the control unit 5 on his/her back like a backpack by adjusting lengths of the shoulder belts 4 and putting the shoulder belts 4 on his/her shoulders.

The control unit 5 accommodates a control portion that controls the electric motors 11, 21, and 31, a battery that supplies power to the control portion and the electric motors 11, 21, 31, and the like. Note that the control portion will be described later using FIG. 12.

Hereinafter, a description will be given of the femoral swinging portion (FIGS. 1 to 4) constituted by the electric motor 11, a bracket 12, a pulley 14, a belt 14B, a pulley 15, the femoral swinging arm 13, a femoral attachment portion 19, and the like. The femoral swinging arm 13 is constituted by a disc portion 13G and an arm portion extending downward from the disc portion 13G. The disc portion 13G has a through-hole 13H at its center, and the driving shaft member 6 is inserted into the through-hole 13H. Accordingly, the femoral swinging arm 13 is swingably supported about the driving shaft member 6. In addition, the through-hole 13H of the femoral swinging arm 13 is disposed at a position corresponding to the lateral side of the hip joint of a user, and a link hole 13L provided at the lower end of the femoral swinging arm 13 is disposed at a position corresponding to the lateral side of the knee joint of the user. Note that a downwardly-extending length of the femoral swinging arm 13 is configured to be adjustable, and a user is capable of adjusting a vertical position of the link hole 13L according to a position of his/her knee joint. In addition, the femoral swinging arm 13 is attached to a femoral attachment portion 19. The femoral attachment portion 19 is put on the femoral part (the circumference of the thigh) of a user to facilitate the attachment of the femoral swinging arm 13 to the femoral part of the user. Moreover, the pulley 15 is fixed to the disc portion 13G and integrally swings with the femoral swinging arm 13. Accordingly, a pulley shaft member 15J of the pulley 15 swings about the driving axis line 6J at the same angle as a swinging angle of the femoral swinging arm 13. Further, a belt 14B is put between the pulley 15 and a pulley 14 that will be described later, and the swinging power of the electric motor 11 is transmitted to the pulley 15 via the pulley 14 and the belt 14B to swing the femoral swinging arm 13.

A bracket 12 is a member for fixing the electric motor 11 to a base portion 2 and fixed to the base portion 2. The bracket 12 has a through-hole 12H into which the rotation shaft of the electric motor 11 is inserted, and the bracket 12 is fixed to the base portion 2. Note that the bracket 12 is fixed to the base portion 2 after the rotation shaft of the electric motor 11 is inserted into the through-hole 12H of the bracket 12 and the pulley 14 is attached to the inserted rotation shaft.

A speed reducer 11D is attached to a distal end of the electric motor 11, and the speed reducer 11D is inserted into the through-hole 12H of the bracket 12 to be attached to the pulley 14. In addition, the electric motor 11 is fixed to the bracket 12. Moreover, the electric motor 11 receives power and driving signals from the battery and the control portion accommodated in the control unit 5. Then, the electric motor 11 can swing the femoral swinging arm 13 in a front-rear direction about the driving shaft member 6 relative to the bracket 12 (i.e., the base portion 2) (see FIG. 4). Further, the electric motor 11 is provided with the rotation angle detection portion 11S such as an encoder. The rotation angle detection portion 11S outputs a signal corresponding to a rotation angle of the shaft of the electric motor 11, to the control portion. The control portion is capable of detecting a rotation angle of the speed reducer 11D based on a detection signal from the rotation angle detection portion 11S, a speed reduction ratio of the speed reducer 11D, and a pulley ratio between the pulley 14 and the pulley 15, and capable of detecting a swinging angle of the femoral swinging arm 13. Note that the bracket 22 (see FIG. 1) or the base portion 2 may be provided with an angle detection portion (angular sensor) that detects a swinging angle of the femoral swinging arm 13 relative to the base portion 2, and the bracket 22 or the base portion 2 may be provided with an angle detection portion (angular sensor) that detects a swinging angle of the crus swinging arm 33 relative to the base portion 2. Note that the electric motor 11 is a motor capable of idling. When the electric motor 11 receives a swinging force from the femoral swinging arm 13 in its non-energized state, the speed reducer 11D pivots and the rotation angle detection portion 11S outputs a signal corresponding to a pivoting angle of the speed reducer 11D.

Hereinafter, a description will be given of the crus swinging portion (FIGS. 1 to 4) constituted by the electric motor 31, the bracket 32, power transmission portions (32P and 32B), the crus swinging arm 33, a crus relaying arm 34, a crus arm 35, a foot holding portion 36, a crus attachment portion 39, and the like. The crus swinging arm 33 has the through-hole 33H into which the driving shaft member 6 is inserted. When the driving shaft member 6 is inserted into the through-hole 33H, the crus swinging arm 33 is swingably supported about the driving shaft member 6. A belt 32B is put on the crus swinging arm 33, and power is transmitted from a power transmission portion constituted by the electric motor 31, a pulley 32P, and a belt 32B to swing the crus swinging arm 33 about the driving shaft member 6.

The crus relaying arm 34 has an upper end swingably connected to the distal end of the crus swinging arm 33 and a lower end swingably connected to the end of a parallel link forming portion 35M on the upper-end side of the crus arm 35. Note that a downwardly-extending length of the crus relaying arm 34 is configured to be adjustable. That is, a length of the crus relaying arm 34 is adjusted according to an adjusted length of the femoral swinging arm 13.

The crus arm 35 is formed into a substantially reverse L-shape and has a link hole 35L, which is connected to the link hole 13L at the lower end of the femoral swinging arm 13, at a position corresponding to a bending portion of the L-shape. Accordingly, the crus arm 35 is formed such that one end of the parallel link forming portion 35M on an upper-end side is swingably connected to the lower end of the crus relaying arm 34 and the other end of the parallel link forming portion 35M is swingably connected to the lower end of the femoral swinging arm 13. In addition, the crus arm 35 has a lower end to which the upper end of the foot holding portion 36 is swingably connected. Note that a downwardly-extending length of the crus arm 35 is configured to be adjustable so as to match the crus part of a user. In addition, the foot holding portion 36 is formed into a substantially L-shape and has a lower end positioned at the bottom of the foot of a user. Moreover, the crus arm 35 is attached to a crus attachment portion 39. The crus attachment portion 39 is put on the crus part (the circumference of the calf) of a user to facilitate the attachment of the crus arm 35 to the crus part of the user.

The bracket 32 is a member for fixing the electric motor 31 to the base portion 2, and the bracket 32 is fixed to the base portion 2. In addition, the bracket 32 has a through-hole 32H.

A speed reducer 31D is attached to the distal end of the electric motor 31, and the speed reducer 31D is inserted into the through-hole 32H of the bracket 32. In addition, the speed reducer 31D is attached to the pulley 32P, and the belt 32B is disposed on the pulley 32P and the crus swinging arm 33. Moreover, the electric motor 31 receives power and driving signals from the battery and the control portion accommodated in the control unit 5. Then, the electric motor 31 can swing the crus swinging arm 33 in the front-rear direction about the driving shaft member 6 via the pulley 32P and the belt 32B (see FIG. 4). Further, the electric motor 31 is provided with the rotation angle detection portion 31S such as an encoder. The rotation angle detection portion 31S outputs a signal corresponding to a rotation angle of the shaft of the electric motor 31, to the control portion. The control portion is capable of detecting a rotation angle of the crus swinging arm 33 based on a detection signal from the rotation angle detection portion 31S, a speed reduction ratio of the speed reducer 31D, and a pulley ratio, and is capable of detecting a swinging angle of the crus swinging arm 33. Note that the electric motor 31 is a motor capable of idling. When the electric motor 31 receives a swinging force from the femoral swinging arm 33 in its non-energized state, the speed reducer 31D pivots and the rotation angle detection portion 31S outputs a signal corresponding to a pivoting angle of the speed reducer 11D.

Next, a description will be given, with reference to FIG. 4, of the operation of assisting the swinging of a femoral part UL1 of a user wearing the femoral swinging arm 13 and the operation of assisting the swinging of a crus part UL2 of the user wearing the crus arm 35. The femoral swinging arm 13 swings about the driving shaft member 6 when receiving power from the electric motor 11. Similarly, the crus swinging arm 33 swings about the driving shaft member 6 when receiving power from the electric motor 31. In addition, the femoral swinging arm 13, the crus swinging arm 33, the ems relaying arm 34, and the parallel link forming portion 35M (of the crus arm 35) constitute a parallel link formed into a parallelogram. Accordingly, the ems relaying arm 34 and the ems arm 35 correspond to swinging link members that are connected to the femoral swinging arm 13 and the ems swinging arm 33 and operate based on a swinging angle (angle $\theta1$ in FIG. 4) of the femoral swinging arm 13 and a swinging angle (angle $\theta1 - \theta2$ in FIG. 4) of the crus swinging arm 33. Note that the positions of the femoral swinging arm 13, the crus swinging arm 33, the crus relaying arm 34, and the crus arm 35 indicated by solid lines in FIG. 4 are set as the initial positions (positions where a user is at a standstill in his/her upright posture) of the respective arms.

When the femoral swinging arm 13 swings forward at the angle $\theta1$ from its initial position, the femoral part UL1 of a user can swing forward at the angle $\theta1$ as shown in FIG. 4. At the same time, when the crus swinging arm 33 swings forward at the angle ($\theta1-\theta2$) from its initial position, the crus part UL2 of the user can swing forward so as to tilt at the angle $\theta2$ relative to the femoral swinging arm 13 as shown in FIG. 4. Since the swinging motion of the femoral swinging arm 13 with the electric motor 11 and the swinging motion of the crus swinging arm 33 with the electric motor 31 can be separately controlled, the user is allowed to freely adjust the angle $\theta1$ and the angle $\theta2$ as he/she wants. In addition, since the swinging of the femoral part that requires a large torque can be performed using both torques of the electric motors 11 and 31 according to the configuration, a large motor is not required.

In addition, when the femoral swinging arm 13 swings, the energy of the swinging motion is accumulated in the flat spiral spring 24 and used to perform swinging motion in an opposite direction. That is, energy generated when the femoral swinging arm 13 swings forward is accumulated in the flat spiral spring 24 and used when the femoral swinging arm 13 swings backward, and energy generated when the femoral swinging arm 13 swings backward is accumulated in the flat spiral spring 24 and used when the femoral swinging arm 13 swings forward. Next, a description will be given of the rigidity adjustment portion including the flat spiral spring 24.

Hereinafter, a description will be given of the rigidity adjustment portion (FIGS. 1 to 3 and FIGS. 5 to 7) constituted by the electric motor 21, the bracket 22, the spring fixing member 23, the flat spiral spring 24, the transmission 25, and the like. The bracket 22 is a member that fixes the electric motor 21 to the base portion 2 and is fixed to the base portion 2. The bracket 22 has a through-hole 22H into which the rotation shaft of the electric motor 21 is inserted. In addition, as shown in FIGS. 1 and 6, the through-hole 13H of the disc portion 13G of the femoral swinging arm 13, the pulley shaft member 15J of the pulley 15, the shaft 25A of the transmission 25, the central axis of the flat spiral spring 24, a through-hole 23H of the spring fixing member 23, the through-hole 22H of the bracket 22, and the speed reducer 21D of the electric motor 21 are disposed to be coaxial with the driving axis line 6J.

Figure 5:
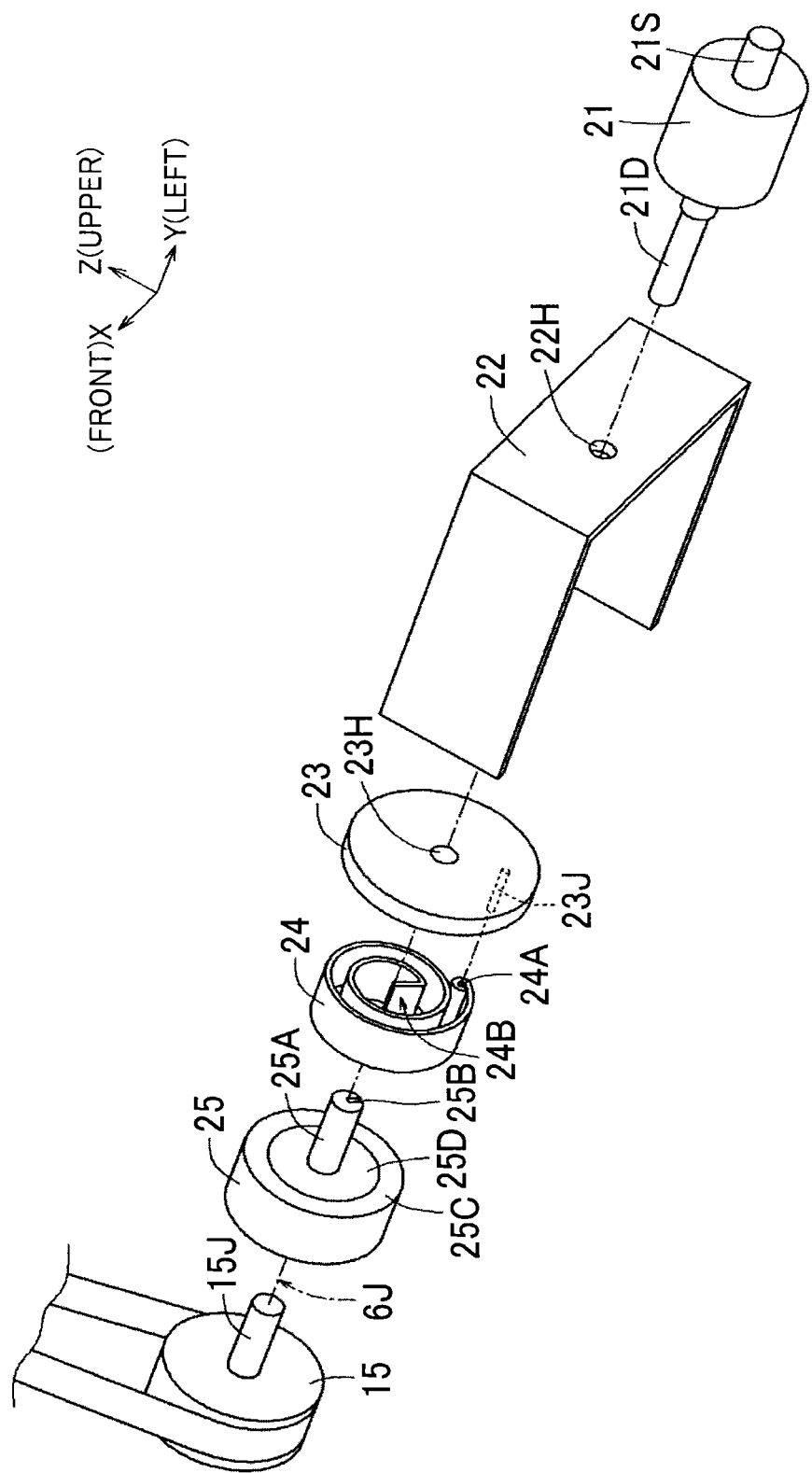
FIG. 5 is an enlarged view of a V part in FIG. 1 and an exploded perspective view illustrating the configurations of a flat spiral spring and an apparent spring constant variable portion.
Figure 6:
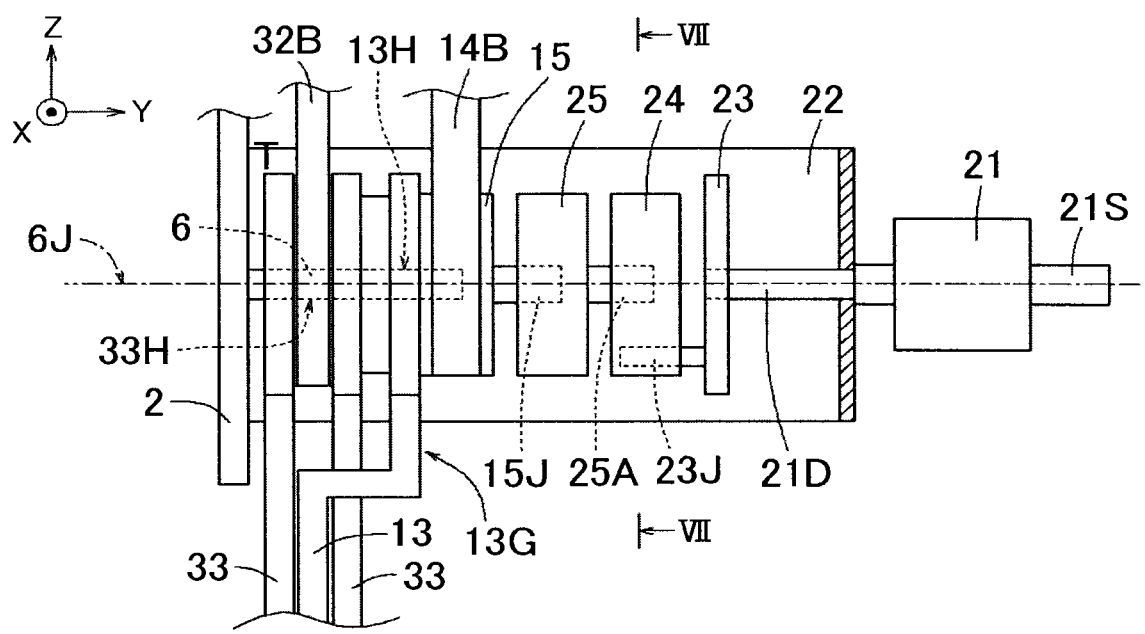
FIG. 6 is a view seen from a VI direction in FIG. 2 and a view illustrating the arrangements of members provided to be coaxial with a driving axis line of a driving shaft member.
Figure 7:
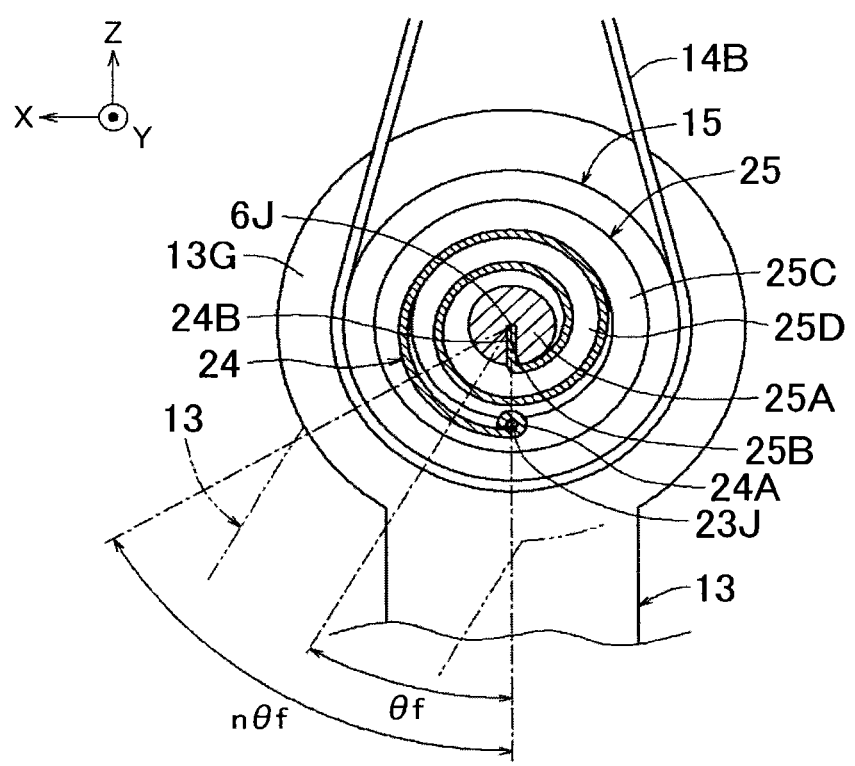
FIG. 7 is a view seen from a VII direction in FIG. 6 and a view illustrating a state in which a swinging angle of an output shaft member of a transmission is amplified at a prescribed speed ratio relative to a first swinging angle of the femoral swinging arm.

As shown in FIG. 5, the transmission 25 is connected via its input portion 25C to the pulley shaft member 15J of the pulley 15 fixed to the disc portion 13G of the femoral swinging arm 13, and outputs an output pivoting angle nθ, which is obtained by multiplying an input pivoting angle θ input to the input portion 25C by n times, as a pivoting angle of the shaft 25A based on a prescribed speed ratio (n). Thus, as shown in FIG. 7, the transmission 25 includes the shaft 25A, and when the femoral swinging arm 13 swings at a first swinging angle (θf), the shaft 25A swings at a swinging angle (nθf) obtained by changing the first swinging angle (θf) based on a prescribed speed ratio (n). In addition, as shown in FIG. 5, the shaft 25A has a spring free-end insertion groove 25B that serves as a groove extending in the direction of the driving axis line 6J for fixing the side of a free end 24B of the flat spiral spring 24. Note that the transmission 25 pivots the pulley shaft member 15J by a pivoting angle θb·(1/n) when the shaft 25A caused to pivot by a pivoting angle θb due to an urging torque from the flat spiral spring 24.

As the flat spiral spring 24, an elastic body such as a spring member is spirally wound about a prescribed axis. As shown in FIG. 5, the flat spiral spring 24 has the free end 24B at one end serving as an end positioned near the central area of its winding and has a fixed end 24A at the other end serving as an end positioned distant from the central area of the winding. Note that the free end 24B is fixed to the spring free-end insertion groove 25B of the shaft 25A and the fixed end 24A is fixed to a spring supporting body 23J of the spring fixing member 23 in FIG. 5.

The spring fixing member 23 has a through-hole 23H into which the speed reducer 21D at the distal end of the electric motor 21 is inserted, is supported by the speed reducer 21D, and is fixed to the base portion 2 by the bracket 22 and the electric motor 21. In addition, the spring fixing member 23 has the spring supporting body 23J, which supports the fixed end 24A of the flat spiral spring 24, on its surface facing the flat spiral spring 24 at a position distant from the driving axis line 6J. For example, the spring supporting body 23J is a shaft-shaped member extending along the direction of the driving axis line 6J and inserted into a cylindrical portion formed at the position of the fixed end 24A of the flat spiral spring 24. Further, the spring fixing member 23 is caused, by the electric motor 21, to pivot about the driving axis line 6J and varies a position of the fixed end 24A of the flat spiral spring 24 in a circumferential direction. As described above, the spring fixing member 23 is supported so as to be pivotable about the driving axis line 6J and pivots at a prescribed pivoting angle about the driving axis line 6J. Thus, the spring fixing member 23 moves a position of the spring supporting body 23J relative to the driving axis line 6J in the circumferential direction by a prescribed pivoting angle about the driving axis line 6J.

The electric motor 21 has the speed reducer 21D at its distal end. In addition, the speed reducer 21D is inserted into the through-hole 22H of the bracket 22, the electric motor 21 is fixed to the bracket 22, and the bracket 22 is fixed to the base portion 2. Moreover, the electric motor 21 receives power and driving signals from the battery and the control portion accommodated in the control unit 5. Further, the electric motor 21 can pivot the spring fixing member 23 about the driving axis line 6J relative to the bracket 22 (i.e., the base portion 2) and move a position of the fixed end 24A of the flat spiral spring 24 in the circumferential direction. Furthermore, the electric motor 21 is provided with the rotation angle detection portion 21S such as an encoder. The rotation angle detection portion 21S outputs a signal corresponding to a rotation angle of the shaft of the electric motor 21, to the control portion. Meanwhile, the control portion is capable of detecting a rotation angle of the speed reducer 21D based on a detection signal from the rotation angle detection portion 21S and a speed reduction ratio of the speed reducer 21D, and is capable of detecting a pivoting angle of the spring fixing member 23. Note that the bracket 22 may be provided with an angle detection portion (angular sensor) that detects a pivoting angle of the spring fixing member 23 relative to the bracket 22. In addition, the electric motor 21 is not an idling motor (that is, the electric motor 21 is a motor that does not idle), a pivoting angle position of the speed reducer 21D is maintained even in its non-energized state, and the position of the fixed end 24A is maintained even when an urging torque is generated in the flat spiral spring 24.

Figure 8:
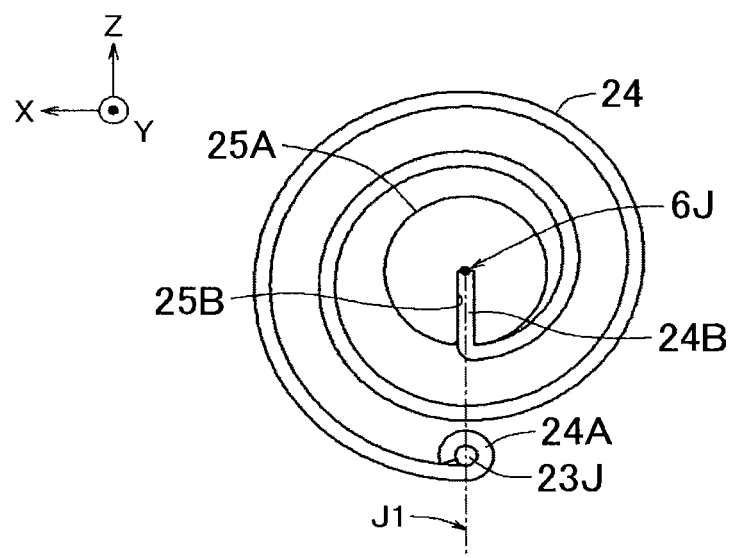
FIG. 8 shows a state in which an urging torque is not generated in the flat spiral spring when a swinging angle of the femoral swinging arm is zero, and is a perspective view showing a reference position of a spring supporting body (i.e., a spring fixing end) relative to the driving axis line.

Hereinafter, a description will be given of the position of the fixed end 24A and an offset angle θs of the flat spiral spring 24 (FIGS. 8 to 11). FIG. 8 shows an example of a case in which a user T shown in FIG. 3 is in his/her upright posture, a swinging angle of the femoral swinging arm 13 is zero, and an urging torque of the flat spiral spring 24 is zero. At the position of the fixed end 24A of the flat spiral spring 24 in the example of FIG. 8, neither an urging torque in a clockwise direction about the driving axis line 6J nor an urging torque in a "counterclockwise" direction about the driving axis line 6J is generated in the free end 24B. Further, a reference line J1 shown in FIG. 8 is a virtual line passing through the driving axis line 6J and the spring free-end insertion groove 25B in a case in which the position of the fixed end 24A is adjusted so as not to generate an urging torque in the free end 24B when a swinging angle of the femoral swinging arm 13 is zero, and indicates a reference pivoting angle position of the shaft 25A. In addition, the position of the fixed end 24A (the spring supporting body 23J) shown in the example of FIG. 8 is set as the reference position of the fixed end 24A (the spring supporting body 23J) of the flat spiral spring 24.

Figure 9:
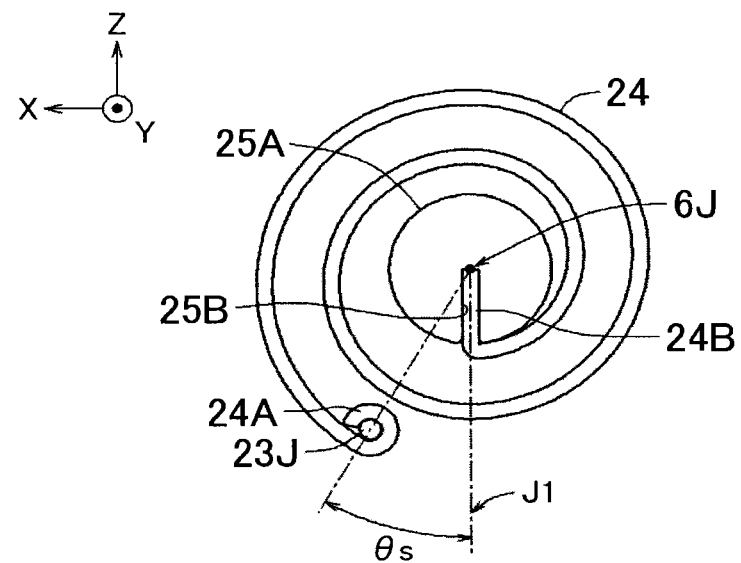
FIG. 9 is a view showing a state transitioned from the state in FIG. 8, the state in FIG. 9 being a state in which the spring fixing member is caused to pivot by a prescribed pivoting angle to move a position of the spring supporting body relative to the driving axis line from the reference position.

FIG. 9 shows a state in which the electric motor 21 is driven to change the position of the fixed end 24A of the flat spiral spring 24 from the state shown in FIG. 8 to a position at which the fixed end 24A of the flat spiral spring 24 is moved clockwise in the circumferential direction by a pivoting angle (θs) from the above reference position. This state is set as a "state in which the offset angle θs in the clockwise direction is imparted to the flat spiral spring 24." In this state, even when the user is in his/her upright posture and a swinging angle of the femoral swinging arm 13 is zero, an urging torque of the flat spiral spring 24 is applied to the shaft 25A due to the offset angle θs in the clockwise direction, and the urging torque is applied from the shaft 25A to the femoral swinging arm 13 via the transmission 25 and the pulley 15.

Figure 10:
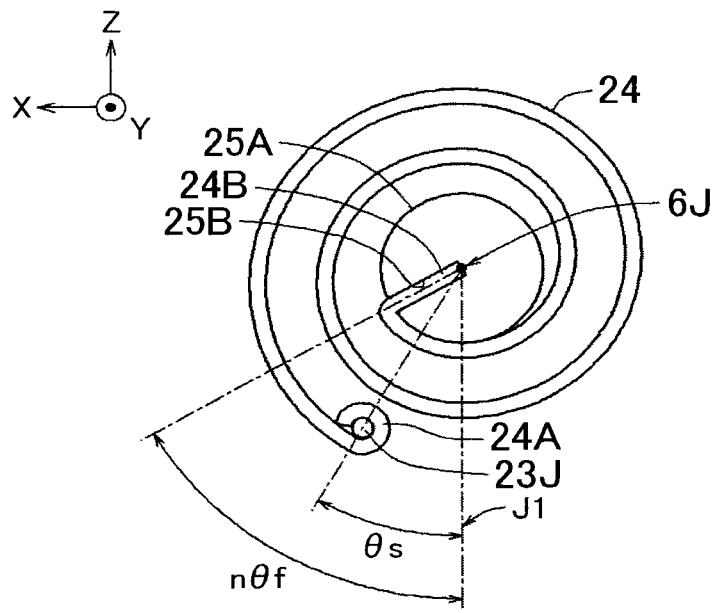
FIG. 10 is a view showing a free end, a fixed end, and portions near the free end and the fixed end in the flat spiral spring when the femoral swinging arm swings forward from the state shown in FIG. 9.

FIG. 10 shows an example of a case in which the femoral swinging arm 13 swings in the clockwise direction at a swinging angle θf in a state in which the "offset angle θs in the clockwise direction" shown in FIG. 9 is imparted. When the femoral swinging arm 13 swings in the clockwise direction at the swinging angle θf with a speed ratio (n) of the transmission 25, the shaft 25A of the transmission 25 swings in the clockwise direction at a swinging angle nθf. That is, in the example shown in FIG. 10, an urging torque in the "counterclockwise" direction is generated in the flat spiral spring 24 according to an angle (nθf−θs) obtained by subtracting the offset angle θs from the swinging angle nθf.

Figure 11:
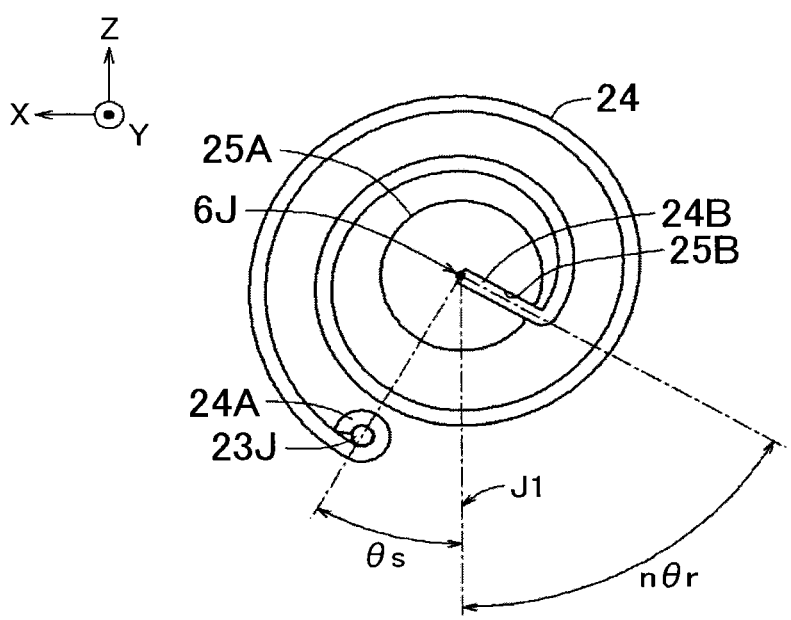
FIG. 11 is a view showing the free end, the fixed end, and the portions near the free end and the fixed end in the flat spiral spring when the femoral swinging arm swings backward from the state shown in FIG. 9.

FIG. 11 shows an example of a case in which the femoral swinging arm 13 swings in the "counterclockwise" direction at a swinging angle θr in a state in which the "offset angle θs in the clockwise direction" shown in FIG. 9 is imparted. When the femoral swinging arm 13 swings in the "counterclockwise" direction at the swinging angle θr with a speed ratio (n) of the transmission 25, the shaft 25A of the transmission 25 swings in the "counterclockwise" direction at a swinging angle nθr. That is, in the example shown in FIG. 11, an urging torque in the clockwise direction is generated in the flat spiral spring 24 according to an angle (nθr+θs) obtained by adding the offset angle θs to the swinging angle nθr. By the transmission 25 (that may be omitted), the flat spiral spring 24, the spring fixing member 23, and the electric motor 21 (the rigidity adjustment member) described above, an apparent spring constant variable portion that varies an apparent spring constant seen from the femoral swinging arm 13 is constituted. Further, the apparent spring constant variable portion varies rigidity about the driving axis line 6J. As described above, the "rigidity" indicates a torque per unit angle displacement required for swinging the femoral swinging arm 13, the apparent spring constant of the flat spiral spring 24 seen from the femoral swinging arm 13 is associated with this torque. Accordingly, "apparent rigidity of the elastic body (the flat spiral spring) seen from the femoral swinging arm 13" includes an "apparent spring constant of the flat spiral spring 24 seen from the femoral swinging arm 13." The spring constant is a kind of rigidity. Further, it is possible to vary the rigidity of the elastic body, optimally reserve energy, and optimally release the reserved energy. In addition, the "apparent rigidity variable portion that varies the apparent rigidity of the elastic body seen from the femoral swinging arm 13" includes the "apparent spring constant variable portion that varies the apparent spring constant of the flat spiral spring 24 seen from the femoral swinging arm 13."

Figure 12:
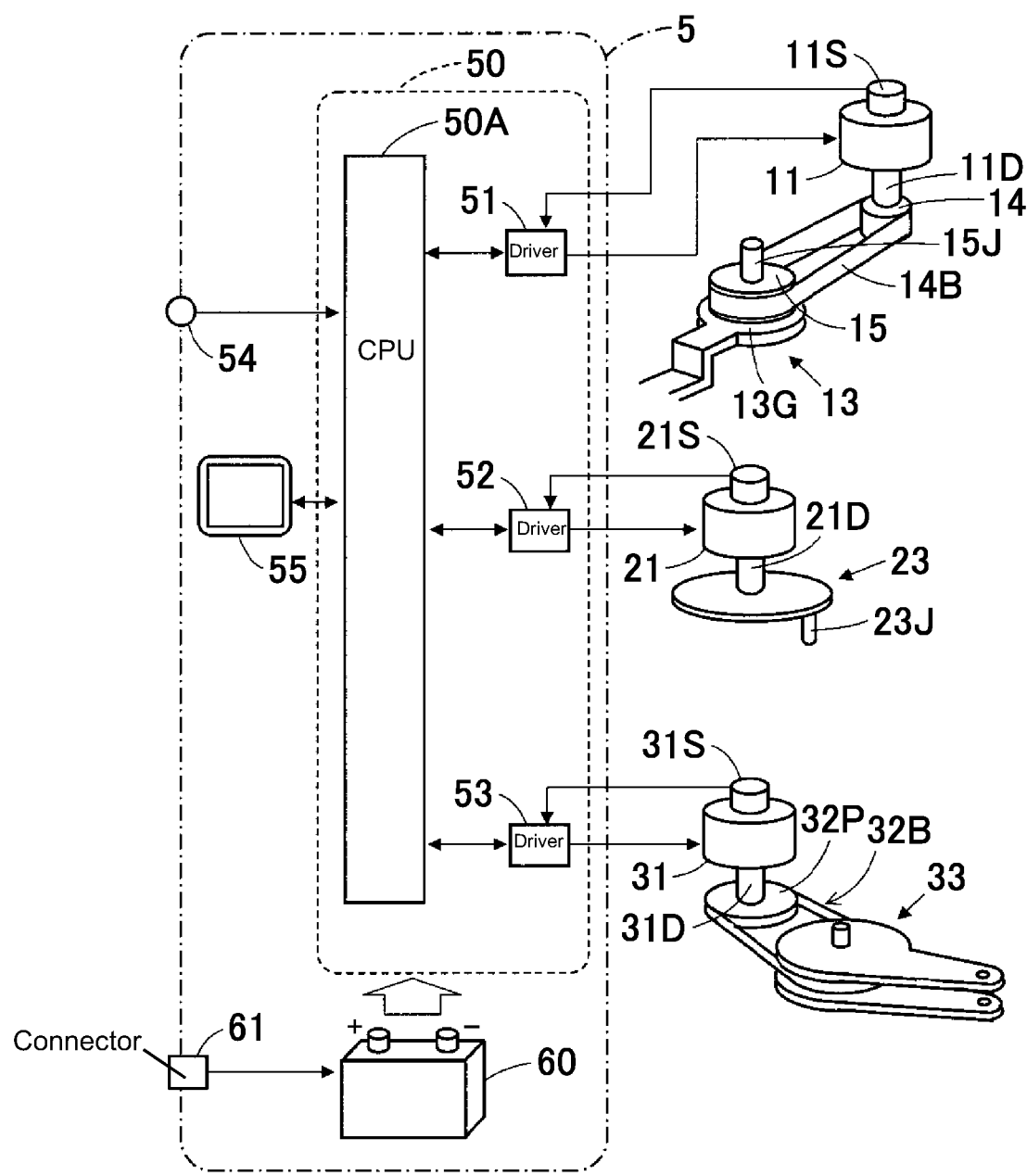
FIG. 12 is a view illustrating the input/output to/from a control portion.

Next, a description will be given of the input/output of a control portion 50 with reference to FIG. 12. The control unit 5 accommodates the control portion 50 and a battery 60. In addition, the control unit 5 includes a start switch 54, a touch panel 55 serving as an input/output portion, a connector 61 for charging the battery 60, and the like. Moreover, the control portion 50 (the control unit) includes a central processing unit (CPU) 50A, motor drivers 51, 52, and 53, and the like. Note that although the control portion 50 also includes a storage unit that stores a program for running the processing of the control portion 50, various measurement results, and the like, the storage unit is not shown in the figure.

As will be described later, the control portion 50 calculates a target swinging cycle and a target swinging angle to swing the femoral swinging arm 13 and outputs a driving signal to the electric motor 11 via the motor driver 51. The electric motor 11 swings the speed reducer 11D based on the driving signal from the control portion 50 and swings the femoral swinging arm 13 at a prescribed cycle and a prescribed angle via the pulley 14, the belt 14B, and the pulley 15. In addition, a rotation speed and a rotation amount of the shaft of the electric motor 11 are detected by the rotation angle detection portion 11S, and a detection signal is input to the CPU 50A via the motor driver 51 while being input to the motor driver 51. The CPU 50A performs feedback control such that an actual swinging cycle and an actual swinging angle of the femoral swinging arm 13 based on the detection signal from the rotation angle detection portion 11S become closer to (i.e., approach) the target swinging cycle and the target swinging angle.

In addition, as will be described later, the control portion 50 calculates a target rigidity adjustment angle as a pivoting angle of the spring fixing member 23 such that the apparent spring constant of the flat spiral spring 24 seen from the femoral swinging arm 13 has an optimum value, and outputs a driving signal to the electric motor 21 via the motor driver 52. Based on the driving signal from the control portion 50, the electric motor 21 pivots the spring fixing member 23 via the speed reducer 21D. In addition, a rotation speed and a rotation amount of the shaft of the electric motor 21 are detected by the rotation angle detection portion 21S, and a detection signal is input to the CPU 50A via the motor driver 52 while being input to the motor driver 52. The CPU 50A performs feedback control such that an actual pivoting angle of the spring fixing member 23 based on the detection signal from the rotation angle detection portion 21S becomes closer to (i.e., approaches) the target rigidity adjustment angle.

As will be described later, the control portion 50 calculates a target swinging cycle and a target swinging angle to swing the crus swinging arm 33 and outputs a driving signal to the electric motor 31 via the motor driver 53. Based on the driving signal from the control portion 50, the electric motor 31 swings the crus swinging arm 33 at a prescribed cycle and a prescribed angle via the speed reducer 31D, the pulley 32P, and the belt 32B. In addition, a rotation speed and a rotation amount of the shaft of the electric motor 31 are detected by the rotation angle detection portion 31S, and a detection signal is input to the CPU 50A via the motor driver 53 while being input to the motor driver 53. The CPU 50A performs feedback control such that an actual swinging cycle and an actual swinging angle of the crus swinging arm 33 based on the detection signal from the rotation angle detection portion 31S become closer to (i.e., approach) the target swinging cycle and the target swinging angle.

The start switch 54 is a switch for starting the control portion 50. In addition, the touch panel 55 is a device that is used to input a user's height, weight, and the like, and that displays a setting state and the like. Moreover, the connector 61 for charging is a connector to which a charging cable is connected to charge the battery 60.

Figure 13:
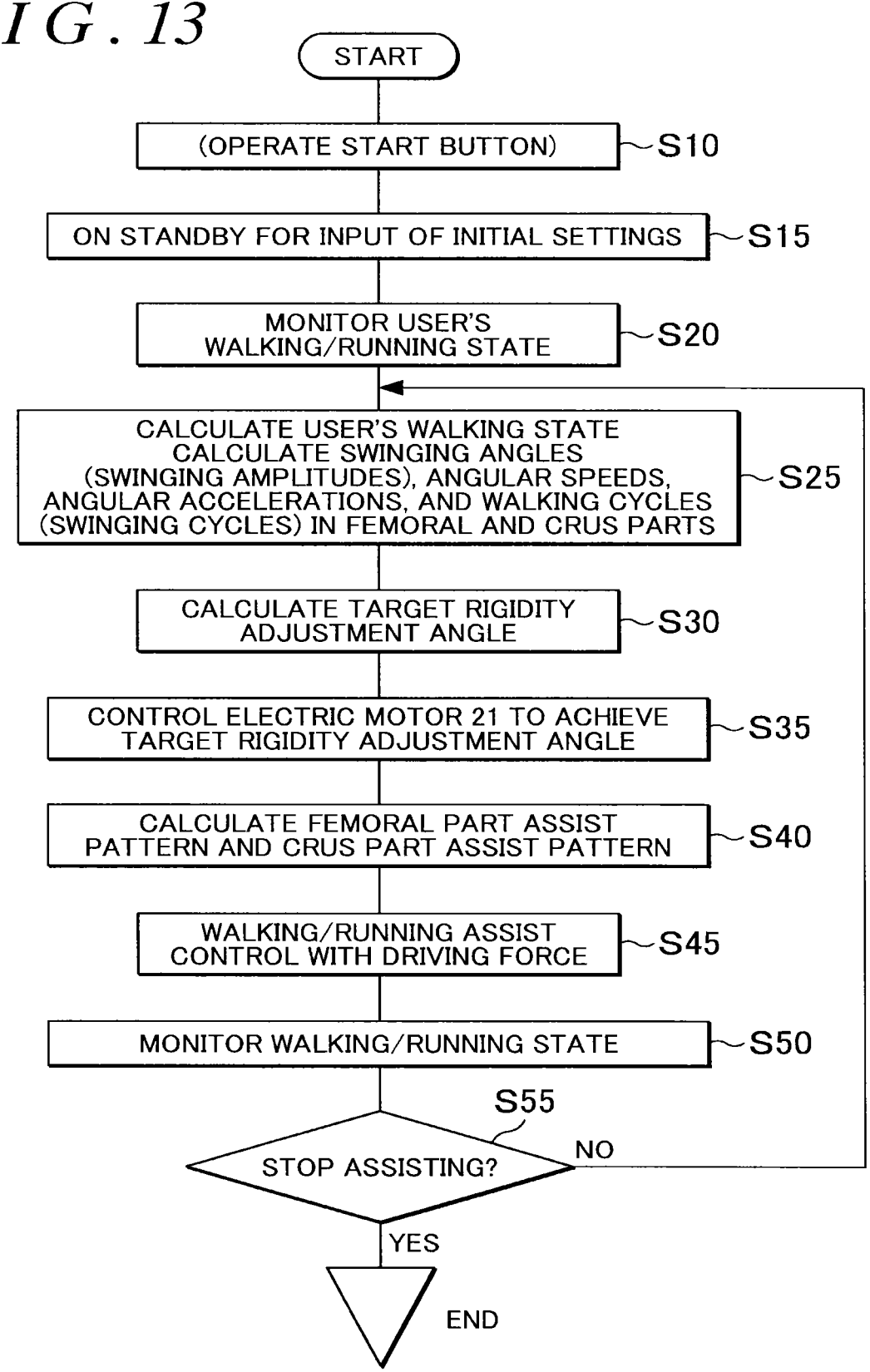
FIG. 13 is a flowchart illustrating an example of the processing procedure performed by the control portion.

Next, a description will be given of the processing procedure of the control portion 50 with reference to a flowchart shown in FIG. 13. When a user operates the start button of the control unit (step S10), the control portion proceeds to step S15.

In step S15, the control portion is on standby for the input of user's initial settings via the touch panel. After confirming the input of a user's height and weight, the control portion proceeds to step S20. Note that when the user's input is not confirmed even after the elapse of a prescribed time, the control portion sets, for example, a default (preset) standard height and weight and proceeds to step S20.

In step S20, the control portion measures a user's walking (or running) state without energizing the electric motors 11, 21, and 31 for a prescribed period and stores detection signals from the rotation angle detection portions 11S and 31S in the storage unit as measurement data corresponding to a measurement time. The shafts of the electric motors 11 and 31 are configured to idle at a non-energizing time. Note that the shaft of the electric motor 21 is configured to be locked without idling at the non-energizing time. An angle of the spring fixing member 23 caused to pivot by the electric motor 21 is adjusted to be a pivoting angle at which an urging torque is not generated in the flat spiral spring 24 when a swinging angle of the femoral swinging arm 13 is zero. After collecting the measurement data for, for example, a prescribed number of steps or a prescribed time, the control portion proceeds to step S25.

In step S25, the control portion calculates a swinging angle (or a swinging amplitude) of the femoral swinging arm from the measurement data based on the detection signal from the rotation angle detection portion 11S and calculates a walking cycle (or a swinging cycle) from an angular speed and an angular acceleration of the femoral swinging arm. In addition, the control portion similarly calculates a swinging angle (or a swinging amplitude) of the crus swinging arm from the measurement data based on the detection signal from the rotation angle detection portion 31S and calculates a walking cycle (or a swinging cycle) from an angular speed and an angular acceleration of the crus swinging arm. Then, the control portion proceeds to step S30.

In step S30, the control portion calculates a target rigidity adjustment angle as optimum joint rigidity based on the swinging angle and the swinging cycle of the femoral swinging arm calculated in step S25 and the user's height and weight and the like input in step S15. After that, the control portion proceeds to step S35. Note that a method for calculating the target rigidity adjustment angle will be described in detail later.

In step S35, the control portion controls the electric motor 21 to set an offset angle of the spring fixing member 23 at the target rigidity adjustment angle calculated in step S30. After that, the control portion proceeds to step S40.

In step S40, the control portion calculates the pattern of assisting the femoral part of a user (the pattern of outputting a driving signal to the electric motor 11, and the like) and the pattern of assisting the crus part of the user (the pattern of outputting a driving signal to the electric motor 31) based on the swinging angle and the swinging cycle of the femoral swinging arm and the swinging angle and the swinging cycle of the crus swinging arm calculated in step S25, an output voltage of the battery, and the like. After that, the control portion proceeds to step S45.

In step S45, the control portion starts outputting driving signals to the electric motors 11 and 31 based on the assist patterns calculated in step S40 to swing the femoral swinging arm 13 and the crus swinging arm 33 and assists the user's walking (or running) action such that the user's walking (or running) action continues. After that, the control portion proceeds to step S50. Note that the output of the driving signals to the electric motors 11 and 31 is continued even after the control portion transits to other steps.

In step S50, the control portion stores, as in the measurement of step S20, detection signals from the rotation angle detection portions 11S and 31S in the storage unit as measurement data corresponding to a measurement time while operating the electric motors 11 and 31 and assisting the user's walking (or running) action. After that, the control portion proceeds to step S55. Note that the collection of the measurement data is continued even after the control portion transits to other steps.

In step S55, the control portion determines whether the user wants to stop assisting the walking (or running) action based on the measurement data collected in step S50. When determining that the user wants to stop assisting the walking (or running) action (Yes), the control portion stops outputting the driving signals to the electric motors 11 and 31 to end the processing. On the other hand, when determining that the user does not want to stop assisting the walking (or running) action (No), the control portion returns to step S25.

Hereinafter, a description will be given of a method for calculating a target rigidity adjustment angle (FIG. 10) (target rigidity adjustment angle with respect to a swinging angle $\theta f$ of the femoral swinging arm 13 in the clockwise direction). First, a description will be given, with reference to FIG. 10, of a procedure for calculating a target rigidity adjustment angle performed in step S30 of the flowchart shown in FIG. 13. FIG. 10 shows an example of a case in which an offset angle in the clockwise direction is $\theta s$ (an offset angle in the "counterclockwise" direction is $-\theta s$), the femoral swinging arm 13 swings in the clockwise direction at a swinging angle $\theta f$, and a swinging angle of the shaft 25A of the transmission 25 in the clockwise direction is $n\theta f$ (i.e., a speed ratio of the transmission 25 is (n)). In addition, when efficiency of the transmission 25 is $\eta$, an apparent spring constant of the flat spiral spring 24 seen from the side of the femoral swinging arm 13 is k1, a spring constant of the flat spiral spring 24 seen from the side of the spring fixing member 23 is k (an original spring constant of the flat spiral spring 24), and a torque generated when the femoral swinging arm 13 swings is $\tau$, the following equation (1) is established.

$$\tau = k1 \cdot \theta f = \eta \cdot n \cdot k(n\theta f - \theta s) \qquad \text{Equation (1)}$$

When the above equation (1) is transformed, the apparent spring constant k1 of the flat spiral spring 24 seen from the side of the femoral swinging arm 13 can be determined by the following equation (2). In addition, the following equation (3) can be obtained when the following equation (2) is transformed.

$$k1 = \eta \cdot n^2 \cdot k[1 - \theta s/(n \cdot \theta f)] \qquad \text{Equation (2)}$$

$$\theta s = n \cdot \theta f[1 - k1/(\eta \cdot n^2 \cdot k)] \qquad \text{Equation (3)}$$

It is evident from the above equation (2) that, for example, the offset angle $\theta s$ is made equal to $n \cdot \theta f$ (i.e., $\theta s = n \cdot \theta f$) when the apparent spring constant k1 of the flat spiral spring 24 seen from the side of the femoral swinging arm 13 is set at zero. In addition, for example, it is evident from the equation (2) that the apparent spring constant k1 of the flat spiral spring 24 seen from the side of the femoral swinging arm 13 is equal to $\eta \cdot n^2 \cdot k$ (i.e., $k1 = \eta \cdot n^2 \cdot k$) when the offset angle $\theta s$ is set at zero. Moreover, for example, it is evident that the offset angle $\theta s$ is made equal to $-n \cdot \theta f$ (i.e., $\theta s = -n \cdot \theta f$) (that is, the state is a state in which the spring fixing member 23 pivots by $n \sim \theta f$ in the "counterclockwise" direction relative to the reference line J1 in the example of FIG. 10) when the apparent spring constant k1 of the flat spiral spring 24 seen from the side of the femoral swinging arm 13 is set at $2\eta \cdot n^2 \cdot k$ (i.e., $k1=2\cdot \eta \cdot n^2 \cdot k$).

Here, when a walking frequency (a swinging frequency of the femoral swinging arm) of a user is f and an angular frequency (angular speed) is ω at this time, the following equation (4) is established. The walking frequency f can be determined based on a measured cycle of user's walking (or running). Accordingly, a value ω in the following equation (4) can be determined.

$$\omega = 2 \cdot \pi \cdot f \qquad \text{Equation (4)}$$

In addition, as described above, an apparent spring constant of the flat spiral spring 24 seen from the side of the femoral swinging arm 13 is k1. Moreover, an inertia moment about the driving axis line 6J in a swinging object including the lower limb of a user, the femoral swinging arm 13, and the like is I. For example, the inertia moment I can be determined based on a (known) total mass of respective members swinging about the driving axis line 6J, a gravity center position of the total mass (that indicates a distance from the driving axis line 6J and is known), and a mass of the lower limb and a gravity center position of the lower limb (that indicates a distance from the driving axis line 6J and is known) estimated from a user's weight and height, and the following equations (5) and (6) are established. Since the value of ω is known from the above and the inertia moment I is also known, the apparent spring constant k1 of the flat spiral spring 24 seen from the side of the femoral swinging arm 13 can be determined by the following equation (6).

$$\omega = \sqrt{(k1/I)} \qquad \text{Equation (5)}$$

$$k1 = I \cdot \omega^2 \qquad \text{Equation (6)}$$

Moreover, when a viscosity coefficient about a joint axis (the driving axis line 6J) is ρ, the motion equation of the femoral swinging arm 13 (when an impact by gravity is sufficiently small) is generally expressed by the following equation (7). Note that the following equation (7) uses τ, I, and k1 described above and expresses a swinging angle as θ.

$$\tau = I \cdot \ddot{\theta} + \rho \cdot \dot{\theta} + k1 \cdot \theta \qquad \text{Equation (7)}$$

$$\left( \ddot{\theta} = \frac{d^2\theta}{dt^2}, \dot{\theta} = \frac{d\theta}{dt} \right)$$

The swinging of a femoral part produces a substantially sine wave. Therefore, when it is substituted into the above equation (7) as $\theta = A \cdot \sin \omega t$, the following equation (7A) can be obtained.

$$\tau = -A \cdot I \cdot \omega^2 \cdot \sin \omega t + A \cdot \rho \cdot \omega \cdot \cos \omega t + A \cdot k1 \cdot \sin \omega t \qquad \text{Equation (7A)}$$

$$= A(k1 - I \cdot \omega^2) \cdot \sin \omega t + A \cdot \rho \cdot \omega \cdot \cos \omega t$$

When $k1 = I \cdot \omega^2$, i.e., a resonance state is produced in the above equation (7A), τ can be minimized. Accordingly, energy that is the product of a torque and an angular displacement can also be minimized.

In the example of FIG. 10, the offset angle θs that minimizes the consumption power of the electric motor 11 when the femoral swinging arm 13 swings in the clockwise direction at the swinging angle θf is the target rigidity adjustment angle, and the offset angle θs determined by the above equations (7) and (2) is the target rigidity adjustment angle. In addition, by the above equations (6) and (2), the offset angle θs according to the angular frequency ω and the inertia moment I (offset angle θs at which the resonance frequency of the flat spiral spring and the swinging frequency of a swinging object coincide with each other) can be determined.

Hereinafter, a description will be given of a method for calculating a target rigidity adjustment angle (FIG. 11) (target rigidity adjustment angle with respect to a swinging angle θr of the femoral swinging arm 13 in the "counterclockwise" direction). In other words, a description will be given, with reference to FIG. 11, of a procedure for calculating a target rigidity adjustment angle performed in step S30 of the flowchart shown in FIG. 13. FIG. 11 shows an example of a case in which an offset angle in the clockwise direction is θs (an offset angle in the "counterclockwise" direction is –θs), the femoral swinging arm 13 swings in the "counterclockwise" direction at a swinging angle θr, and a swinging angle of the shaft 25A of the transmission 25 in the "counterclockwise" direction is nθr (i.e., a speed ratio of the transmission 25 is (n)). In addition, when efficiency of the transmission 25 is η, an apparent spring constant of the flat spiral spring 24 seen from the side of the femoral swinging arm 13 is k2, a spring constant of the flat spiral spring 24 seen from the side of the spring fixing member 23 is k, and a torque generated when the femoral swinging arm 13 swings is τ, the following equation (8) is established.

$$\tau = k2 \cdot \theta r = \eta \cdot n \cdot k (n\theta f + \theta s) \qquad \text{Equation (8)}$$

When the above equation (8) is transformed, the apparent spring constant k2 of the flat spiral spring 24 seen from the side of the femoral swinging arm 13 can be determined by the following equation (9). In addition, the following equation (10) can be obtained when the following equation (9) is transformed.

$$k2 = \eta \cdot n^2 \cdot k [1 + \theta s / (n \cdot \theta r)] \qquad \text{Equation (9)}$$

$$\theta s = -n \cdot \theta r [1 - k2 / (\eta \cdot n^2 \cdot k)] \qquad \text{Equation (10)}$$

It is evident from the above equation (9) that, for example, the offset angle θs is made equal to $-n \cdot \theta r$ (i.e., $\theta s = -n \cdot \theta r$) when the apparent spring constant k2 of the flat spiral spring 24 seen from the side of the femoral swinging arm 13 is set at zero. In addition, for example, it is evident from the equation (9) that the apparent spring constant k2 of the flat spiral spring 24 seen from the side of the femoral swinging arm 13 is equal to $\eta \cdot n^2 \cdot k$ (i.e., $k2 = \eta \cdot n^2 \cdot k$) when the offset angle θs is set at zero. Moreover, for example, it is evident that the offset angle θs is made equal to $n \cdot \theta r$ (i.e., $\theta s = n \cdot \theta r$) (that is, the state is a state in which the spring fixing member 23 pivots by $n \cdot \theta r$ in the clockwise direction relative to the reference line J1 in the example of FIG. 11) when the apparent spring constant k2 of the flat spiral spring 24 seen from the side of the femoral swinging arm 13 is set at $2 \cdot \eta \cdot n^2 \cdot k$ (i.e., $k2 = 2 \cdot \eta \cdot n^2 \cdot k$).

Here, when a walking frequency (a swinging frequency of the femoral swinging arm) of a user is f and an angular frequency (angular speed) is ω at this time, the above equation (4) is established. In addition, when an apparent spring constant of the flat spiral spring 24 seen from the side of the femoral swinging arm 13 is k2 and an inertia moment about the driving axis line 6J in the swinging object including the lower limb of a user, the femoral swinging arm 13, and the like is I as in the above, the following equations (11) and (12) are established. Since the value of co is known from the above and the inertia moment I is also known, the apparent spring constant k2 of the flat spiral spring 24 seen from the side of the femoral swinging arm 13 can be determined by the following equation (12).

$$\omega = \sqrt{(k2/I)} \qquad \text{Equation (11)}$$

$$k2 = I \cdot \omega^2 \qquad \text{Equation (12)}$$

Moreover, when a viscosity coefficient about a joint axis (the driving axis line 6J) is ρ, the motion equation of the femoral swinging arm 13 is generally expressed by the following equation (13). Note that the following equation (13) uses τ, I, and k2 described above and expresses a swinging angle as θ.

$$\tau = I \cdot \ddot{\theta} + \rho \cdot \dot{\theta} + k2 \cdot \theta \qquad \text{Equation (13)}$$

$$\left( \ddot{\theta} = \frac{d^2\theta}{dt^2}, \dot{\theta} = \frac{d\theta}{dt} \right)$$

The swinging of a femoral part produces an almost sine wave. Therefore, when it is substituted into the above equation (13) as θ=A·sin ωt, the following equation (13A) can be obtained.

$$\tau = -A \cdot I \cdot \omega^2 \cdot \sin\omega t + A \cdot \rho \cdot \omega \cdot \cos\omega t + A \cdot k2 \cdot \sin\omega t \qquad \text{Equation (13A)}$$

$$= A(k2 - I \cdot \omega^2) \cdot \sin\omega t + A \cdot \rho \cdot \omega \cdot \cos\omega t$$

When $k2 = I \cdot \omega^2$ is established, i.e., a resonance state is produced in the above equation (13A), τ can be minimized. Accordingly, energy that is the product of a torque and an angular displacement can also be minimized.

In the example of FIG. 11, the offset angle θs that minimizes the consumption power of the electric motor 11 when the femoral swinging arm 13 swings in the "counterclockwise" direction at the swinging angle θr is the target rigidity adjustment angle, and the offset angle θs obtained by the above equations (13) and (9) is the target rigidity adjustment angle. In addition, by the above equations (12) and (9), the offset angle θs according to the angular frequency ω and the inertia moment I (offset angle θs at which the resonance frequency of the flat spiral spring and the swinging frequency of the swinging object coincide with each other) can be obtained.

As described above with reference to FIGS. 10 and 11, the rigidity adjustment angle (the offset angle θs in the clockwise direction) is adjusted by the control portion 50 to make the resonance angular frequency (ω) of the flat spiral spring 24 and the swinging frequency of the swinging object coincide with each other, based on the swinging frequency (f) of the femoral swinging arm 13 about the driving shaft member 6, the inertia moment (I) about the driving shaft member 6 in the swinging object including the femoral swinging arm 13 (all objects including the lower limb of a user and the femoral swinging arm 13 and swinging about the driving axis line 6J), the spring constant (k) of the flat spiral spring 24, the offset angle (θs) of the flat spiral spring 24, and the swinging angle (θf) of the femoral swinging arm 13 in the clockwise direction or the swinging angle (θr) of the femoral swinging arm 13 in the "counterclockwise" direction.

As described above, the rigidity adjustment angle (the offset angle θs in the clockwise direction) is set such that the resonance angular frequency (ω) of the flat spiral spring 24 coincides with the swinging frequency of the swinging object (the whole object swinging about the driving shaft member 6) including the femoral swinging arm 13. Thus, power consumed by the electric motor 11 can be minimized. Note that the rigidity adjustment angle may not be calculated according to the above equation but may be calculated according to other methods. That is, in another method, the rigidity adjustment angle is minutely changed, and the consumption power of the electric motor 11 for a prescribed cycle is measured at the rigidity adjustment angle. After that, the rigidity adjustment angle is minutely changed again, and the consumption power of the electric motor 11 for the prescribed cycle is measured. By repeatedly measuring the consumption power of the electric motor 11 in this manner, the rigidity adjustment angle resulting in the minimum consumption power can be calculated. In addition, by amplifying the swinging angle of the femoral swinging arm 13 with the transmission 25 and inputting the amplified swinging angle to the flat spiral spring 24, it is possible to use a small flat spiral spring having a relatively small spring constant. Moreover, it is also possible to use a small electric motor having a smaller torque, as the electric motor 21.

The swinging joint device 1 of the first embodiment described above is used for the left leg of a user. However, the control unit 5 may assist the walking (or running) action of both legs of a user with the addition of a base portion for the right leg (symmetrical to the base portion 2), a femoral swinging portion for the right leg (symmetrical to the respective members indicated by symbols 11, 12, 14, 14B, 15, 13, 19, and the like), a rigidity adjustment portion for the right leg (symmetrical to the respective members indicated by symbols 21, 22, 23, 24, 25, and the like), and a crus swinging portion for the right leg (symmetrical to the respective members indicated by symbols 31, 32, 32P, 32B, 33, 34, 35, 36, 39, and the like).

Hereinafter, a description will be given of a swinging joint device of a second embodiment. The swinging joint device of the second embodiment is one in which the electric motor 11 (and the rotation angle detection portion 11S), the bracket 12, the pulley 14, and the belt 14B are removed from the swinging joint device 1 of the first embodiment shown in FIGS. 1 to 4 and a rotation angle detection portion capable of detecting a swinging angle of the femoral swinging arm 13 is added to the swinging joint device 1 of the first embodiment. In the second embodiment, the motion of a femoral part cannot be assisted by an electric motor when a user walks (or runs), but the motion of a crus part can be assisted by the electric motor 31. In addition, since the swinging joint device includes the rigidity adjustment portion indicated by symbols 21, 22, 23, 24, 25, and the like, it is possible to set the rigidity adjustment angle (the offset angle θs in the clockwise direction) at an appropriate angle so as to produce a resonance state at all times. Thus, a motion amount of the femoral part of a user can be appropriately reduced.

In addition, as is the case with the first embodiment, the control unit 5 may assist the walking (or running) action of both legs of a user with the addition of a base portion for the right leg (symmetrical to the base portion 2), a femoral swinging portion for the right leg (symmetrical to the respective members indicated by symbols 13, 19, and the like), a rigidity adjustment portion for the right leg (symmetrical to the respective members indicated by symbols 21, 22, 23, 24, 25, and the like), and a crus swinging portion for the right leg (symmetrical to the respective members indicated by symbols 31, 32, 32P, 32B, 33, 34, 35, 36, 39, and the like).

Hereinafter, a description will be given of a swinging joint device of a third embodiment. The swinging joint device of the third embodiment is one in which the electric motor 31, the bracket 32, the pulley 32P, the belt 32B, the crus swinging arm 33, the ems relaying arm 34, the crus arm 35, the foot holding portion 36, and the ems attachment portion 39 are removed from the swinging joint device 1 of the first embodiment shown in FIGS. 1 to 4. In the third embodiment, the motion of a femoral part is assisted by the electric motor 11 when a user walks (or runs), but the motion of a crus part is not assisted. Note that since the swinging joint device includes the rigidity adjustment portion indicated by symbols 21, 22, 23, 24, 25, and the like, it is possible to set the rigidity adjustment angle (the offset angle θs in the clockwise direction) at an appropriate angle so as to produce a resonance state at all times. Thus, the consumption power of the electric motor 11 can be further reduced.

In addition, as is the case with the first embodiment, the control unit 5 may assist the walking (or running) action of both legs of a user with the addition of a base portion for the right leg (symmetrical to the base portion 2), a femoral swinging portion for the right leg (symmetrical to the respective members indicated by symbols 11, 12, 14, 14B, 15, 13, 19, and the like), and a rigidity adjustment portion for the right leg (symmetrical to the respective members indicated by symbols 21, 22, 23, 24, 25, and the like).

Hereinafter, a description will be given of a swinging joint device of a fourth embodiment. The swinging joint device of the fourth embodiment is one in which the electric motor 11 (and the rotation angle detection portion 11S), the bracket 12, the pulley 14, and the belt 14B are removed from the swinging joint device of the third embodiment and a rotation angle detection portion capable of detecting a swinging angle of the femoral swinging arm 13 is added to the swinging joint device of the third embodiment. In the fourth embodiment, the motion of a crus part cannot be assisted when a user walks (or runs). In addition, the motion of the femoral part of a user cannot be assisted by an electric motor. However, since the swinging joint device includes the rigidity adjustment portion indicated by symbols 21, 22, 23, 24, 25, and the like, it is possible to set the rigidity adjustment angle (the offset angle θs in the clockwise direction) at an appropriate angle so as to produce a resonance state at all times. Thus, a motion amount of the femoral part of a user can be appropriately reduced.

In addition, as is the case with the first embodiment, the control unit 5 may assist the walking (or running) action of both legs of a user with the addition of a base portion for the right leg (symmetrical to the base portion 2), a femoral swinging portion for the right leg (symmetrical to the respective members indicated by symbols 13, 19, and the like), and a rigidity adjustment portion for the right leg (symmetrical to the respective members indicated by symbols 21, 22, 23, 24, 25, and the like).

Figure 14:
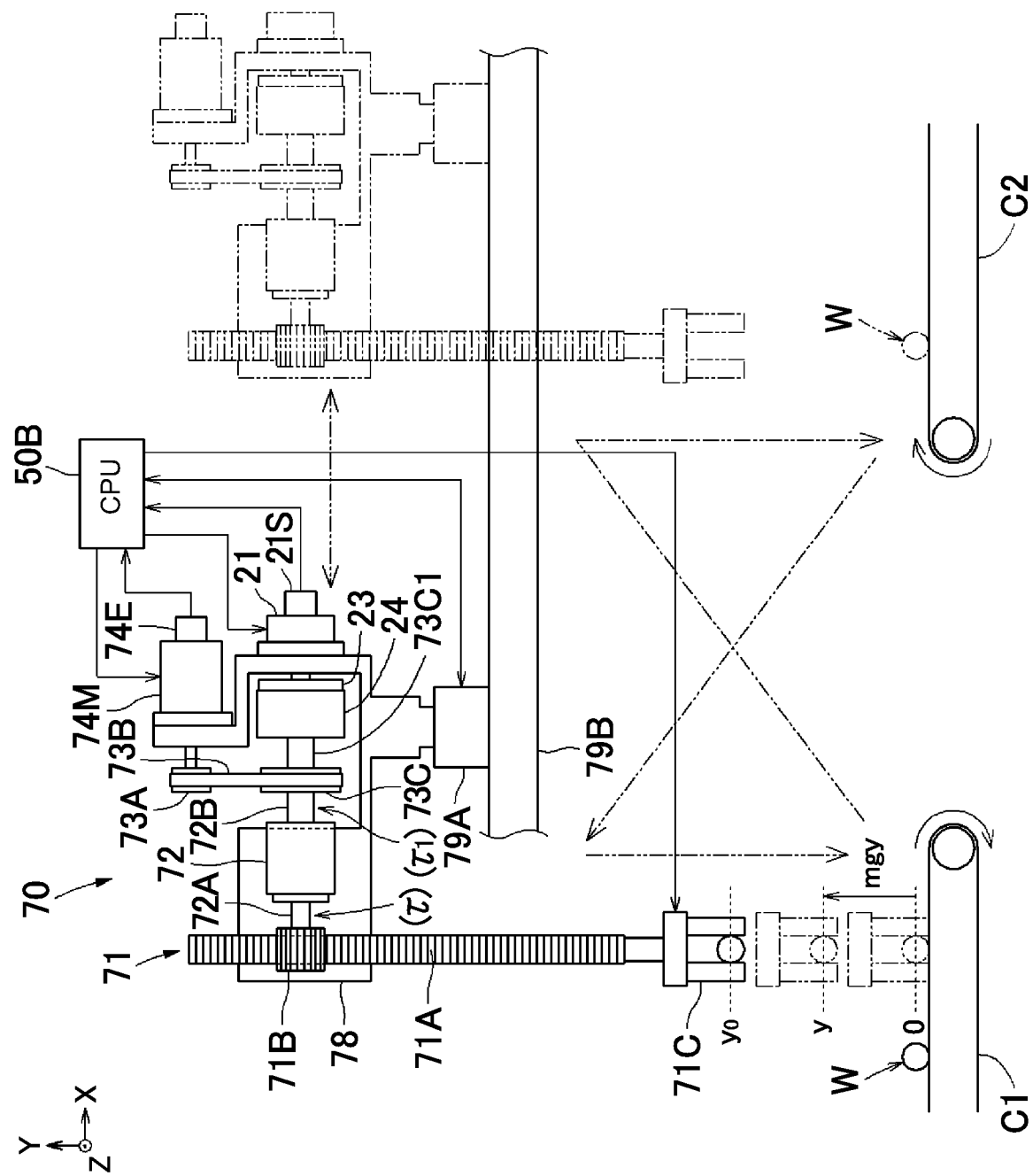
FIG. 14 is a view illustrating the entire configuration and the outline of the operations of a conveying device of a fifth embodiment.

Hereinafter, a description will be given of a fifth embodiment (an example (FIG. 14) in which an apparent rigidity variable portion is applied to a conveying device 70 including a reciprocating linear motion body). The following fifth embodiment will describe an example of the conveying device 70 including a part (including at least the apparent rigidity variable portion) of the above swinging joint device. Note that a Y-axis direction in FIG. 14 indicates a vertically-upward direction.

Hereinafter, a description will be given of the entire configuration (FIG. 14) of the conveying device 70. The conveying device 70 shown in FIG. 14 includes an arm 71, a pinion 71B, a speed reducer 72 (transmission), a driven pulley 73C, a belt 73B, a driving pulley 73A, a vertical driving actuator 74M, a rotation angle detection portion 74E, a flat spiral spring 24, a spring fixing member 23, an electric motor 21, a rotation angle detection portion 21S, a supporting body 78, a slide driving body 79A, a control portion 50B, and the like. Note that the vertical driving actuator 74M corresponds to a pinion driving portion. In addition, the electric motor 21 is a rigidity variable actuator and corresponds to a rigidity adjustment member. The conveying device 70 shown in the example of FIG. 14 reciprocates the arm 71 linearly in a vertical direction while reciprocating on a guiding member 79B (in a horizontal direction) to hold a workpiece W on a conveyor C1 and moves the held workpiece W onto a conveyor C2. Note that the flat spiral spring 24, the spring fixing member 23, the electric motor 21, and the rotation angle detection portion 21S are the same as those shown in FIG. 5.

The supporting body 78 supports the pinion 71B, a pinion-side shaft 72A, the speed reducer 72, a pulley-side shaft 72B, the driven pulley 73C, a spring-side shaft 73C1, the flat spiral spring 24, the spring fixing member 23, and the electric motor 21 such that they are coaxial with each other. In addition, the supporting body 78 guides the arm 71 such that the arm 71 is capable of linearly reciprocating in the vertical direction. Moreover, the supporting body 78 is provided with a slide driving body 79A capable of reciprocating (in the horizontal direction) along the guiding member 79B. The control portion 50B is capable of outputting a control signal to the slide driving body 79A while detecting a position detection signal from the slide driving body 79A and capable of reciprocating the conveying device 70 along the guiding member 79B.

The arm 71 is a member that has a rack portion 71A to engage with the pinion 71B and extends in the vertical direction, and has a holding portion 71C that holds and releases the workpiece W at its lower end. The arm 71 is guided by the supporting body 78 to linearly reciprocate upward or downward according to the rotation of the pinion 71B. Note that the holding portion 71C of the arm 71 holds or releases the workpiece W according to a control signal from the control portion 50B.

The speed reducer 72 reduces rotation input from the pulley-side shaft 72B by 1/n times and outputs the reduced rotation to the pinion-side shaft 72A (the speed reducer 72 amplifies rotation input from the pinion-side shaft 72A by n times and output the amplified rotation to the pulley-side shaft 72B).

The driven pulley 73C is connected to the pulley-side shaft 72B and the spring-side shaft 73C1 and receives the rotation power of the vertical driving actuator 74M via the driving pulley 73A and the belt 73B. The control portion 50B outputs a control signal to the vertical driving actuator 74M while detecting a detection signal from the rotation angle detection portion 74E. Note that the spring-side shaft 73C1 is connected to a free end (corresponding to the free end 24B in FIG. 5) serving as one end of the flat spiral spring 24.

With the above configuration, the flat spiral spring 24 is wound in a direction in which its diameter reduces (or increases) to accumulate energy when the vertical driving actuator 74M rotates and drives the pinion 71B. At this time, the driven pulley 73C is rotated and driven by the vertical driving actuator 74M, and the driven pulley 73C moves the arm 71 upward (or downward) via the speed reducer 72 and the pinion 71B. In addition, the flat spiral spring 24 rotates and drives the pinion 71B while being restored from a state in which its diameter is reduced (or increased) in order to release accumulated energy. At this time, the driven pulley 73C is rotated and driven by the flat spiral spring 24, and the driven pulley 73C moves the arm 71 downward (or upward) via the speed reducer 72 and the pinion 71B.

As described above, the free end serving as one end of the flat spiral spring 24 corresponds to the free end 24B in FIG. 5 and is connected to the spring-side shaft 73C1. In addition, a fixed end serving as the other end of the flat spiral spring 24 corresponds to the fixed end 24A in FIG. 5 and is supported by a spring supporting body 23J of the spring fixing member 23.

The spring fixing member 23 is the same as the spring fixing member 23 shown in FIG. 5, has the spring supporting body 23J, and is caused to pivot by the electric motor 21. Further, the control portion 50B outputs a control signal to the electric motor 21 while detecting a detection signal from the rotation angle detection portion 21S.

As described above, the conveying device 70 includes the following respective portions in the swinging joint device. The pinion-side shaft 72A corresponds to a driving shaft member of the swinging joint device. The pinion 71B that reciprocates and pivots corresponds to a first output portion of the swinging joint device. The reciprocating and pivoting angle of the pinion 71B corresponds to a first swinging angle of the swinging joint device. The rotation angle detection portion 74E corresponds to a first angle detection portion of the swinging joint device. The flat spiral spring 24 corresponds to an elastic body of the swinging joint device. The apparent spring constant of the flat spiral spring 24 (seen from the pinion 71B) corresponds to apparent rigidity of the swinging joint device (seen from the first output portion). Furthermore, the apparent spring constant variable portion that varies the apparent spring constant (seen from the pinion 71B) and that is constituted by the spring fixing member 23 and the electric motor 21 corresponds to an apparent rigidity variable portion of the swinging joint device.

Hereinafter, a description will be given of a method for calculating a target rigidity adjustment angle (a pivoting angle of the spring fixing member 23) according to a pivoting angle θ of the pinion 71B. Here, the equation of motion shown in the following equation (14) is established when a thrust of the arm 71 in the vertical direction is F, a mass of the arm 71 is m (it is assumed that a mass of the workpiece W can be regarded as negligible), a viscosity coefficient of the arm 71 in the vertical motion is d, rigidity of the arm 71 in the Y-axis direction is $k_L$, a Y-axis coordinate of the lower-end position of the arm 71 is y, a Y-axis coordinate of the upper-end position of the arm 71 is $y_0$, and a gravitational acceleration is g.

$$F = m\ddot{y} + d\dot{y} + k_L(y-y_0) + mg \quad \text{Equation (14)}$$

In this case, a total sum E of the energy of the system can be expressed by the following equation (15).

$$E = \frac{1}{2}m\dot{y}^2 + \frac{1}{2}k_L(y-y_0)^2 + mgy \quad \text{Equation (15)}$$

Here, a condition for minimizing the total sum E of the energy in the above equation (15) is shown in the following equation (16), and the following equations (17), (18), and (19) can be obtained by the following equation (16).

$$\frac{dE}{dt} = m\dot{y}\ddot{y} + k_L(y-y_0)\dot{y} + mg\dot{y} \quad \text{Equation (16)}$$
$$= \{m\ddot{y} + k_L(y-y_0) + mg\}\dot{y}$$
$$= 0$$

$$m\ddot{y} + k_L(y-y_0) + mg = 0 \quad \text{Equation (17)}$$

$$k_L(y-y_0) = -m(\ddot{y}+g) \quad \text{Equation (18)}$$

$$k_L = -m\frac{\ddot{y}+g}{y-y_0} \quad \text{Equation (19)}$$

The total sum E of the energy can be minimized when the rigidity $k_L$ is controlled as in the above equation (19). However, since the rigidity $k_L$ becomes a positive (or negative) infinity when $y-y_0$ (corresponding to the pivoting angle θ of the pinion 71B) is close to zero, $k_L$ is fixed at its upper limit (physical upper limit (generally set) of the spring constant of the flat spiral spring 24) when $y-y_0$ is close to zero.

Here, when the arm 71 oscillates in an almost sine wave pattern about $y_0$ in its vertical motion and is expressed by the following equation (20), $k_L$ is controlled as in the following equation (21).

$$y = y_0 A \sin \omega t \quad \text{Equation (20)}$$

$$k_L = m[(A\omega^2 \sin \omega t - g)/(A\omega t)] = m[\omega^2 - g/(A \sin \omega t)] \quad \text{Equation (21)}$$

In addition, the relationship between a vertical displacement y and a rotation displacement θ (the pivoting angle of the pinion 71B) can be expressed by the following equation (22) when a pitch circle radius of the pinion is r. Note that $\theta_0$ is an angle before a displacement and $y_0$ is a position before the displacement.

$$r(\theta - \theta_0) = y - y_0 \quad \text{Equation (22)}$$

The following equation (23) is established when consideration is given to the fact that the output of the speed reducer 72 is converted into a thrust f in a direct-acting direction by a rack and pinion, and the following equation (24) can be obtained by the following equations (23) and (22).

$$f = k_L(y-y_0) \quad \text{Equation (23)}$$

$$f = k_L r(\theta - \theta_0) \quad \text{Equation (24)}$$

Here, the following equation (25) is established when a torque generated in the pinion 71B by the flat spiral spring 24 is τ, apparent rigidity in a rotating direction is $k_R$, a torque by the flat spiral spring 24 is $\tau_1$, a speed reduction ratio of the speed reducer 72 is n, and efficiency of the speed reducer 72 is $\eta_R$. In addition, a torque $\tau_1$ generated in the pulley-side shaft 72B of the speed reducer 72 is obtained by the following equation (26) when an original spring constant of the flat spiral spring is k.

$$\tau = k_R(\theta - \theta_0) = \eta_R n \tau_1 \quad \text{Equation (25)}$$

$$\tau_1 = kn(\theta - \theta_0) \quad \text{Equation (26)}$$

The following equation (27) can be obtained by the above equations (25) and (26).

$$\tau = \eta_R n^2 k(\theta - \theta_0) \quad \text{Equation (27)}$$

Here, the following equation (28) can be obtained when it is assumed that the fixed end 24A of the flat spiral spring 24 pivots by $\theta_1$ (the offset angle $\theta_s$ (corresponding to $\theta_1$) in FIG. 9 is provided) with respect to the above equation (26).

$$\tau = k[n(\theta-\theta_0) - \theta_1] \quad \text{Equation (28)}$$

The following equation (29) can be obtained by the above equations (25) and (28).

$$\tau = \eta_R n k[n(\theta-\theta_0) - \theta_1] = \eta_R n^2 k\{1 - \theta_1/[n(\theta-\theta_0)]\}(\theta-\theta_0) \quad \text{Equation (29)}$$

The following equation (30) is obtained by the above equations (29) and (25), and the following equation (31) can be obtained when the following equation (30) is transformed for $k_R$.

$$\eta_R n^2 k\{1 - \theta_1/[n(\theta-\theta_0)]\}(\theta-\theta_0) = k_R(\theta-\theta_0) \quad \text{Equation (30)}$$

$$k_R = \eta_R n^2 k\{1 - \theta_1/[n(\theta-\theta_0)]\} \quad \text{Equation (31)}$$

Here, the following equation (32) is obtained when efficiency of a rack and pinion mechanism is $\eta_L$ and the work of a direct-acting portion equals the work of a rotating portion, and the following equation (33) can be obtained by the following equation (32) and the above equation (22).

$$f(y-y_0) = \eta_L \tau(\theta-\theta_0) \quad \text{Equation (32)}$$

$$fr(\theta-\theta_0) = \eta_L \tau(\theta-\theta_0) \quad \text{Equation (33)}$$

The following equation (34) can be obtained by the above equations (24) and (33).

$$k_L r^2(\theta-\theta_0)^2 = \eta_L \tau(\theta-\theta_0) \quad \text{Equation (34)}$$

The following equation (35) is obtained by the above equations (34) and (29), and the following equation (36) can be obtained when the following equation (35) is transformed for $k_L$. In addition, the following equation (37) can be obtained when the following equation (35) is transformed for $\theta_1$. Accordingly, $\theta_1$ can be controlled as in the following equation (37) with respect to the required $k_L$.

$$k_L r^2 (\theta-\theta_0)^2 = \eta_L \eta_R n^2 k\{1-\theta_1/[n(\theta-\theta_0)]\}(\theta-\theta_0)^2 \quad \text{Equation (35)}$$

$$k_L = \eta_L \eta_R n^2 k\{1-\theta_1/[n(\theta-\theta_0)]\}1/r^2 \quad \text{Equation (36)}$$

$$\theta_1 = [1 - k_L r^2/(\eta_L \eta_R n^2 k)] n(\theta-\theta_0) \quad \text{Equation (37)}$$

As described above, the angle $\theta_1$ (corresponding to the offset angle $\theta_s$ shown in FIG. 9) of the position of the fixed end 24A of the flat spiral spring 24 is adjusted so as to satisfy the above equation (37) in real time with respect to the rotating displacement $\theta$ of the pinion 71B. Thus, the consumption energy of the vertical driving actuator 74M can be minimized.

Figure 15:
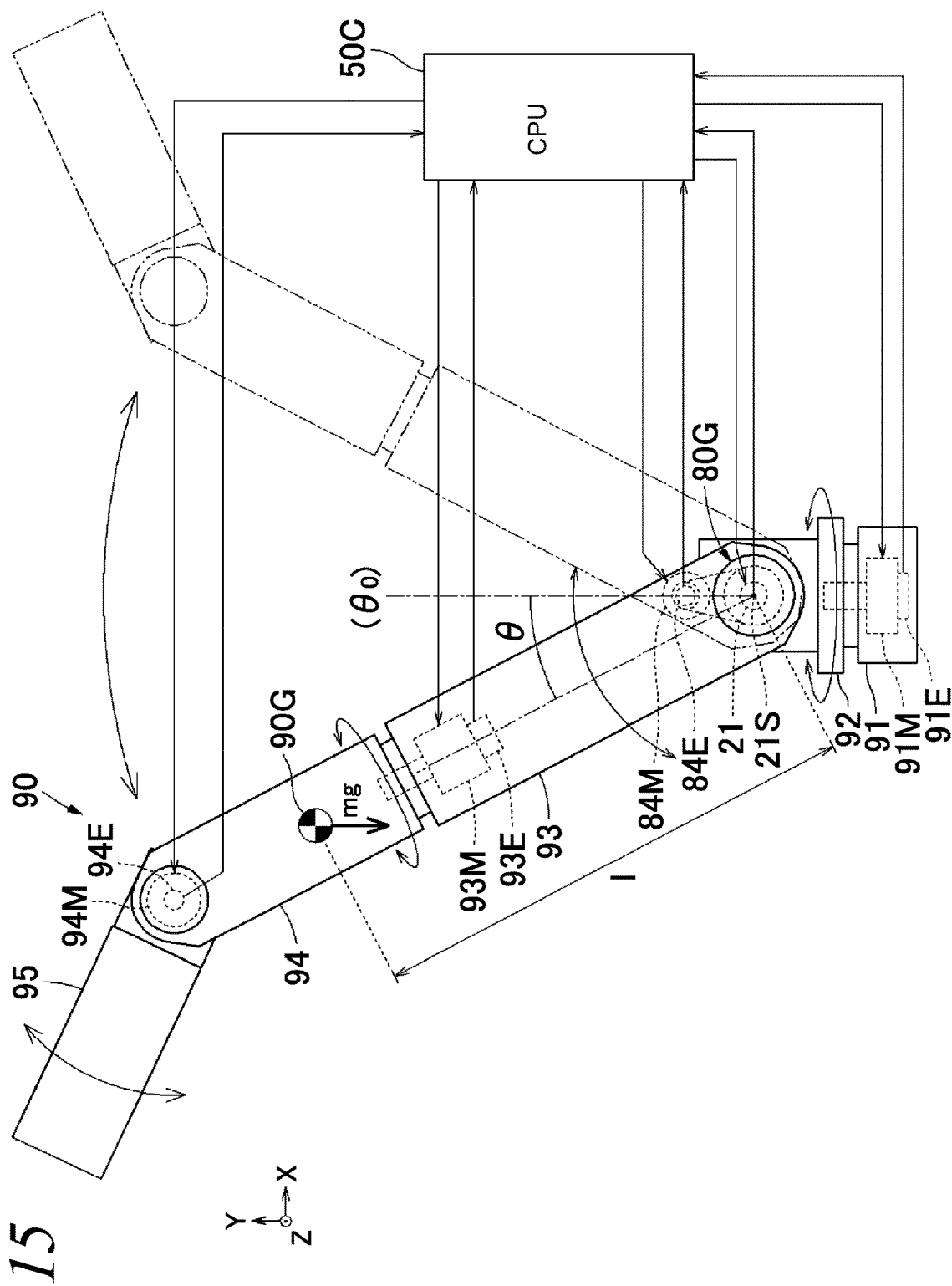
FIG. 15 is a front view illustrating the entire configuration and the outline of the operations of a manipulator of a sixth embodiment.
Figure 16:
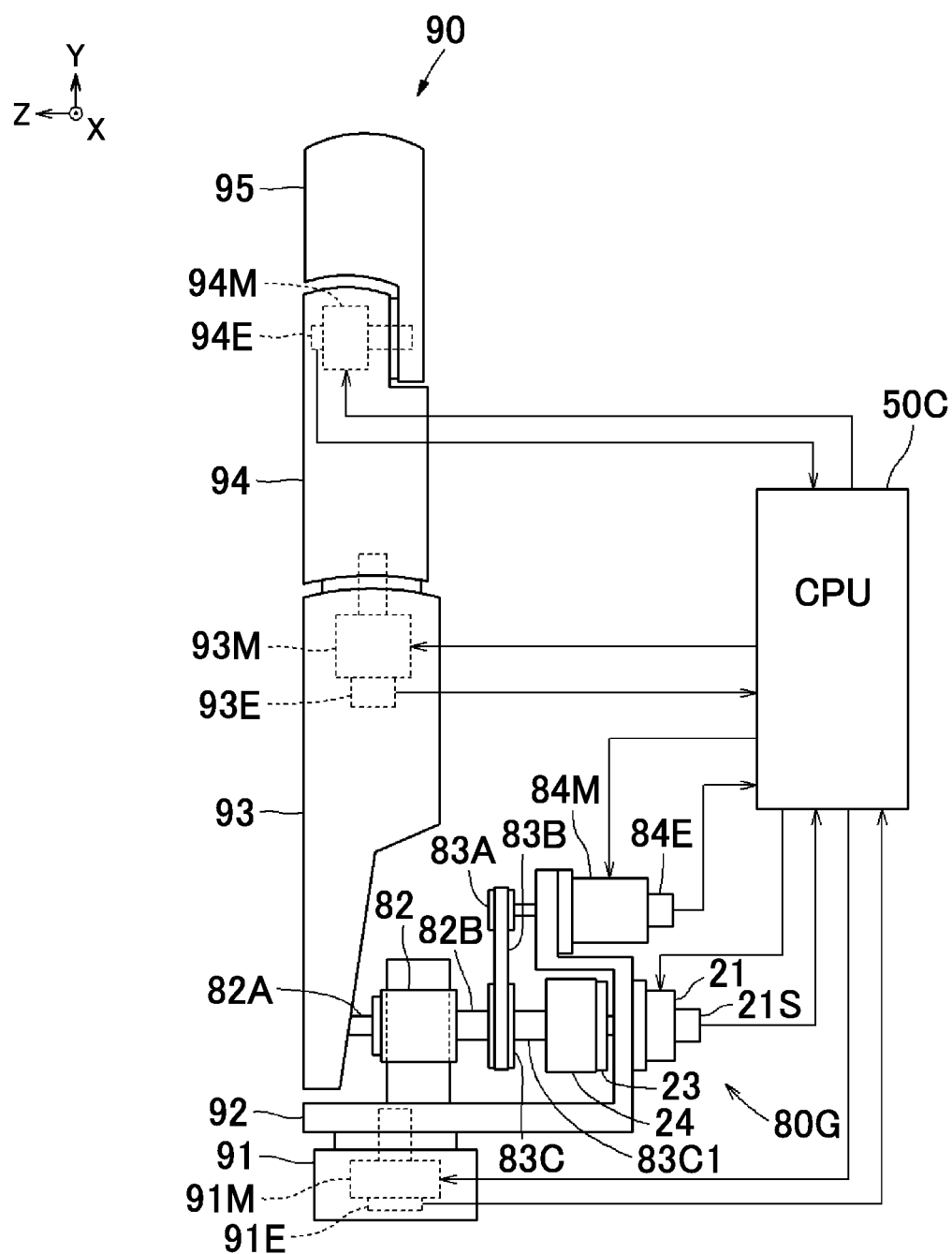
FIG. 16 is a side view of the manipulator shown in FIG. 15.

Hereinafter, a description will be given of a sixth embodiment (an example (FIGS. 15 and 16) in which an apparent rigidity variable portion is applied to a manipulator 90 including a swinging motion body) and the entire configuration (FIGS. 15 and 16) of the manipulator 90. A description will be given, with reference to FIGS. 15 and 16, of an example in which the above apparent rigidity variable portion is applied to a swinging motion body (a first swinging portion 93 integrated with a second swinging portion 95 and a second pivoting portion 94). The manipulator 90 shown in FIGS. 15 and 16 includes a base 91, a first pivoting portion 92, the first swinging portion 93, the second pivoting portion 94, the second swinging portion 95, a control portion 50C, and the like.

The base 91 is provided with an electric motor 91M having a rotation angle detection portion 91E, and the electric motor 91M pivots the first pivoting portion 92 relative to the base 91. In addition, the first pivoting portion 92 is provided with a rigidity variable swinging device 80G having an electric motor 84M (corresponding to a swinging portion driving portion) having a rotation angle detection portion 84E, and the rigidity variable swinging device 80G swings the first swinging portion 93 relative to the first pivoting portion 92. Note that the rigidity variable swinging device 80G will be described in detail later. Moreover, the first swinging portion 93 is provided with an electric motor 93M having a rotation angle detection portion 93E, and the electric motor 93M pivots the second pivoting portion 94 relative to the first swinging portion 93. Further, the second pivoting portion 94 is provided with an electric motor 94M having a rotation angle detection portion 94E, and the electric motor 94M swings the second swinging portion 95 relative to the second pivoting portion 94. The control portion 50C outputs a control signal to the electric motor 91M while detecting a detection signal from the rotation angle detection portion 91E, and outputs a control signal to the electric motor 84M while detecting a detection signal from the rotation angle detection portion 84E. In addition, the control portion 50C outputs a control signal to the electric motor 93M while detecting a detection signal from the rotation angle detection portion 93E, and outputs a control signal to the electric motor 94M while detecting a detection signal from the rotation angle detection portion 94E.

The rigidity variable swinging device 80G includes a swinging-body-side shaft 82A, a speed reducer 82, a pulley-side shaft 82B, a driven pulley 83C, a belt 83B, a driving pulley 83A, an electric motor 84M, a rotation angle detection portion 84E, a spring-side shaft 83C1, a flat spiral spring 24, a spring fixing member 23, an electric motor 21 (that is a rigidity variable actuator and corresponds to a rigidity adjustment member), and a rotation angle detection portion 21S, and is provided in the first pivoting portion 92. The manipulator 90 shown in FIGS. 15 and 16 swings the first swinging portion 93 and the portions above the first swinging portion 93 (that is, the first swinging portion 93, the second pivoting portion 94, and the second swinging portion 95). Note that the flat spiral spring 24, the spring fixing member 23, the electric motor 21, and the rotation angle detection portion 21S are the same as those shown in FIG. 5. Note that the first swinging portion 93 and the portions above the first swinging portion 93 cyclically swing at a prescribed amplitude.

The first pivoting portion 92 serving as the supporting body of the rigidity variable swinging device 80G supports the swinging-body-side shaft 82A, the speed reducer 82, the pulley-side shaft 82B, the driven pulley 83C, the spring-side shaft 83C1, the flat spiral spring 24, the spring fixing member 23, and the electric motor 21 such that they are coaxial with each other. Note that since the speed reducer 82, the pulley-side shaft 82B, the driven pulley 83C, the belt 83B, the driving pulley 83A, the electric motor 84M, the spring-side shaft 83C1, the flat spiral spring 24, the spring fixing member 23, and the electric motor 21 are the same as the speed reducer 72, the pulley-side shaft 72B, the driven pulley 73C, the belt 73B, the driving pulley 73A, the vertical driving actuator 74M, the spring-side shaft 73C1, the flat spiral spring 24, the spring fixing member 23, and the electric motor 21 shown in FIG. 14, respectively, their descriptions will be omitted. The speed reducer 82 reduces rotation input from the pulley-side shaft 82B by 1/n times and outputs the reduced rotation to the swinging-body-side shaft 82A (the speed reducer 82 amplifies rotation input from the swinging-body-side shaft 82A by n times and outputs the amplified rotation to the pulley-side shaft 82B).

With the above configuration, the flat spiral spring 24 is wound in a direction in which its diameter reduces (or increases) to accumulate energy when the electric motor 84M rotates and drives the driven pulley 83C. At this time, the driven pulley 83C rotated and driven by the electric motor 84M swings the first swinging portion 93 via the speed reducer 82 and the swinging-body-side shaft 82A. In addition, the flat spiral spring 24 rotates and drives the driven pulley 83C while being restored from a state in which its diameter is reduced (or increased) in order to release accumulated energy. At this time, the driven pulley 83C rotated and driven by the flat spiral spring 24 swings the first swinging portion 93 via the speed reducer 82 and the swinging-body-side shaft 82A.

As described above, the manipulator 90 includes the following respective portions in the swinging joint device. The swinging-body-side shaft 82A corresponds to the driving shaft member of the swinging joint device. The first swinging portion 93 that swings corresponds to the first output portion of the swinging joint device. The swinging angle θ of the first swinging portion 93 corresponds to the first swinging angle of the swinging joint device. The rotation angle detection portion 84E corresponds to the first angle detection portion of the swinging joint device. The flat spiral spring 24 corresponds to the elastic body of the swinging joint device. The apparent spring constant of the flat spiral spring 24 (seen from the first swinging portion 93) corresponds to apparent rigidity of the swinging joint device (seen from the first output portion). The apparent spring constant variable portion that varies the apparent spring constant (seen from the first swinging portion 93) and that is constituted by the spring fixing member 23 and the electric motor 21 corresponds to the apparent rigidity variable portion of the swinging joint device.

Hereinafter, a description will be given of a method for calculating a target rigidity adjustment angle (a pivoting angle of the spring fixing member 23) according to a swinging angle θ of the first swinging portion 93. Here, the following equations (38) and (39) are established as for a torque τ generated by the flat spiral spring 24 when apparent rigidity (spring constant) of the flat spiral spring 24 seen from the first swinging portion 93 is $k_R$, the swinging angle of the first swinging portion 93 is θ, an angle at a position corresponding to the center of swinging is $\theta_0$, a speed reduction ratio of the speed reducer 82 is n, efficiency of the speed reducer 82 is $\eta_R$, and a torque generated in the pulley-side shaft 82B of the speed reducer 82 by the flat spiral spring 24 is $\tau_1$.

$\tau = k_R(\theta - \theta_0)$ Equation (38)

$\tau = \eta_R n \tau_1$ Equation (39)

In addition, the following equations (40) and (41) are established as for a torque $T_1$ generated in the pulley-side shaft 82B of the speed reducer 82 when an original spring constant of the flat spiral spring 24 is k and a rotation angle of the free end relative to the fixed end of the flat spiral spring 24 is θ'.

$\tau_1 = k\theta'$ Equation (40)

$n(\theta - \theta_0) = \theta'$ Equation (41)

The following equation (42) is obtained by the above equations (40) and (41), and the following equation (43) can be obtained by the following equation (42) and the above equation (39).

$\tau_1 = kn(\theta - \theta_0)$ Equation (42)

$\tau = \eta_R n \cdot kn(\theta - \theta_0) = \eta_R n^2 k(\theta - \theta_0)$ Equation (43)

The following equation (44) can be obtained by the above equations (43) and (38).

$k_R = \eta_R n^2 k$ Equation (44)

Here, the following equation (45) is established when it is assumed that the fixed end of the flat spiral spring 24 moves (pivots) by $\theta_1$, and the following equation (46) can be obtained by the following equation (45) and the above equation (40).

$\theta' = n(\theta - \theta_0) - \theta_1$ Equation (45)

$\tau_1 = k[n(\theta - \theta_0) - \theta_1]$ Equation (46)

In addition, the following equation (47) can be obtained by the above equation (39) and the above equation (46). Moreover, the following equation (48) can be obtained by the following equation (47) and the above equation (38).

$$\tau = \eta_R n \cdot k[n(\theta - \theta_0) - \theta_1]$$
$$= \eta_R n^2 k\{1 - \theta_1 / [n(\theta - \theta_0)]\}(\theta - \theta_0)$$ 
Equation (47)

$$k_R = \eta_R n^2 k\{1 - \theta_1 / [n(\theta - \theta_0)]\}$$ Equation (48)

Here, the following equation (49) is established when a mass of a load (the first swinging portion 93 integrated with the second swinging portion 95 and the second pivoting portion 94) is m, an inertia moment of the load is J, a viscosity coefficient of the load is d, a distance from the center of the swinging of the first swinging portion 93 to the center of the gravity of the load is 1 (see FIG. 15), and sin θ≈θ. Note that since the inertia moment J and the distance 1 to the center of the gravity change depending on the posture of the load (the first swinging portion 93 integrated with the second swinging portion 95 and the second pivoting portion 94), their values are calculated in advance to be used.

$\tau = J\ddot{\theta} + d\dot{\theta} k_R(\theta - \theta_0) + mgl\theta$ Equation (49)

In addition, a total sum E of energy when gravity is applied in the motion direction of the swinging is provided by the following equation (50).

$$E = \frac{1}{2}J\dot{\theta}^2 + \frac{1}{2}k_R(\theta - \theta_0)^2 + mgl\theta$$ Equation (50)

Here, a condition for minimizing the total sum E of the energy in the above equation (50) is shown in the following equation (51), and the following equations (52) and (53) can be obtained by the following equation (51).

$$\frac{dE}{dt} = J\dot{\theta}\ddot{\theta} + k_R(\theta - \theta_0)\dot{\theta} + mgl\dot{\theta}$$
$$= \{J\ddot{\theta} + k_R(\theta - \theta_0) + mgl\}\dot{\theta}$$
$$= 0$$
Equation (51)

$J\ddot{\theta} + k_R(\theta - \theta_0) + mgl = 0$ Equation (52)

$$k_R = -\frac{J\ddot{\theta} + mgl}{\theta - \theta_0}$$ Equation (53)

When the swinging motion produces a substantially sine wave about $\theta_0$, the following equation (54) is established. Then, the following equation (55) can be obtained by the following equation (54) and the above equation (53).

$\theta = \theta_0 + A \sin \omega t$ Equation (54)

$k_R = [(JA\omega^2 \sin \omega t - mgl)/(A \sin \omega t)] = J\omega^2 - mgl/(A \sin \omega t)$ Equation (55)

As described above, the angle $\theta_1$ (corresponding to the offset angle θs shown in FIG. 9) of the position of the fixed end 24A of the flat spiral spring 24 is adjusted so as to satisfy the above equation (48) in real time with respect to the swinging angle θ of the first swinging portion 93. Thus, the consumption energy of the electric motor 84M may be minimized.

It is possible to make various modifications, additions, and deletions to structures, configurations, shapes, appearances, and the like of the swinging joint device (the walking-ability assisting device), the walking assisting device, the conveying device, the manipulator, and the walking-ability assisting device of the invention, without departing from the scope of the invention.

The application of the swinging joint device (the walking-ability assisting device) described in the embodiment is not limited to a walking assisting device used to assist the swinging motion (such as walking and running) of the lower limb of a user, but the swinging joint device (the walking-ability assisting device) may be applied to various objects such as conveying devices and manipulators that perform cyclic swinging motion.

The swinging and rotating motion of the electric motor 11, the electric motor 31, the vertical driving actuator 74M, and the electric motor 84M is transmitted to the femoral swinging arm 13, the crus swinging arm 33, the pinion 71B, and the first swinging portion 93 by the pulleys and the belts in the embodiment, but may be transmitted using gears, a link mechanism, and the like instead of the pulleys and the belts.

In addition, the embodiment describes an example in which the flat spiral spring 24 is indirectly connected to the femoral swinging arm 13 (the pulley 15) with the transmission 25 provided between the femoral swinging arm 13 (the pulley 15) and the flat spiral spring 24, but the femoral swinging arm 13 (the pulley 15) and the flat spiral spring 24 may be directly connected to each other without the transmission 25. Similarly, the speed reducer 72 and the speed reducer 82 may be omitted.

In addition, the embodiment describes an example in which the flat spiral spring 24 is used as an elastic body, but the flat spiral spring 24 may be replaced by various elastic bodies. For example, other elastic bodies such as a spirally-wound expansion/contraction spring, a plate spring, and a wave spring may be used. Elastic bodies using elastomer such as rubber and a resin, liquid such as oil, or gas may be used. It is possible to change the elastic body according to a motion amount (movement) of an object whose energy is to be reserved or a reserved energy amount. When an energy amount to be reserved is relatively small, it is effective to use elastomer. Further, for a user's action such as walking and running, it is effective to use a flat spiral spring in terms of its relatively-large energy reservation amount, a magnitude of a spring constant (rigidity) and the like, adjustment easiness, and the like. Furthermore, a flat spiral spring is superior in terms of cost.

Hereinafter, a description will be given, with reference to the drawings, of a seventh embodiment as an embodiment for carrying out the invention. Note that when respective figures describe X, Y, and Z axes, the X, Y, and Z axes are orthogonal to each other. Unless otherwise stated, a Z-axis direction indicates a vertically-upward direction, an X-axis direction indicates a front direction relative to a user (user wearing a swinging joint device), and a Y-axis direction indicates a left direction relative to the user. Note that in the specification, a "femoral swinging arm 13" shown in FIG. 17 corresponds to a "first swinging arm", and a "crus swinging arm 33" shown in FIG. 17 corresponds to a "second swinging arm." In addition, a "rotation angle detection portion 11S" shown in FIG. 17 corresponds to a "first angle detection portion," and a "rotation angle detection portion 31S" shown in FIG. 17 corresponds to a "second angle detection portion." Moreover, an "electric motor 11" shown in FIG. 17 corresponds to a "first driving portion," an "electric motor 31" shown in FIG. 17 corresponds to a "second driving portion," and an "electric motor 21" shown in FIG. 17 corresponds to a "speed ratio adjustment motor." Further, in an example of the following description, a driving shaft member 6 is a protruding member. However, the driving shaft member 6 may be a protruding shaft or a recessed (hole-shaped) portion that supports a shaft. Accordingly, when the description says "about the driving shaft member 6," it indicates "about a driving axis line 6J representing the central axis of the driving shaft member 6." A "transmission 25" and the "electric motor 21" correspond to an "apparent spring constant variable portion." "Rigidity of the femoral swinging arm" indicates a torque per unit angle displacement required for swinging the femoral swinging arm 13. Furthermore, a "crus relaying arm 34" and a "crus arm 35" correspond to a "swinging link member."

Figure 17:
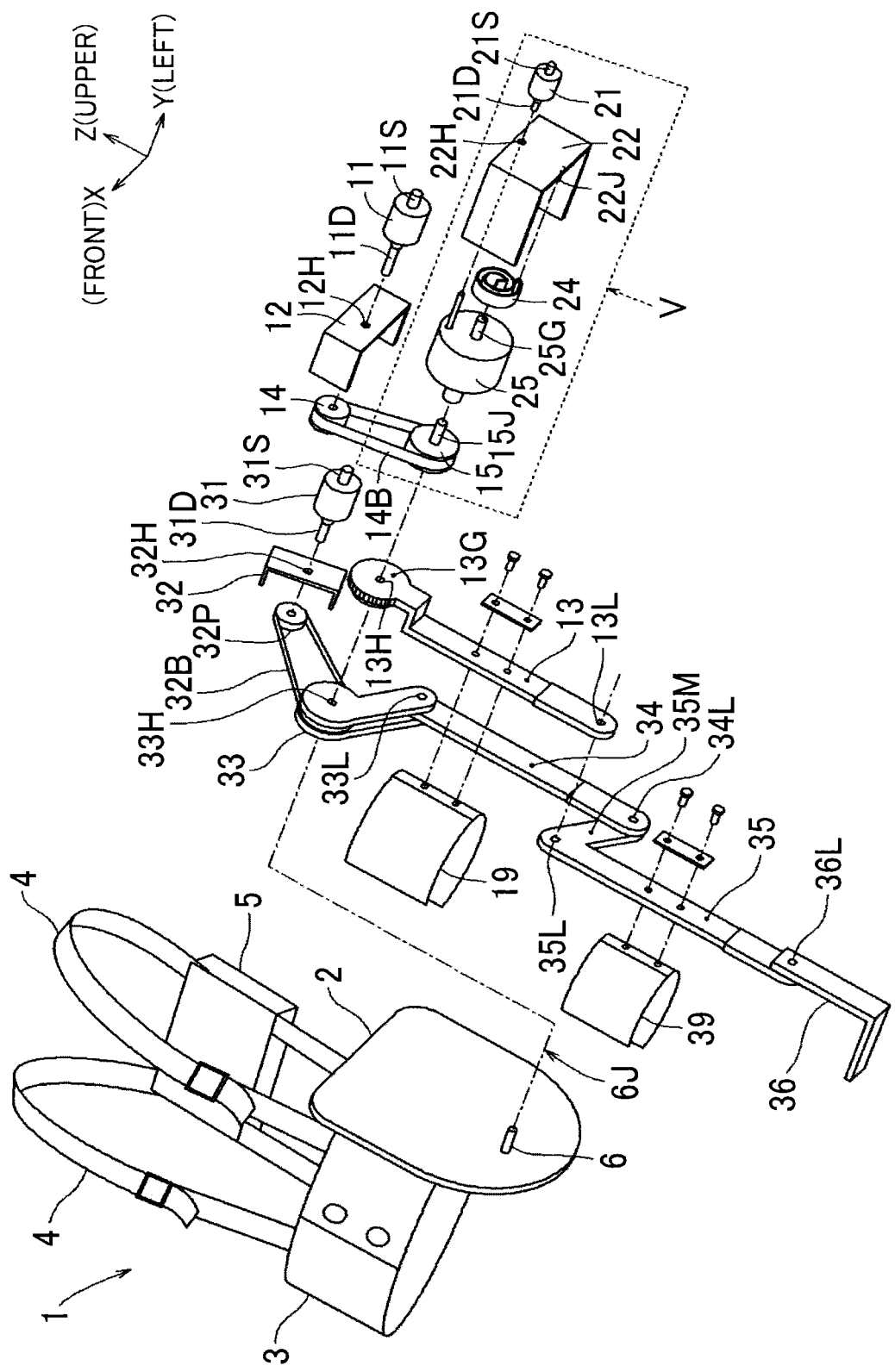
FIG. 17 is an exploded perspective view illustrating the schematic shapes and the assembling positions of respective constituents constituting a swinging joint device of a seventh embodiment.
Figure 18:
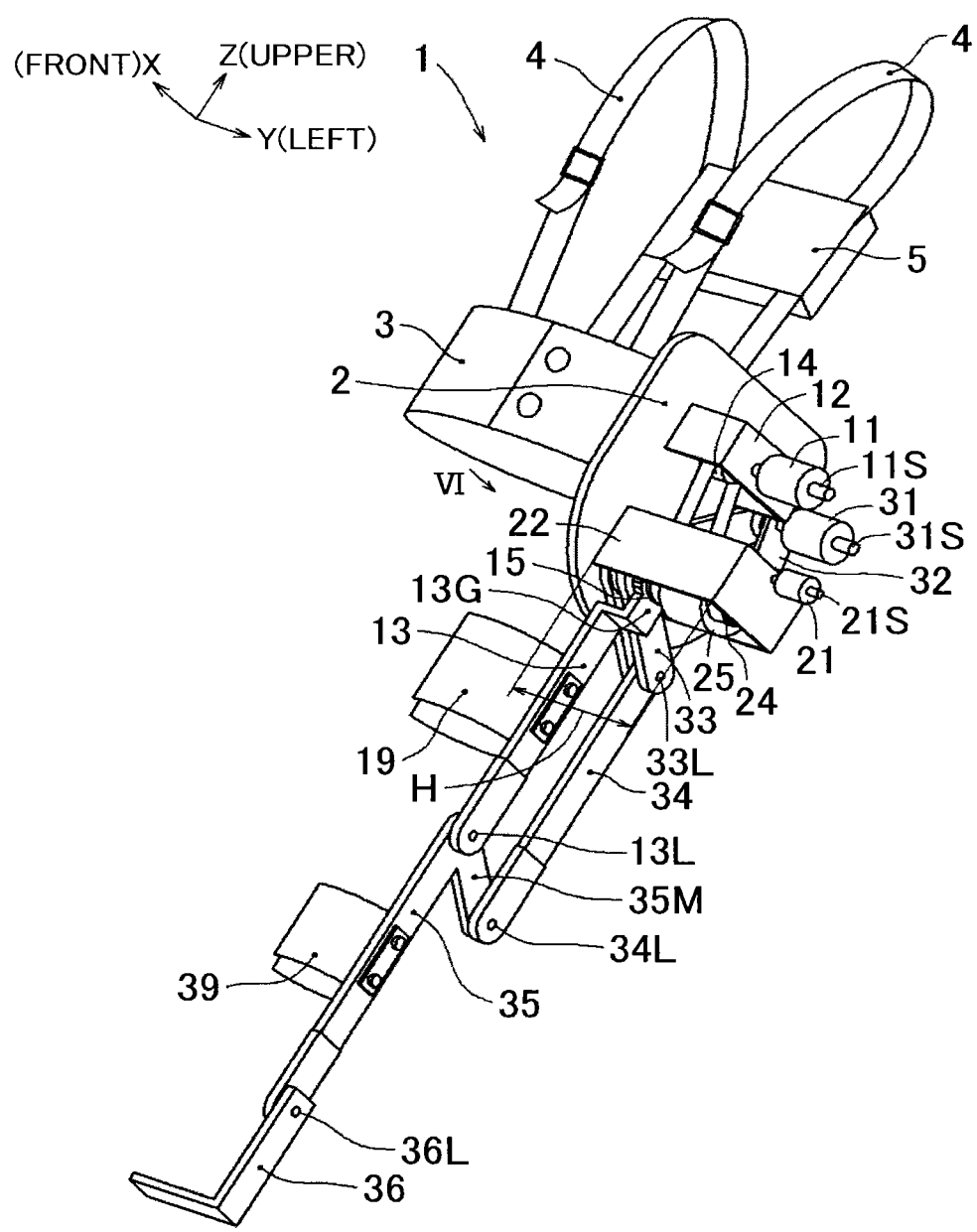
FIG. 18 is a perspective view of the swinging joint device in which the constituents shown in FIG. 17 are assembled together.
Figure 19:
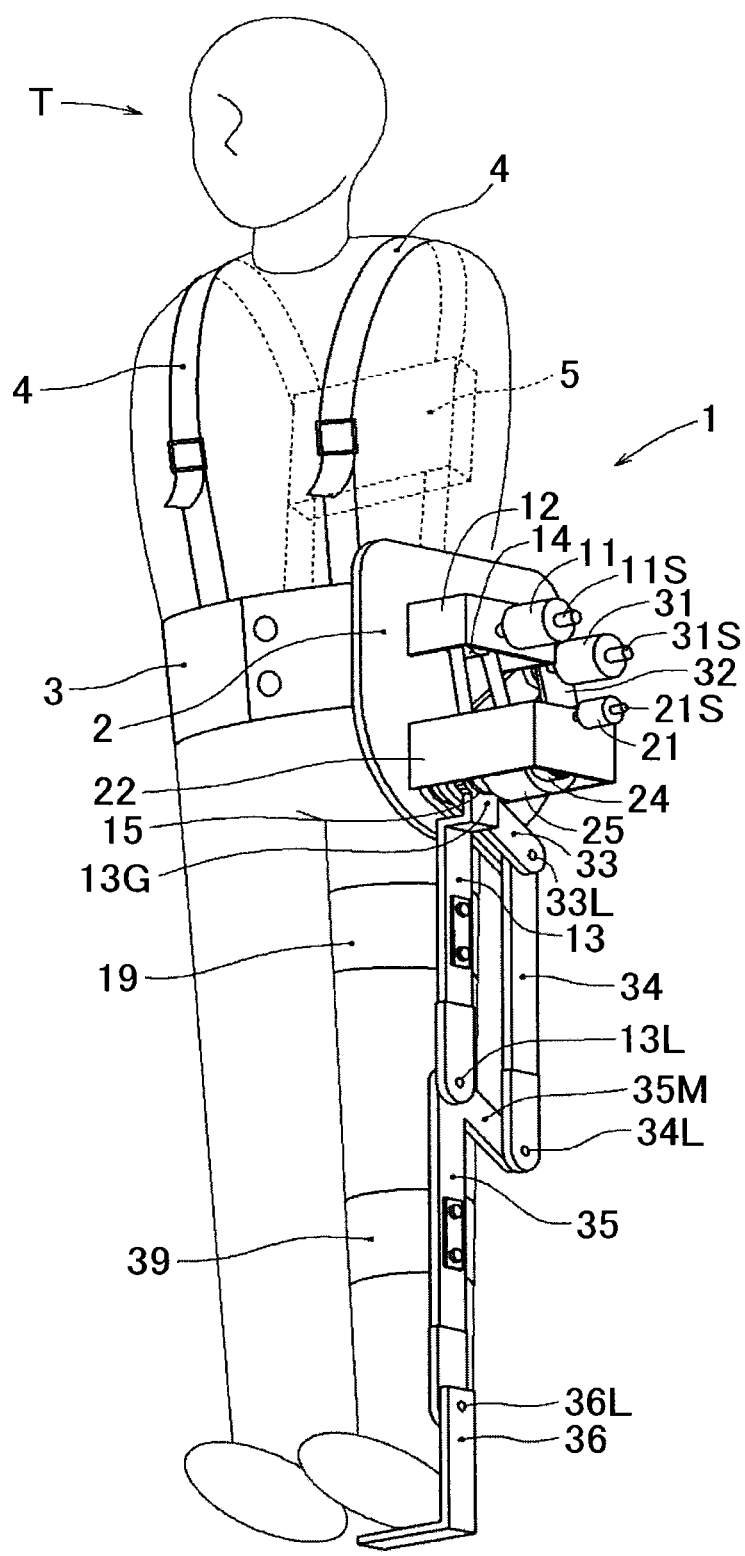
FIG. 19 is a view illustrating a state in which the swinging joint device shown in FIG. 18 is attached to a user (whose arms are omitted)
Figure 20:
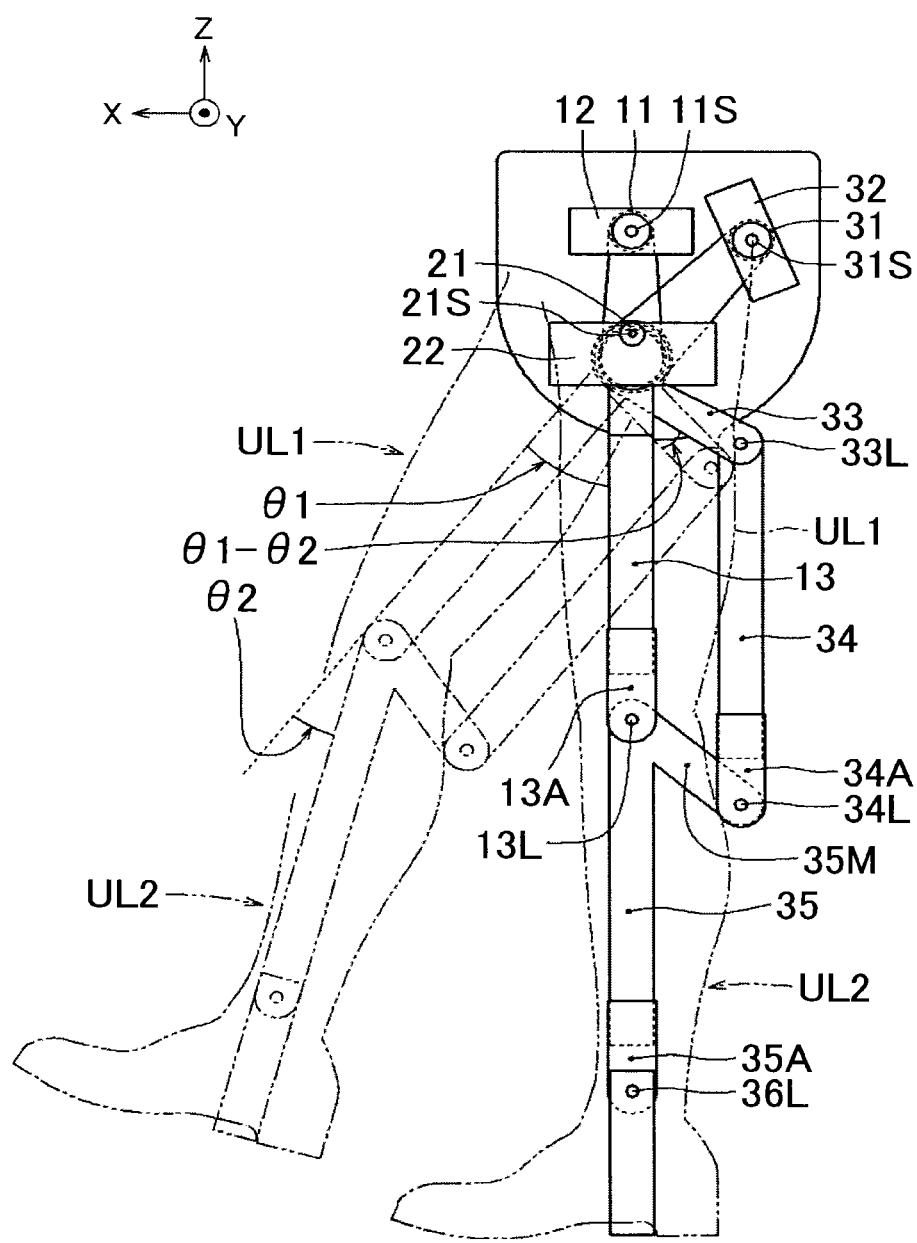
FIG. 20 is a view illustrating a swinging state of a femoral swinging arm (first swinging arm) and a swinging example of a crus arm (second swinging arm)

Hereinafter, a description will be given of the entire configuration (FIGS. 17 to 20) of a swinging joint device 1 of the seventh embodiment. The swinging joint device 1 of the seventh embodiment is attached to one leg (the left leg in the seventh embodiment) of a user to assist a user's action such as walking and running. As shown in FIG. 17, the swinging joint device 1 is constituted by a user attachment portion indicated by symbols 2, 3, 4, 5, 6, and the like, a femoral swinging portion indicated by symbols 11, 12, 14, 14B, 15, 13, 19, and the like, a rigidity adjustment portion indicated by symbols 21, 22, 24, 25, and the like, and a crus swinging portion indicated by symbols 31, 32, 32P, 32B, 33, 34, 35, 36, 39, and the like. Note that FIG. 17 is an exploded perspective view showing the shapes, the assembling positions, and the like of the respective constituents of the swinging joint device 1, and FIG. 18 shows the swinging joint device 1 in a state in which the constituents are assembled together. In addition, FIG. 19 shows a state in which a user wears the swinging joint device 1, and FIG. 20 shows a swinging example of the femoral swinging arm 13 and the crus swinging arm 33. Portions and members that are the same as or equivalent to those of the swinging joint device 1 of the first embodiment are indicated by the same reference numerals and signs, and descriptions thereof will be omitted.

Hereinafter, a description will be given of a rigidity adjustment portion (FIGS. 17 to 19 and FIGS. 21 to 23) constituted by the electric motor 21, the bracket 22, the flat spiral spring 24, the transmission 25, and the like. The bracket 22 is a member that fixes the electric motor 21 to the base portion 2. The bracket 22 has the through-hole 22H into which the rotation shaft of the electric motor 21 is inserted, and is fixed to the base portion 2. In addition, as shown in FIGS. 17 and 22, the through-hole 13H of the disc portion 13G of the femoral swinging arm 13, the pulley shaft member 15J of the pulley 15, the shaft 25A of the transmission 25, and the central axis of the flat spiral spring 24 are disposed to be coaxial with the driving axis line 6J. In addition, as shown in FIGS. 21 and 22, a transmission adjustment screw 21N, the through-hole 22H of the bracket 22, and the speed reducer 21D of the electric motor 21 are disposed to be coaxial with an axis 21J representing the axis of the transmission adjustment screw 21N.

Figure 21:
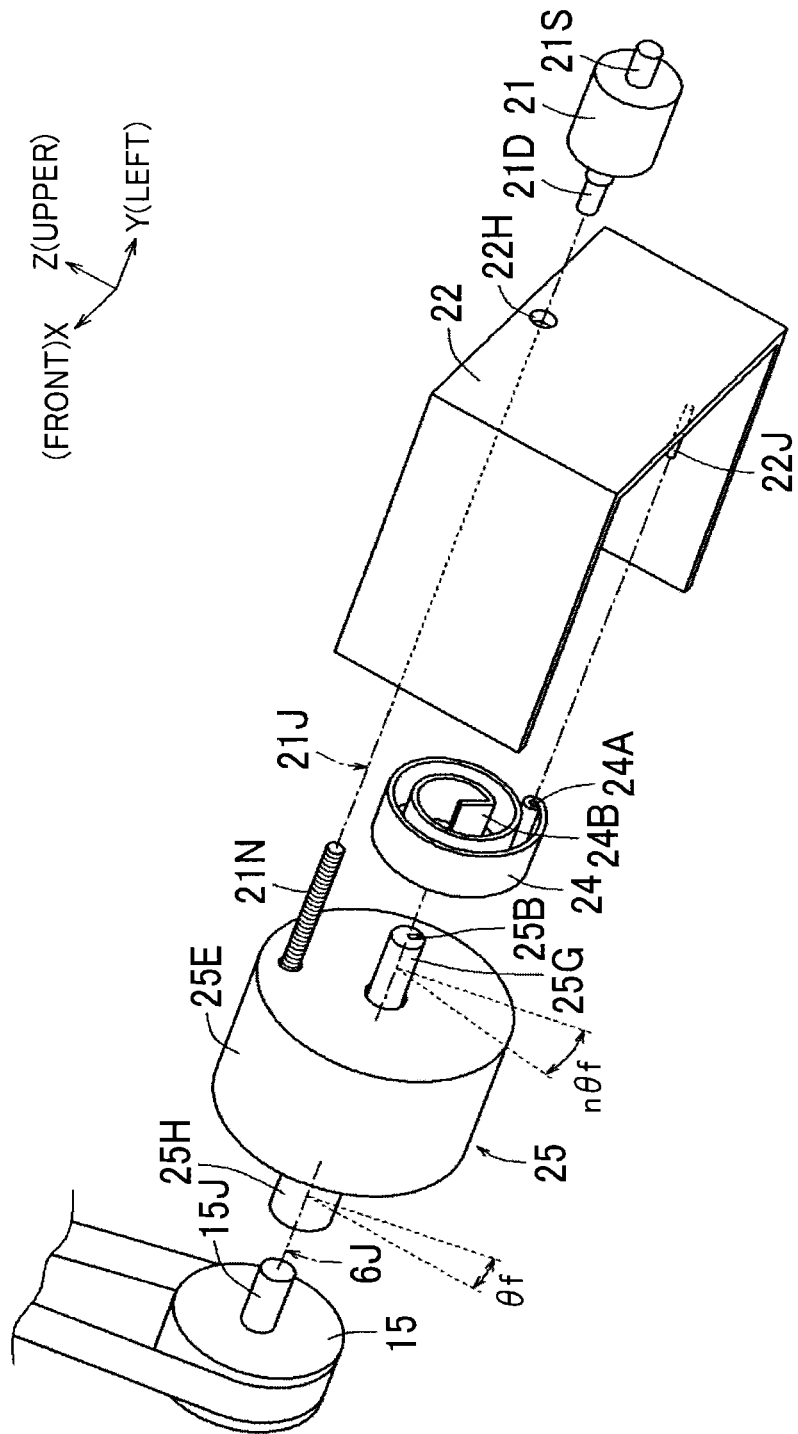
FIG. 21 is an enlarged view of a V part in FIG. 17 and an exploded perspective view illustrating the configurations of a flat spiral spring and an apparent spring constant variable portion.
Figure 22:
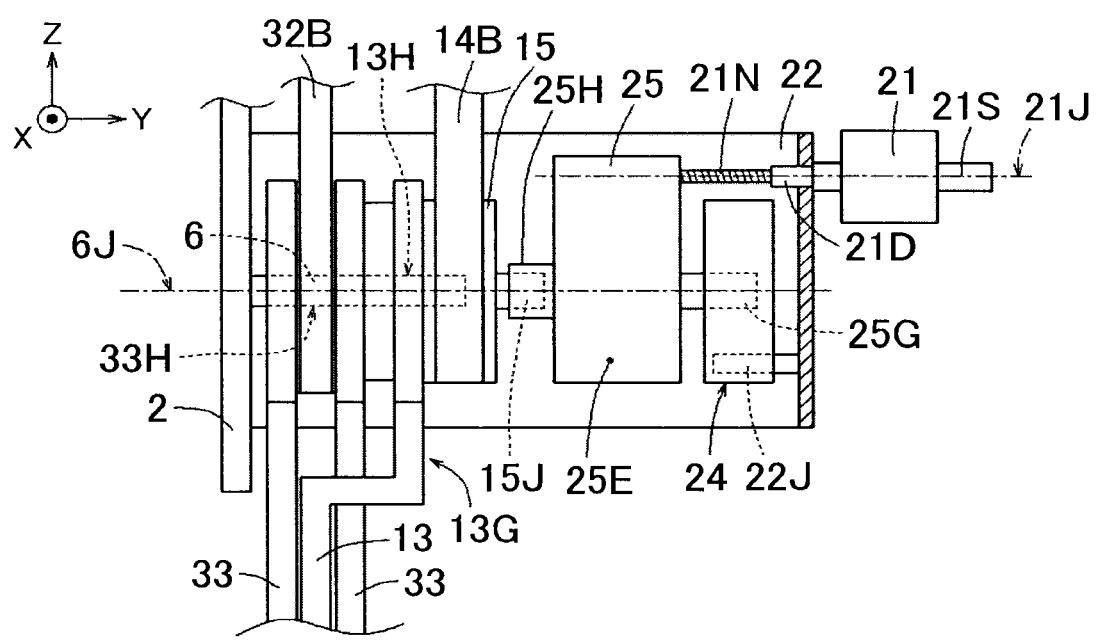
FIG. 22 is a view seen from a VI direction in FIG. 18 and a view illustrating the arrangements of members provided to be coaxial with a driving axis line of a driving shaft member.
Figure 23:
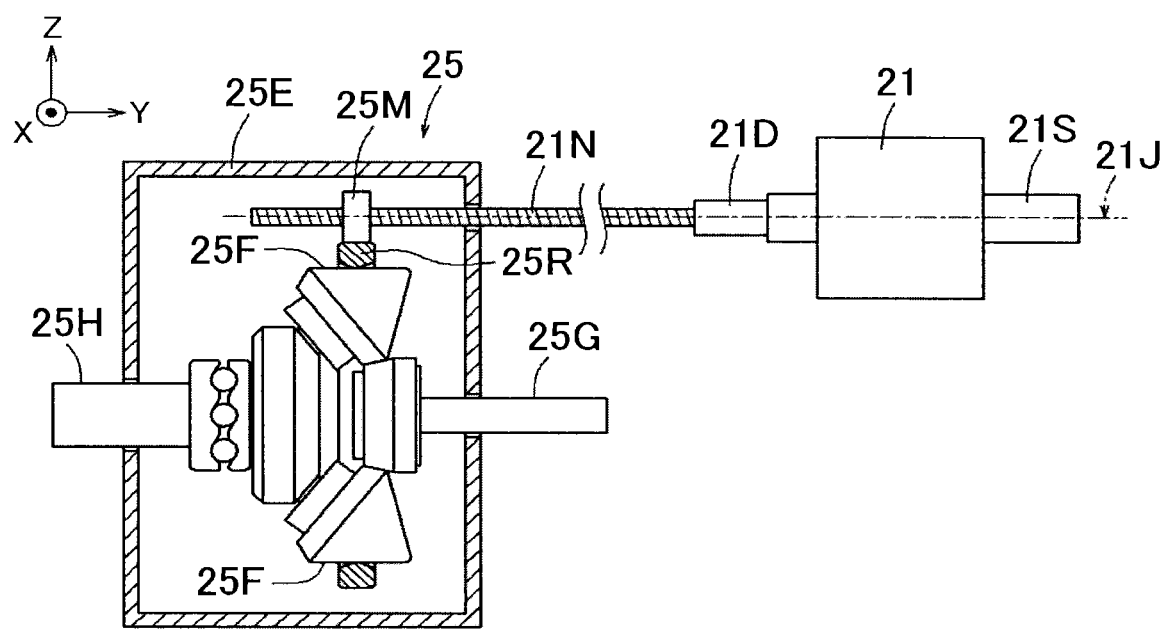
FIG. 23 is a view illustrating an example of an electric motor (speed ratio adjustment motor) and a transmission constituting a transmission portion.

As shown in FIGS. 21 and 23, in the transmission 25, an input/output shaft 25H is connected to the pulley shaft member 15J of the pulley 15 fixed to the disc portion 13G of the femoral swinging arm 13. The transmission 25 outputs an output pivoting angle nθ, which is obtained by multiplying an input pivoting angle θ input to the input/output shaft 25H on one side by n times, as a pivoting angle of an input/output shaft 25G on the other side, based on a variable speed ratio (n) adjusted by the electric motor 21. In addition, the transmission 25 outputs an output pivoting angle θ/n, which is obtained by multiplying an input pivoting angle θ input to the input/output shaft 25G on the other side by 1/n times, as a pivoting angle of the input/output shaft 25H on the one side. Accordingly, when the input/output shaft 25G is caused to pivot by a pivoting angle θb due to an urging torque from the flat spiral spring 24, the transmission 25 pivots the pulley shaft member 15J by a pivoting angle θb·(1/n). Moreover, as shown in FIG. 21, the input/output shaft 25G has the spring free-end insertion groove 25B that serves as a groove extending in the direction of the driving axis line 6J for fixing the side of the free end 24B of the flat spiral spring 24. Note that the transmission 25 is disposed in a swinging-angle transmission path through which a swinging angle of the femoral swinging arm 13 is transmitted to the flat spiral spring 24.

FIG. 23 shows a structural example of the transmission 25. The transmission 25 includes the input/output shaft 25H, the input/output shaft 25G, a plurality of transmission cones 25F, a transmission ring 25R, and the like inside a case 25E. A swinging angle of the input/output shaft 25H is transmitted to the input/output shaft 25G via the transmission cones 25F having a substantially cone shape, and a swinging angle of the input/output shaft 25G is transmitted to the input/output shaft 25H via the transmission cones 25F. The transmission ring 25R has an annular shape to contact the transmission cones 25F and is connected to a nut 25M. When the transmission adjustment screw 21N is rotated by the speed reducer 21D of the electric motor 21, the nut 25M moves in the longitudinal direction of the transmission adjustment screw 21N and a position of the transmission ring 25R (a position in the Y-axis direction in the example of FIG. 23) relative to the transmission cones 25F moves. Then, the postures of the transmission cones 25F change, and thus, a speed ratio (n) of the input/output shaft 25G relative to the input/output shaft 25H changes.

As the flat spiral spring 24, an elastic body such as a spring member is spirally wound about a prescribed axis. As shown in FIG. 21, the flat spiral spring 24 has the free end 24B at one end serving as an end positioned near the central area of its winding and has the fixed end 24A at the other end serving as an end positioned distant from the central area of the winding. Note that the free end 24B is fixed to the spring free-end insertion groove 25B of the input/output shaft 25G and the fixed end 24A is fixed to a spring supporting body 22J of the bracket 22 in FIG. 21. For example, the spring supporting body 22J is a shaft-shaped member extending along the driving axis line 6J and is inserted into a cylindrical portion formed at the position of the fixed end 24A of the flat spiral spring 24. Further, the spring supporting body 22J fixes the position of the fixed end 24A of the flat spiral spring 24 relative to the bracket 22.

The speed reducer 21D is attached to the distal end of the electric motor 21, and is attached to the transmission adjustment screw 21N. In addition, the speed reducer 21D is inserted into the through-hole 22H of the bracket 22, the electric motor 21 is fixed to the bracket 22, and the bracket 22 is fixed to the base portion 2. Moreover, the electric motor 21 receives power together with driving signals from the battery and the control portion accommodated in the control unit 5. Further, the electric motor 21 rotates the transmission adjustment screw 21N about the axis of the transmission adjustment screw 21N relative to the transmission 25 to adjust a position of the transmission ring 25R of the transmission 25 and adjust a speed ratio of the transmission 25. Furthermore, the electric motor 21 is provided with the rotation angle detection portion 21S such as an encoder. The rotation angle detection portion 21S outputs a signal corresponding to a rotation angle of the shaft of the electric motor 21, to the control portion. Meanwhile, the control portion is capable of detecting a rotation angle of the speed reducer 21D based on a detection signal from the rotation angle detection portion 21S and a speed reduction ratio of the speed reducer 21D, and is capable of detecting a speed ratio based on a position of the transmission ring 25R. Note that the bracket 22 may be provided with a position detection portion (position sensor) that detects a position of the transmission ring 25R in the Y-axis direction relative to the bracket 22. In addition, the electric motor 21 is not an idling motor (i.e., the electric motor 21 is a motor that does not idle), a pivoting angle position of the speed reducer 21D is maintained even when the electric motor 21 is not energized, and thus a speed ratio of the transmission 25 is maintained.

Figure 24:
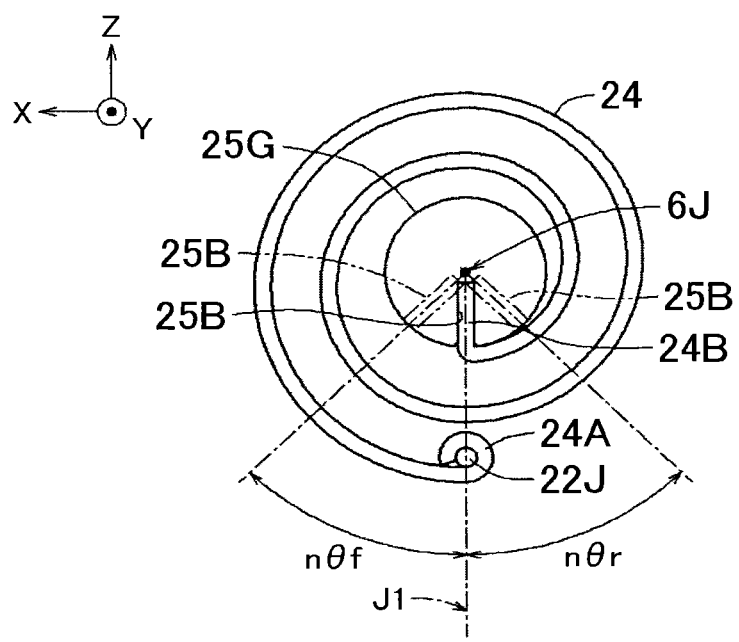
FIG. 24 is a view illustrating a state in which a swinging angle nθf in a clockwise direction and a swinging angle nθr in a counterclockwise direction relative to a reference position at which a swinging angle of the femoral swinging arm is zero are input to the flat spiral spring.

Hereinafter, a description will be given of the position (FIG. 24) of the fixed end 24A of the flat spiral spring 24. FIG. 24 shows an example of a case in which a user T shown in FIG. 19 is in his/her upright posture, a swinging angle of the femoral swinging arm 13 is zero, and an urging torque of the flat spiral spring 24 is zero. At the position of the fixed end 24A of the flat spiral spring 24 in the example of FIG. 24, neither an urging torque in a clockwise direction about the driving axis line 6J nor an urging torque in a "counterclockwise" direction about the driving axis line 6J is generated in the free end 24B. Further, a reference line J1 shown in FIG. 24 is a virtual line passing through the driving axis line 6J and the spring free-end insertion groove 25B when a swinging angle of the femoral swinging arm 13 is zero and an urging torque of the flat spiral spring 24 is zero, and indicates the reference pivoting angle position of the input/output shaft 25G. Note that although FIG. 24 shows an example in which the fixed end 24A exists ahead of the spring free-end insertion groove 25B in the depth direction of the spring free-end insertion groove 25B, and the spring free-end insertion groove 25B and the fixed end 24A are positioned on the reference line J1, the position of the fixed end 24A is not limited to this position. The reference line J1 is a line representing a reference position when a swinging angle of the femoral swinging arm 13 is zero and an urging torque of the flat spiral spring 24 is zero.

In addition, a swinging angle nθf shown in FIG. 24 indicates a swinging angle input to the free end 24B of the flat spiral spring 24 when the femoral swinging arm 13 swings in the clockwise direction at a swinging angle θf. When the femoral swinging arm 13 swings in the clockwise direction at the swinging angle θf with a speed ratio (n) of the transmission 25, the input/output shaft 25G of the transmission 25 swings in the clockwise direction at a swinging angle nθf. When the swinging angle nθf in the clockwise direction is input to the free end 24B of the flat spiral spring 24, the flat spiral spring 24 generates an urging torque (k*nθf) in the "counterclockwise" direction with a spring constant k of the flat spiral spring 24.

Moreover, the swinging angle nθr shown in FIG. 24 indicates a swinging angle input to the free end 24B of the flat spiral spring 24 when the femoral swinging arm 13 swings in the "counterclockwise" direction at a swinging angle θr. When the femoral swinging arm 13 swings in the "counterclockwise" direction at the swinging angle θr with the speed ratio (n) of the transmission 25, the input/output shaft 25G of the transmission 25 swings in the "counterclockwise" direction at the swinging angle nθr. When the swinging angle nθr in the "counterclockwise" direction is input to the free end 24B of the flat spiral spring 24, the flat spiral spring 24 generates an urging torque (k*nθr) in the clockwise direction with the spring constant k of the flat spiral spring 24.

Figure 25:
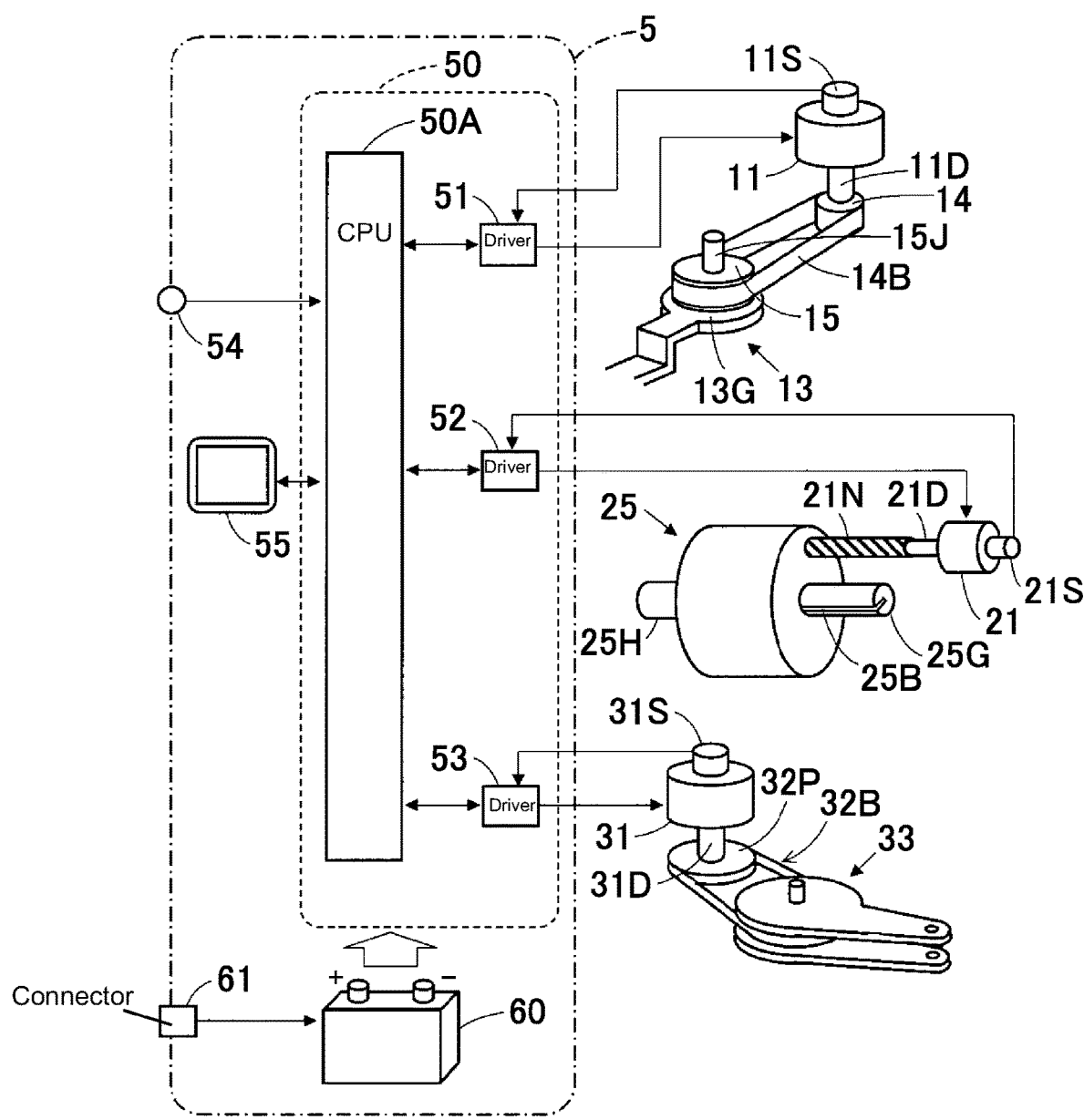
FIG. 25 is a view illustrating the input/output to/from a control portion.

Next, a description will be given of the input/output of a control portion 50 with reference to FIG. 25. The control unit 5 accommodates the control portion 50 and a battery 60. In addition, the control unit 5 includes a start switch 54, a touch panel 55 serving as an input/output portion, a connector 61 for charging the battery 60, and the like. Moreover, the control portion 50 (the control unit) includes a central processing unit (CPU) 50A, motor drivers 51, 52, and 53, and the like. Note that although the control portion 50 also includes a storage unit that stores a program for running the processing of the control portion 50, various measurement results, and the like, the storage unit is not shown in the figure.

As will be described later, the control portion 50 calculates a target swinging cycle and a target swinging angle to swing the femoral swinging arm 13 and outputs a driving signal to the electric motor 11 via the motor driver 51. The electric motor 11 swings the speed reducer 11D based on the driving signal from the control portion 50 and swings the femoral swinging arm 13 at a prescribed cycle and a prescribed angle via the pulley 14, the belt 14B, and the pulley 15. In addition, a rotation speed and a rotation amount of the shaft of the electric motor 11 are detected by the rotation angle detection portion 11S, and a detection signal is input to the CPU 50A via the motor driver 51 while being input to the motor driver 51. The CPU 50A performs feedback control such that an actual swinging cycle and an actual swinging angle of the femoral swinging arm 13 based on the detection signal from the rotation angle detection portion 11S become closer to (i.e., approach) the target swinging cycle and the target swinging angle.

In addition, as will be described later, the control portion 50 calculates a speed ratio of the transmission 25 such that the apparent spring constant of the flat spiral spring 24 seen from the femoral swinging arm 13 has an optimum value, and outputs a driving signal to the electric motor 21 via the motor driver 52. Based on the driving signal from the control portion 50, the electric motor 21 pivots the transmission adjustment screw 21N via the speed reducer 21D. In addition, a rotation speed and a rotation amount of the shaft of the electric motor 21 are detected by the rotation angle detection portion 21S, and a detection signal is input to the CPU 50A via the motor driver 52 while being input to the motor driver 52. The CPU 50A performs feedback control such that an actual speed ratio of the transmission 25 based on the detection signal from the rotation angle detection portion 21S becomes closer to (i.e., approaches) a target rigidity speed ratio. The actual speed ratio of the transmission 25 is achieved by the transmission adjustment screw 21N.

As will be described later, the control portion 50 calculates a target swinging cycle and a target swinging angle to swing the crus swinging arm 33 and outputs a driving signal to the electric motor 31 via the motor driver 53. Based on the driving signal from the control portion 50, the electric motor 31 swings the crus swinging arm 33 at a prescribed cycle and a prescribed angle via the speed reducer 31D, the pulley 32P, and the belt 32B. In addition, a rotation speed and a rotation amount of the shaft of the electric motor 31 are detected by the rotation angle detection portion 31S, and a detection signal is input to the CPU 50A via the motor driver 53 while being input to the motor driver 53. The CPU 50A performs feedback control such that an actual swinging cycle and an actual swinging angle of the crus swinging arm 33 based on the detection signal from the rotation angle detection portion 31S become closer to (i.e., approach) the target swinging cycle and the target swinging angle.

The start switch 54 is a switch for starting the control portion 50. In addition, the touch panel 55 is a device that is used to input a user's height, weight, and the like, and that displays a setting state and the like. Moreover, the connector 61 for charging is a connector to which a charging cable is connected to charge the battery 60.

Next, a description will be given of the processing procedure of the control portion 50 with reference to a flowchart shown in FIG. 26. When a user operates the start button of the control unit (step S10), the control portion proceeds to step S15.

In step S15, the control portion is on standby for the input of user's initial settings via the touch panel. After confirming the input of a user's height and weight, the control portion proceeds to step S20. Note that when the user's input is not confirmed even after the elapse of a prescribed time, the control portion sets, for example, a default (preset) standard height and weight and proceeds to step S20.

In step S20, the control portion measures a user's walking (or running) state without energizing the electric motors 11, 21, and 31 for a prescribed period and stores detection signals from the rotation angle detection portions 11S and 31S in the storage unit as measurement data corresponding to a measurement time. The shafts of the electric motors 11 and 31 are configured to idle at a non-energizing time. Note that the shaft of the electric motor 21 is configured to be locked without idling at the non-energizing time. A pivoting angle of the transmission adjustment screw 21N achieved by the electric motor 21 is not changed, and thus, the speed ratio is fixed. After collecting the measurement data for, for example, a prescribed number of steps or a prescribed time, the control portion proceeds to step S25.

In step S25, the control portion calculates a swinging angle (or a swinging amplitude) of the femoral swinging arm from the measurement data based on the detection signal from the rotation angle detection portion 11S and calculates a walking cycle (or a swinging cycle) from an angular speed and an angular acceleration of the femoral swinging arm. In addition, the control portion similarly calculates a swinging angle (or a swinging amplitude) of the crus swinging arm from the measurement data based on the detection signal from the rotation angle detection portion 31S and calculates a walking cycle (or a swinging cycle) from an angular speed and an angular acceleration of the crus swinging arm. Then, the control portion proceeds to step S30.

In step S30, the control portion calculates a target rigidity speed ratio as optimum joint rigidity based on the swinging angle and the swinging cycle of the femoral swinging arm calculated in step S25 and the user's height and weight and the like input in step S15. After that, the control portion proceeds to step S35. Note that a method for calculating the target rigidity speed ratio will be described in detail later.

In step S35, the control portion controls the electric motor 21 to set the speed ratio of the transmission 25 at the target rigidity speed ratio calculated in step S30. After that, the control portion proceeds to step S40.

In step S40, the control portion calculates the pattern of assisting the femoral part of a user (the pattern of outputting a driving signal to the electric motor 11, and the like) and the pattern of assisting the crus part of the user (the pattern of outputting a driving signal to the electric motor 31) based on the swinging angle and the swinging cycle of the femoral swinging arm and the swinging angle and the swinging cycle of the crus swinging arm calculated in step S25, an output voltage of the battery, and the like. After that, the control portion proceeds to step S45.

In step S45, the control portion starts outputting driving signals to the electric motors 11 and 31 based on the assist patterns calculated in step S40 to swing the femoral swinging arm 13 and the crus swinging arm 33 and assists the user's walking (or running) action such that the user's walking (or running) action continues. After that, the control portion proceeds to step S50. Note that the output of the driving signals to the electric motors 11 and 31 is continued even after the control portion transits to other steps.

In step S50, the control portion stores, as in the measurement of step S20, detection signals from the rotation angle detection portions 11S and 31S in the storage unit as measurement data corresponding to a measurement time while operating the electric motors 11 and 31 and assisting the user's walking (or running) action. After that, the control portion proceeds to step S55. Note that the collection of the measurement data is continued even after the control portion transits to other steps.

In step S55, the control portion determines whether the user wants to stop assisting the walking (or running) action based on the measurement data collected in step S50. When determining that the user wants to stop assisting the walking (or running) action (Yes), the control portion stops outputting the driving signals to the electric motors 11 and 31 to end the processing. On the other hand, when determining that the user does not want to stop assisting the walking (or running) action (No), the control portion returns to step S25.

Hereinafter, a description will be given of a method for calculating a target rigidity speed ratio, i.e., a target rigidity speed ratio with respect to a swinging angle θf of the femoral swinging arm 13 in the clockwise direction. A description will be given of a procedure for calculating a target rigidity speed ratio performed in step S30 of the flowchart shown in FIG. 26, i.e., an example of a case in which the femoral swinging arm 13 swings in the clockwise direction at the swinging angle θf. In this case, a swinging angle nθf is input to the input/output shaft 25G of the transmission 25 in the clockwise direction with a speed ratio (n) of the transmission 25. In addition, when efficiency of the transmission 25 is η, an apparent spring constant of the flat spiral spring 24 seen from the side of the femoral swinging arm 13 is k1, a spring constant of the flat spiral spring 24 seen from the side of the spring supporting body 22J is k (an original spring constant of the flat spiral spring 24), and a torque generated when the femoral swinging arm 13 swings is τ, the following equation (1) is established.

$$\tau = k1 \cdot \theta f = \eta \cdot k \cdot n^2 \theta f \qquad \text{Equation (1)}$$

When the above equation (1) is transformed, the apparent spring constant k1 of the flat spiral spring 24 seen from the side of the femoral swinging arm 13 can be determined by the following equation (2). In addition, the following equation (3) can be obtained when the following equation (2) is transformed.

$$k1 = \eta \cdot n^2 \cdot k \qquad \text{Equation (2)}$$

$$n = \sqrt{[k1/(\eta \cdot k)]} \qquad \text{Equation (3)}$$

For example, it is evident from the above equation (2) that a current speed ratio n is changed to $\sqrt{2} \cdot n$, which is $\sqrt{2}$ times the current speed ratio n, when the apparent spring constant k1 of the flat spiral spring 24 seen from the side of the femoral swinging arm 13 is doubled.

Here, when a walking frequency (a swinging frequency of the femoral swinging arm) of a user is f and an angular frequency (angular speed) is ω at this time, the following equation (4) is established. The walking frequency f can be determined based on a measured cycle of user's walking (or running). Accordingly, a value ω in the following equation (4) can be determined.

$$\omega = 2 \cdot \pi \cdot f \qquad \text{Equation (4)}$$

In addition, as described above, an apparent spring constant of the flat spiral spring 24 seen from the side of the femoral swinging arm 13 is k1. Moreover, an inertia moment about the driving axis line 6J in a swinging object including the lower limb of a user, the femoral swinging arm 13, and the like is I. For example, the inertia moment I can be determined based on a (known) total mass of respective members swinging about the driving axis line 6J, a gravity center position of the total mass (that indicates a distance from the driving axis line 6J and is known), and a mass of the lower limb and a gravity center position of the lower limb (that indicates a distance from the driving axis line 6J and is known) estimated from a user's weight and height, and the following equations (5) and (6) are established. Since the value of ω is known from the above and the inertia moment I is also known, the apparent spring constant k1 of the flat spiral spring 24 seen from the side of the femoral swinging arm 13 can be determined by the following equation (6).

$$\omega = \sqrt{(k1/I)} \qquad \text{Equation (5)}$$

$$k1 = I \cdot \omega^2 \qquad \text{Equation (6)}$$

Moreover, when a viscosity coefficient about a joint axis (the driving axis line 6J) is ρ, the motion equation of the femoral swinging arm 13 is generally expressed by the following equation (7). Note that the following equation (7) uses τ, I, and k1 described above and expresses a swinging angle as θ.

$$\tau = I \cdot \ddot{\theta} + \rho \cdot \dot{\theta} + k1 \cdot \theta \qquad \text{Equation (7)}$$

$$\left( \ddot{\theta} = \frac{d^2\theta}{dt^2}, \dot{\theta} = \frac{d\theta}{dt} \right)$$

The swinging of a femoral part produces a substantially sine wave. Therefore, when it is substituted into the above equation (7) as θ=A·sin ωt, the following equation (7A) can be obtained.

$$\tau = -A \cdot I \cdot \omega^2 \cdot \sin\omega t + A \cdot \rho \cdot \omega \cdot \qquad \text{Equation (7A)}$$
$$\cos\omega t + A \cdot k1 \cdot \sin\omega t$$
$$= A(k1 - I \cdot \omega^2) \cdot \sin\omega t + A \cdot \rho \cdot \omega \cdot \cos\omega t$$

When k1=I·ω², i.e., a resonance state is produced in the above equation (7A), τ can be minimized. Accordingly, energy that is the product of a torque and an angular displacement can also be minimized.

In the example of FIG. 24, the speed ratio n that minimizes the consumption power of the electric motor 11 when the femoral swinging arm 13 swings in the clockwise direction at the swinging angle θf is the target rigidity speed ratio, and the speed ratio n determined by the above equations (7) and (2) is the target rigidity speed ratio. In addition, by the above equations (6) and (2), the speed ratio n according to the angular frequency co and the inertia moment I (the speed ratio n at which the resonance frequency of the flat spiral spring and the swinging frequency of a swinging object coincide with each other) can be determined.

Hereinafter, a description will be given of a method for calculating a target rigidity speed ratio (a target rigidity speed ratio with respect to a swinging angle θr of the femoral swinging arm 13 in the "counterclockwise" direction). A description will be given of a procedure for calculating a target rigidity speed ratio performed in step S30 of the flowchart shown in FIG. 26, i.e., an example of a case in which the femoral swinging arm 13 swings in the "counterclockwise" direction at the swinging angle θr. In this case, a swinging angle nθr is input to the input/output shaft 25G of the transmission 25 in the "counterclockwise" direction with a speed ratio (n) of the transmission 25. In addition, when efficiency of the transmission 25 is an apparent spring constant of the flat spiral spring 24 seen from the side of the femoral swinging arm 13 is k2, a spring constant of the flat spiral spring 24 seen from the side of the spring supporting body 22J is k, and a torque generated when the femoral swinging arm 13 swings is τ, the following equation (8) is established.

$$\tau = k2 \cdot \theta r = \eta \cdot k \cdot n^2 \theta r \qquad \text{Equation (8)}$$

When the above equation (8) is transformed, the apparent spring constant k2 of the flat spiral spring 24 seen from the side of the femoral swinging arm 13 can be determined by the following equation (9). In addition, the following equation (10) can be obtained when the following equation (9) is transformed.

$$k2 = \eta \cdot n^2 \cdot k \qquad \text{Equation (9)}$$

$$n = \sqrt{[k2/(\eta \cdot k)]} \qquad \text{Equation (10)}$$

For example, it is evident from the above equation (9) that a current speed ratio n is changed to √2·n, which is √2 times the current speed ratio n, when the apparent spring constant k2 of the flat spiral spring 24 seen from the side of the femoral swinging arm 13 is doubled.

Here, when a walking frequency (a swinging frequency of the femoral swinging arm) of a user is f and an angular frequency (angular speed) is co at this time, the above equation (4) is established. In addition, when an apparent spring constant of the flat spiral spring 24 seen from the side of the femoral swinging arm 13 is k2 and an inertia moment about the driving axis line 67 in the swinging object including the lower limb of a user, the femoral swinging arm 13, and the like is I as in the above, the following equations (11) and (12) are established. Since the value of co is known from the above and the inertia moment I is also known, the apparent spring constant k2 of the flat spiral spring 24 seen from the side of the femoral swinging arm 13 can be determined by the following equation (12).

$$\omega = \sqrt{(k2/I)} \qquad \text{Equation (11)}$$

$$k2 = I \cdot \omega^2 \qquad \text{Equation (12)}$$

Moreover, when a viscosity coefficient about a joint axis (the driving axis line 67) is ρ, the motion equation of the femoral swinging arm 13 is generally expressed by the following equation (13). Note that the following equation (13) uses τ, I, and k2 described above and expresses a swinging angle as θ.

$$\tau = I \cdot \ddot{\theta} + \rho \cdot \dot{\theta} + k2 \cdot \theta \qquad \text{Equation (13)}$$

$$\left( \ddot{\theta} = \frac{d^2\theta}{dt^2}, \dot{\theta} = \frac{d\theta}{dt} \right)$$

The swinging of a femoral part produces an almost sine wave. Therefore, when it is substituted into the above equation (13) as θ=A·sin ωt, the following equation (13A) can be obtained.

$$\tau = -A \cdot I \cdot \omega^2 \cdot \sin \omega t + A \cdot \rho \cdot \omega \cdot \cos \omega t + A \cdot k2 \cdot \sin \omega t = A(k2 - I \cdot \omega^2) \cdot \sin \omega t + A \cdot \rho \cdot \cos \omega t \qquad \text{Equation (13A)}$$

When k2=I·ω² is established, i.e., a resonance state is produced in the above equation (13A), τ can be minimized. Accordingly, energy that is the product of a torque and an angular displacement can also be minimized.

In the example of FIG. 24, the speed ratio n that minimizes the consumption power of the electric motor 11 when the femoral swinging arm 13 swings in the "counterclockwise" direction at the swinging angle θr is the target rigidity speed ratio, and the speed ratio n obtained by the above equations (13) and (9) is the target rigidity speed ratio. In addition, by the above equations (12) and (9), the speed ratio n according to the angular frequency co and the inertia moment I (speed ratio n at which the resonance frequency of the flat spiral spring and the swinging frequency of the swinging object coincide with each other) can be obtained.

As described above, the speed ratio (n) of the transmission 25 is adjusted by the control portion 50 to make the resonance angular frequency (ω) of the flat spiral spring 24 and the swinging frequency of the swinging object coincide with each other, based on the swinging frequency (f) of the femoral swinging arm 13 about the driving shaft member 6, the inertia moment (I) about the driving shaft member 6 in the swinging object including the femoral swinging arm 13 (all objects including the lower limb of a user and the femoral swinging arm 13 and swinging about the driving axis line 6J), the spring constant (k) of the flat spiral spring 24, and the swinging angle (θf) of the femoral swinging arm 13 in the clockwise direction or the swinging angle (θr) of the femoral swinging arm 13 in the "counterclockwise" direction.

As described above, the speed ratio n of the transmission 25 is adjusted such that the resonance angular frequency (ω) of the flat spiral spring 24 coincides with the swinging frequency of the swinging object (the whole object swinging about the driving shaft member 6) including the femoral swinging arm 13. Thus, power consumed by the electric motor 11 can be minimized. Note that the speed ratio n may not be calculated according to the above equation but may be calculated according to other methods. That is, in another method, the speed ratio is minutely changed, and the consumption power of the electric motor 11 for a prescribed cycle is measured at the speed ratio. After that, the speed ratio is minutely changed again, and the consumption power of the electric motor 11 for the prescribed cycle is measured. By repeatedly measuring the consumption power of the electric motor 11 in this manner, the speed ratio resulting in the minimum consumption power can be calculated. In addition, by amplifying the swinging angle of the femoral swinging arm 13 with the transmission 25 and inputting the amplified swinging angle to the flat spiral spring 24, it is possible to use a small flat spiral spring having a relatively small spring constant. Moreover, it is also possible to use a small electric motor having a smaller torque, as the electric motor 21.

The swinging joint device 1 of the seventh embodiment described above is used for the left leg of a user. However, the control unit 5 may assist the walking (or running) action of both legs of a user with the addition of a base portion for the right leg (symmetrical to the base portion 2), a femoral swinging portion for the right leg (symmetrical to the respective members indicated by symbols 11, 12, 14, 14B, 15, 13, 19, and the like), a rigidity adjustment portion for the right leg (symmetrical to the respective members indicated by symbols 21, 22, 24, 25, and the like), and a crus swinging portion for the right leg (symmetrical to the respective members indicated by symbols 31, 32, 32P, 32B, 33, 34, 35, 36, 39, and the like).

Hereinafter, a description will be given of a swinging joint device of an eighth embodiment. The swinging joint device of the eighth embodiment is one in which the electric motor 11 (and the rotation angle detection portion 11S), the bracket 12, the pulley 14, and the belt 14B are removed from the swinging joint device 1 of the seventh embodiment in FIGS. 17 to 20 and a rotation angle detection portion capable of detecting a swinging angle of the femoral swinging arm 13 is added to the swinging joint device 1 of the seventh embodiment. In the eighth embodiment, the motion of a femoral part cannot be assisted by an electric motor when a user walks (or runs), but the motion of a crus part can be assisted by the electric motor 31. In addition, since the swinging joint device includes the rigidity adjustment portion indicated by symbols 21, 22, 24, 25, and the like, it is possible to set the speed ratio n of the transmission at an appropriate speed ratio so as to produce a resonance state at all times. Thus, a motion amount of the femoral part of a user can be appropriately reduced.

In addition, as is the case with the seventh embodiment, the control unit 5 may assist the walking (or running) action of both legs of a user with the addition of a base portion for the right leg (symmetrical to the base portion 2), a femoral swinging portion for the right leg (symmetrical to the respective members indicated by symbols 13, 19, and the like), a rigidity adjustment portion for the right leg (symmetrical to the respective members indicated by symbols 21, 22, 24, 25, and the like), and a crus swinging portion for the right leg (symmetrical to the respective members indicated by symbols 31, 32, 32P, 32B, 33, 34, 35, 36, 39, and the like).

Hereinafter, a description will be given of a swinging joint device of a ninth embodiment. The swinging joint device of the ninth embodiment is one in which the electric motor 31, the bracket 32, the pulley 32P, the belt 32B, the ems swinging arm 33, the ems relaying arm 34, the crus arm 35, the foot holding portion 36, and the ems attachment portion 39 are removed from the swinging joint device 1 of the seventh embodiment shown in FIGS. 17 to 20. In the ninth embodiment, the motion of a femoral part is assisted by the electric motor 11 when a user walks (or runs), but the motion of a ems part is not assisted. Note that since the swinging joint device includes the rigidity adjustment portion indicated by symbols 21, 22, 24, 25, and the like, it is possible to set the speed ratio n of the transmission 25 at an appropriate speed ratio so as to produce a resonance state at all times. Thus, the consumption power of the electric motor 11 can be further reduced.

In addition, as is the case with the seventh embodiment, the control unit 5 may assist the walking (or running) action of both legs of a user with the addition of a base portion for the right leg (symmetrical to the base portion 2), a femoral swinging portion for the right leg (symmetrical to the respective members indicated by symbols 11, 12, 14, 14B, 15, 13, 19, and the like), and a rigidity adjustment portion for the right leg (symmetrical to the respective members indicated by symbols 21, 22, 24, 25, and the like).

Hereinafter, a description will be given of a swinging joint device of a tenth embodiment. The swinging joint device of the tenth embodiment is one in which the electric motor 11 (and the rotation angle detection portion 11S), the bracket 12, the pulley 14, and the belt 14B are removed from the swinging joint device of the ninth embodiment and a rotation angle detection portion capable of detecting a swinging angle of the femoral swinging arm 13 is added to the swinging joint device of the ninth embodiment. In the tenth embodiment, the motion of a crus part cannot be assisted when a user walks (or runs). In addition, the motion of the femoral part of a user cannot be assisted by an electric motor. However, since the swinging joint device includes the rigidity adjustment portion indicated by symbols 21, 22, 24, 25, and the like, it is possible to set the speed ratio n of the transmission 25 at an appropriate speed ratio so as to produce a resonance state at all times. Thus, a motion amount of the femoral part of a user can be appropriately reduced.

In addition, as is the case with the seventh embodiment, the control unit 5 may assist the walking (or running) action of both legs of a user with the addition of a base portion for the right leg (symmetrical to the base portion 2), a femoral swinging portion for the right leg (symmetrical to the respective members indicated by symbols 13, 19, and the like), and a rigidity adjustment portion for the right leg (symmetrical to the respective members indicated by symbols 21, 22, 24, 25, and the like).

It is possible to make various modifications, additions, and deletions to the swinging joint device of the invention without departing from the scope of the invention.

The application of the swinging joint device described in the embodiments is not limited to assisting the swinging motion (such as walking and running) of the lower limb of a user, but the swinging joint device may be applied to various objects that perform cyclic swinging motion.

The swinging and rotating motion of the electric motor 11 and the electric motor 31 is transmitted to the femoral swinging arm 13 and the crus swinging arm 33 by the pulleys and the belts in the embodiments, but may be transmitted using gears, a link mechanism, and the like instead of the pulleys and the belts.

What is claimed is:
1. A swinging joint device comprising:
a driving shaft member;
a first output portion that swings about a driving axis serving as an axis of the driving shaft member;
an elastic body that includes a spring and that generates a biasing torque corresponding to a first swinging angle that is an angle measured from an initial position of the first output portion to a position reached by the first output portion;
a rigidity variable portion that varies rigidity of the elastic body associated with motion of the first output portion;
a first angle detection portion that detects the first swinging angle; and
a control portion that controls the rigidity variable portion according to the first swinging angle detected by the first angle detection portion to adjust the rigidity of the elastic body associated with motion of the first output portion, wherein the rigidity of the elastic body associated with motion of the first output portion includes a spring constant of the spring associated with motion of the first output portion;

wherein the rigidity variable portion that varies the rigidity of the elastic body associated with motion of the first output portion includes a spring constant variable portion that varies the spring constant of the spring associated with motion of the first output portion; and wherein the spring is a flat spiral spring.

2. The swinging joint device according to claim 1, wherein:
   a spring fixing member that supports a fixed end of the flat spiral spring is disposed at a position adjacent to the flat spiral spring;
   a free end serving as one end of the flat spiral spring is connected to a spring input shaft member that swings at an angle corresponding to the first swinging angle of the first output portion;
   the fixed end serving as the other end of the flat spiral spring is connected to a spring supporting body provided on the spring fixing member at a position distant from the driving axis; and
   the spring constant variable portion is constituted by the spring fixing member that is supported so as to be pivotable about the driving axis and is caused to pivot about the driving axis at a prescribed pivoting angle to move a position of the spring supporting body relative to the driving axis about the driving axis by the prescribed pivoting angle, and a rigidity adjustment member that causes the spring fixing member to pivot about the driving axis to vary a position of the fixed end of the flat spiral spring.

3. The swinging joint device according to claim 2, wherein:
   a transmission is provided between the first output portion and the flat spiral spring; and
   the transmission includes the spring input shaft member, and when the first output portion swings at the first swinging angle, the spring input shaft member swings at a swinging angle obtained by changing the first swinging angle based on a prescribed speed ratio.

4. The swinging joint device according to claim 2, wherein when the position of the spring supporting body, at which the flat spiral spring does not generate the biasing torque in a case where the first swinging angle is zero, is set as a reference position, the control portion controls the rigidity adjustment member to adjust a pivoting angle of the spring fixing member to adjust the position of the spring supporting body relative to the reference position according to the first swinging angle of the first output portion, thereby adjusting the spring constant of the flat spiral spring associated with motion of the first output portion.

5. The swinging joint device according to claim 1, further comprising
   a first driving portion that swings the first output portion about the driving axis based on a control signal from the control portion.

6. The swinging joint device according to claim 1, further comprising:
   a second output portion supported so as to be swingable about the driving axis;
   a second angle detection portion that detects a second swinging angle that is an angle measured from an initial position of the second output portion to a position reached by the second output portion;
   a second driving portion that swings the second output portion about the driving axis based on a control signal from the control portion; and
   a swinging link member that is connected to the first output portion and the second output portion and operates based on the first swinging angle of the first output portion and the second swinging angle of the second output portion.

7. A walking assisting device comprising
the swinging joint device according to claim 1.

8. A conveying device comprising
the swinging joint device according to claim 2, wherein:
   the conveying device includes the driving shaft member, a pinion that serves as the first output portion that pivots in a reciprocating manner so as to swing about the driving axis of the driving shaft member, an arm that has a rack portion engaging with the pinion and linearly reciprocates according to a swinging angle that is a reciprocally-pivoting angle of the pinion, the arm being configured to hold and release a workpiece, a pinion driving portion that rotates and drives the pinion, the first angle detection portion that detects the first swinging angle that is the swinging angle of the pinion, the flat spiral spring that accumulates energy when the pinion driving portion rotates and drives the pinion, and rotates and drives the pinion when releasing the accumulated energy, the spring constant variable portion including the spring fixing member and the rigidity adjustment member, and the control portion that controls the pinion driving portion and the rigidity adjustment member; and
   the conveying device moves the workpiece by linearly reciprocating the arm to hold and release the workpiece.

9. A manipulator comprising
the swinging joint device according to claim 2, wherein:
   the manipulator includes the driving shaft member, a swinging portion serving as the first output portion that swings about the driving axis of the driving shaft member, a swinging portion driving portion that swings the swinging portion, the first angle detection portion that detects the first swinging angle that is a swinging angle of the swinging portion, the flat spiral spring that accumulates energy when the swinging portion driving portion swings the swinging portion, and swings the swinging portion when releasing the accumulated energy, the spring constant variable portion including the spring fixing member and the rigidity adjustment member, and the control portion that controls the swinging portion driving portion and the rigidity adjustment member.

10. A walking-ability assisting device that applies an assisting force to motion of a lower limb of a user, comprising:
   a waist-side attachment portion configured to be attached to a waist-side portion of the user;
   a first swinging arm that has an elongate shape and is to be disposed on a lateral side of a femoral part of the user, the first swinging arm having one of a protruding portion and a recessed portion located at an upper portion of the first swinging arm, and the one of the protruding portion and the recessed portion serving as a swinging axis of the first swinging arm;
   a femoral attachment portion attached to the first swinging arm to be put on the femoral part of the user;

a driving shaft member that supports the one of the protruding portion and the recessed portion that serves as the swinging axis of the first swinging arm, the driving shaft member supporting the first swinging arm such that the first swinging arm is swingable in a front-rear direction of the user relative to the waist-side attachment portion;

a rigidity variable portion that varies rigidity representing a force required for swinging the first swinging arm swinging about a driving axis serving as an axis of the driving shaft member; and a control portion that controls the rigidity variable portion to control the rigidity of the first swinging arm swinging about the driving axis, wherein:

the rigidity variable portion is constituted by a flat spiral spring, a spring fixing member, and a rigidity adjustment pivoting member;

the flat spiral spring, the spring fixing member, and the rigidity adjustment pivoting member are disposed so as to be coaxial with the driving axis;

a spring fixing member that supports a fixed end of the flat spiral spring is disposed at a position adjacent to the flat spiral spring;

a free end serving as one end of the flat spiral spring is connected to a spring input shaft member that swings at an angle corresponding to a first swinging angle that is angle measured from an initial position of the first swinging arm to a position reached by the first swinging arm;

the fixed end serving as the other end of the flat spiral spring is connected to a spring supporting body provided on the spring fixing member at a position distant from the driving axis; and the rigidity adjustment pivoting member adjusts the rigidity by pivoting the spring fixing member about the driving axis to move a position of the fixed end of the flat spiral spring based on a control signal from the control portion.

11. The walking-ability assisting device according to claim 10, wherein:

a transmission is provided between the first swinging arm and the flat spiral spring; and the transmission includes the spring input shaft member, and when the first swinging arm swings at the first swinging angle, the spring input shaft member swings at a swinging angle obtained by changing the first swinging angle based on a prescribed speed ratio.

12. The walking-ability assisting device according to claim 10, further comprising a first angle detection portion that detects the first swinging angle of the first swinging arm, wherein the control portion controls the rigidity adjustment pivoting member to adjust a pivoting angle of the spring fixing member according to the first swinging angle detected by the first angle detection portion, and adjusts a spring constant of the flat spiral spring associated with motion of the first swinging arm, to adjust the rigidity.

13. The walking-ability assisting device according to claim 12, wherein the control portion adjusts the pivoting angle of the spring fixing member such that a resonance frequency of the flat spiral spring coincides with a swinging frequency of a swinging object, based on the swinging frequency and the first swinging angle of the first swinging arm about the driving axis, an inertia moment about the driving axis in the swinging object including the first swinging arm, and a spring constant of the flat spiral spring.

14. The walking-ability assisting device according to claim 10, further comprising a first driving portion that swings the first swinging arm about the driving axis, based on the control signal from the control portion.

15. The walking-ability assisting device according to claim 10, further comprising:

a second swinging arm supported so as to be swingable about the driving axis;

a second angle detection portion that detects a second swinging angle that is an angle measured from an initial position of the second swinging arm to a position reached by the second swinging arm;

a second driving portion that swings the second swinging arm about the driving axis, based on the control signal from the control portion;

a swinging link member that is connected to the first swinging arm and the second swinging arm and operates based on the first swinging angle of the first swinging arm and the second swinging angle of the second swinging arm; and a crus attachment portion attached to the second swinging arm to be put on a crus part of the user.

\* \* \* \* \*